United States Patent [19]

Gregson et al.

[11] 4,209,616

[45] Jun. 24, 1980

[54] SYN ISOMERS OF CEPHALOSPORINS HAVING α-HYDROXIMINO- OR α-ACYLOXYIMINOACYLAMIDO GROUPS AT POSITION-7

[75] Inventors: Michael Gregson, London; Martin C. Cook; Gordon I. Gregory, both of Chalfont St. Peter, all of England

[73] Assignee: Glaxo Laboratories Limited, Greenford, England

[21] Appl. No.: 951,761

[22] Filed: Oct. 16, 1978

Related U.S. Application Data

[60] Continuation of Ser. No. 771,807, Feb. 24, 1977, abandoned, which is a division of Ser. No. 554,014, Feb. 28, 1975, Pat. No. 4,024,134, which is a continuation of Ser. No. 274,602, Jul. 24, 1972, abandoned, which is a continuation-in-part of Ser. No. 221,057, Jan. 26, 1972, abandoned.

[30] Foreign Application Priority Data

Jan. 29, 1971 [GB] United Kingdom ............... 3531/71
Oct. 1, 1971 [GB] United Kingdom ............. 45885/71

[51] Int. Cl.² .................................... C07D 501/20
[52] U.S. Cl. ...................................... 544/28; 544/30; 424/246
[58] Field of Search ................... 544/30, 16, 28

[56] References Cited

U.S. PATENT DOCUMENTS

| 3,546,219 | 12/1970 | Long et al. | 260/243 C |
|---|---|---|---|
| 3,573,294 | 3/1971 | Long et al. | 260/243 C |
| 4,024,133 | 5/1977 | Cook et al. | 544/28 |
| 4,024,134 | 5/1977 | Gregson et al. | 544/28 |

FOREIGN PATENT DOCUMENTS 1073530  12/1963  United Kingdom ................ 544/28

*Primary Examiner*—Nicholas S. Rizzo
*Attorney, Agent, or Firm*—Bacon & Thomas

[57] ABSTRACT

The invention provides novel antibiotic compounds which are 7β-acylamidoceph-3-em-4-carboxylic acids, and non-toxic derivatives thereof, and 6β-acylamidopenam-3-carboxylic acids, and non-toxic derivatives thereof, characterized in that the acylamido group has the structure

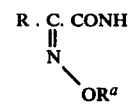

where R is a hydrogen atom or an organic group and $R^a$ is a hydrogen atom or an acyl group. The compounds are syn isomers or exist as mixtures containing at least 75% of the syn isomer. These antibiotic compounds possess high antibacterial activity against a range of gram positive and gram negative organisms coupled with particularly high stability to β-lactamases produced by various gram negative organisms. The invention is also concerned with the administration of the compounds.

25 Claims, No Drawings

SYN ISOMERS OF CEPHALOSPORINS HAVING α-HYDROXIMINO- OR α-ACYLOXYIMINOACYLAMIDO GROUPS AT POSITION-7

CROSS REFERENCE TO RELATED APPLICATION

This application is a continuation of application Ser. No. 771,807 filed on Feb. 24, 1977, now abandoned, which, in turn, is a division of application Ser. No. 554,014, filed Feb. 28, 1975, and now U.S. Pat. No. 4,024,134, which is, in turn, a continuation of application Ser. No. 274,602, filed July 24, 1972, and now abandoned, which is, in turn, a continuation-in-part of application Ser. No. 221,057, filed Jan. 26, 1972, and now abandoned.

This invention is concerned with improvements in or relating to antibiotics of the cephalosporin and penicillin series.

As is well known, antibiotics of the cephalosporin and penicillin series are respectively 7β-acylamidoceph-3-em-4-carboxylic acids and 6β-acylamidopenam-3-carboxylic acids and their various non-toxic derivatives, e.g. salts, esters, lactones (if such can be formed), amides, hydrates or the corresponding sulphoxides. In the cephalosporin series, these antibiotics may contain various substituents at the 3-position including unsubstituted methyl and methyl groups substituted with a variety of substituents as is described in the literature. In the penicillin series, substitution may, for example, be present on at least one of the gem-dimethyl groups.

The new compounds of the present invention are characterized in that said acylamido group of the cephalosporin or penicillin antibiotic is an α-hydroxyiminoacylamido or α-acyloxyiminoacylamido group, the compounds being syn isomers or mixtures wherein the syn isomeric form predominates.

According to one embodiment of the invention, therefore, we provide a compound selected from the group of 7β-acylamidoceph-3-em-4-carboxylic acids (and non-toxic derivatives thereof) and 6β-acylamidopenam-3-carboxylic acids (and non-toxic derivatives thereof) characterized in that said acylamido group has the structure:

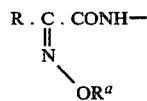

where R is a hydrogen atom or an organic group and $R^a$ is a hydrogen atom or an acyl group, said compound being a syn isomer or existing as a mixture containing at least 75% of the syn isomer.

The compounds of the invention are defined as having the syn (cis) isomeric form as regards the configuration of the group $OR^a$ with respect to the carboxamido group. Preferably, the mixtures of isomers contain at least 90% of the syn isomer and not more than 10% of the anti.

In this specification, the syn configuration is structurally denoted thus:

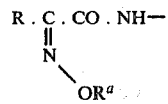

and the anti configuration thus:

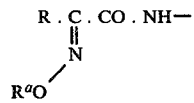

These configurations are allocated on the work of Ahmad and Spencer, Can. J. Chem, 1961, 39, 1340.

The compounds of the invention may be defined by the formula:

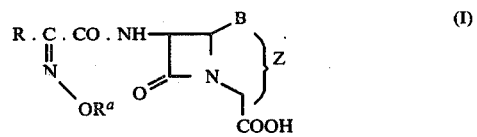

where $R^a$ has the above-defined meaning, R is a hydrogen atom or an organic group B is >S or >S→O and Z is a group in which 1 or 2 carbon atoms link the nuclear sulphur atom and the carbon atom bearing the carboxyl group.

The term "non-toxic" as applied to the derivatives of the compounds of the invention means those derivatives which are physiologically acceptable in the dosage at which they are administered.

Salts which may be formed, where applicable, from the compounds according to the invention include (a) inorganic base salts such as alkali metal, e.g. sodium and potassium, alkaline earth metal e.g. calcium, and organic base, e.g. procaine, phenylethylbenzylamine and dibenzylethylene diamine, salts and (b) acid addition salts e.g., with hydrochloric, hydrobromic, sulphuric, nitric, phosphoric, toluene-p-sulphonic and methane sulphonic acids. The salts may also be in the form of resinates, formed e.g., with a polystyrene resin containing amino, quaternary amino, or sulphonic acid groups, or a resin containing carboxyl groups, e.g. a polyacrylic acid resin. The resin may if desired be cross-linked, e.g. it may be a copolymer of styrene and divinyl-benzene containing the appropriate groups. Additionally, the derivatives may be in the form of a chelate with a heavy metal such as iron or copper.

The compounds of the invention, including the non-toxic derivatives thereof, are characterized by their high antibacterial activity against a range of gram-positive and gram-negative organisms coupled with particularly high stability to β-lactamases produced by various gram negative organisms.

Stability to β-lactamases may be assessed as compared with cephaloridine which may be arbitrarily defined as having a value of 1 with respect to the particular organism.

The cephalosporin compounds referred to in this specification are generally named with reference to cepham (J. Amer. Chem. Soc. 1962, 84 3400). The term "cephem" refers to the basic cepham structure with one double bond. The penicillin compounds referred to in this specification are generally named with reference to penam (J. Amer. Chem. Soc. 1953, 75, 3293).

The cephalosporin compounds according to the invention may be defined as compounds of the general formula

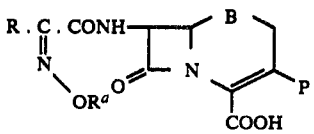   (II)

(wherein R, $R^a$ and B have the above defined meanings, P is an organic group) and non-toxic derivatives thereof.

The penicillin compounds according to the invention may be defined as compounds of the general formula

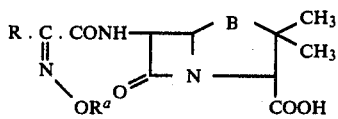   (III)

(wherein R, $R^a$ and B have the above-defined meanings) and non-toxic derivatives thereof.

In formulae (II) and (III) B is preferably >S.

The invention also includes cephalosporin and penicillin compounds not specifically embraced by formulae (II) or (III) e.g. $2\beta$-acetoxymethyl penicillins and 2-methyl and 2-methylene cephalosporins.

The group $R^a$ in the above formulae, when it is acyl, may be chosen from a wide variety of possible groups. Thus the group $R^a$ may be a carboxylic acyl group $R^cCO$ having from 1 to 20 carbon atoms. In particular $R^c$ may be an aliphatic, cycloaliphatic or aromatic group or it may be such an organic group linked to the carbonyl group through an oxygen atom, a sulphur atom or an imino group. Such an aliphatic, cycloaliphatic or aromatic group may be substituted by halogen (F, Cl, Br or I), amino, nitro, $C_1$-$C_5$ alkyl, $C_1$-$C_6$ alkoxy etc.

Particular Examples of $R^a$ include alkanoyl, alkenoyl and alkynoyl of up to 7 carbon atoms e.g. acetyl, propionyl, butyryl, acrylyl, crotonyl; substituted, e.g. halogenated (F, Cl, Br, I) or amino or substituted amino derivatives of such groups e.g. chloroacetyl, dichloroacetyl or $\beta$-aminopropionyl; alkoxycarbonyl of up to 7 carbon atoms e.g. ethoxycarbonyl, and t-butoxycarbonyl; substituted alkoxycarbonyl e.g. 2,2,2-trichloroethoxycarbonyl; alkylthiocarbonyl of up to 7 carbon atoms and substituted derivatives thereof; aralkyloxycarbonyl e.g. benzhydryloxycarbonyl and benzyloxycarbonyl; $C_7$-$C_{13}$ aroyl e.g. benzoyl and substituted, e.g. nitrated derivatives of such groups e.g. nitrobenzoyl; and substituted or unsubstituted carbamoyl or thiocarbamoyl i.e. compounds in which the group $R^a$ has the formula $(R^b)_2N.CO-$ or $(R^b)_2N.CS-$ and $R^b$ is the same or different and each is a hydrogen atom or a substituent such as alkyl of 1-7 carbon atoms e.g. ethyl or methyl and substituted, e.g. halogenated, alkyl of 1-7 carbon atoms e.g. chloroethyl, or $R^u$, where $R^u$ has the meaning defined below.

The group R in the above general formulae may be chosen from the following list which is not intended to be exhaustive:

(i) Hydrogen, (ii) $R^u$, where $R^u$ is aryl (carbocyclic or heterocyclic), cycloalkyl, substituted aryl, substituted cycloalkyl, cycloalkadienyl, or a non-aromatic or mesionic group. Examples of this group include phenyl; naphthyl; phenyl or naphthyl substituted by halo e.g. chloro or bromo, hydroxy, lower alkyl e.g. methyl, nitro, amino, lower alkylamino e.g. methylamino, diloweralkylamino e.g. dimethylamino, lower alkanoyl e.g. acetyl, lower alkanoylamido, lower alkoxy e.g. methoxy or ethoxy, or lower alkylthio e.g. methylthio; a 5- or 6-membered heterocyclic group containing at least one hetero atom selected from S, N and O e.g. thien-2-yl, thien-3-yl, furyl, pyridyl, 3- or 4-isoxazolyl; substituted 3- or 4-isoxazolyl e.g. 3-aryl-5-methylisoxazol-4-yl, the aryl group being e.g. phenyl or halophenyl; cyclohexyl; cyclopentyl; sydnone; and cyclohexadienyl.

(iii) $R^u(CH_2)_mQ_n(CH_2)_p$ where $R^u$ has the above defined meaning and m is 0 or an integer from 1 to 4, n is 0 or 1, p is an integer from 1 to 4 and Q is S, O or NR wherein R is hydrogen or an organic group e.g. alkyl such as methyl or aryl such as phenyl. Examples of this group include methyl, ethyl or butyl substituted by the various specific $R^u$ groups listed under (ii) e.g. benzyl and the appropriate substituted benzyl groups.

(iv) $C_nH_{2n+1}$ wherein n is an integer from 1 to 7. The group may be straight or branched and, if desired, may be interrupted by an oxygen or sulphur atom or the group NR wherein R is hydrogen or an organic group e.g. alkyl such as methyl or aryl such as phenyl; or be substituted by a cyano, carboxy, alkoxycarbonyl, hydroxy or carboxycarbonyl (HOOC.CO.) group or by a halogen atom. Examples of such groups include hexyl, heptyl, butylthiomethyl, cyanomethyl or trihalomethyl.

(v) $C_nH_{2n-1}$ where n is an integer from 2 to 7. The group may be straight or branched and, if desired, may be interrupted by an oxygen or sulphur atom or the group NR wherein R is hydrogen or an organic group e.g. alkyl such as methyl or aryl such as phenyl. An example of such a group is vinyl or propenyl.

(vi) $C_nH_{2n-3}$ where n is an integer from 2 to 7. An example of such a group is ethynyl.

(vii) Miscellaneous carbon-linked organic groups including cyano, amido and lower alkoxycarbonyl.

The 3-substituent P of the above cephalosporin compounds may be any organic group, the characterising feature of the invention being the nature of the 7-substituent. P may thus be a saturated or unsaturated, substituted or unsubstituted, organic group containing 1–20 carbon atoms. Preferred saturated organic groups include methyl and ethyl; preferred unsaturated organic groups include vinyl and substituted vinyl groups of the formula

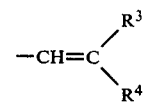

wherein $R^3$ and $R^4$, which may be the same or different, are each hydrogen or a substituted or unsubstituted aliphatic (e.g. alkyl, preferably $C_1$-$C_6$ alkyl such as methyl, ethyl, iso-propyl, n-propyl etc.), $C_5$-$C_7$ cycloaliphatic (e.g. cyclopentyl or cyclohexyl), $C_7$-$C_{10}$ araliphatic (e.g. benzyl or phenvlethyl), $C_6$-$C_{12}$ aromatic (e.g. phenyl or nitrophenyl) group, nitrile or lower alkoxycarbonyl.

When P is a substituted methyl group it may be depicted by the formula

—$CH_2Y$ wherein Y is an atom or group e.g. the residue of a nucleophile or a derivative of a residue of a nucleophile. Y may thus, for example, be derived from the wide range of nucleophilic substances characterized by possessing a nucleophilic nitrogen, carbon, sulphur or oxygen atom described widely in earlier patents and literature pertaining to cephalosporin chemistry. Examples of such nucleophiles include:

NITROGEN NUCLEOPHILES

Examples of nitrogen nucleophiles include tertiary aliphatic, aromatic, araliphatic and cyclic amines including trialkylamines, for example, triethylamine, pyridine bases such as pyridine and alkyl pyridines; heterocyclic amines having more than one heteroatom, at least one heteroatom being nitrogen, such as pyrimidines, purines, pyridazines, pyrazines, pyrazoles, imidazoles, triazoles and thiazoles.

A preferred class of nitrogen nucleophile are those compounds of the formula:

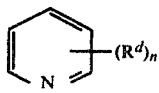

in which n is 0 or an integer from 1 to 5 and $R^d$, which when n is from 2 to 5, may be the same or different, is an aliphatic, e.g. lower alkyl such as methyl, ethyl, n-propyl, iso-propyl etc; an aryl e.g. phenyl; an araliphatic, e.g. phenyl lower alkyl such as benzyl, phenylethyl etc; or an alkoxymethyl e.g. methoxymethyl, ethoxymethyl, n-propoxymethyl, iso-propoxymethyl etc; or acyloxymethyl e.g. alkanoyloxymethyl such as acetoxymethyl; formyl; carbamoyl; acyloxy e.g. alkanoyloxy such as acetoxy; esterified carboxyl; alkoxy e.g. methoxy, ethoxy, n-propoxy, iso-propoxy etc; aryloxy e.g. phenoxy; aralkoxy e.g. benzyloxy; alkylthio e.g. methylthio, ethylthio; arylthio; aralkylthio; cyano; hydroxy; N-monoloweralkylcarbamoyl e.g. N-methylcarbamoyl, N-ethylcarbamoyl etc; N,N-diloweralkylcarbamoyl e.g. N,N-dimethylcarbamoyl, N,N-diethylcarbamoyl etc; N-(hydroxyloweralkyl)carbamoyl e.g. N-(hydroxymethyl)carbamoyl, N-(hydroxyethyl)carbamoyl etc; or carbamoylloweralkyl e.g. carbamoylmethyl, carbamoylethyl etc. group.

Another preferred class of nitrogen nucleophiles are azides e.g. alkali metal azides such as sodium azide.

When the group Y is a derivative of a residue of a nucleophile it may be an amino group or an acylamido group. Compounds in which Y is amino may be derived from the corresponding azide by reduction e.g. by catalytic hydrogenation of the azide using a precious metal catalyst such as palladium or platinum.

The amino group may be acylated to form a corresponding 3-acylaminomethyl compound. The formation of such compounds may, for example, be effected by any method suitable for acylating an aminocephalosporin e.g. reaction of the 3-aminomethyl compound with an acid chloride, acid anhydride or mixed anhydride or an acid corresponding to the desired acyl group and another acid.

The 3-aminomethyl compounds may also be reacted with a substituted isocyanate or isothiocyanate to yield urea or thiourea derivatives.

Other compounds in which Y is a derivative of a residue of a nucleophile may be obtained by reacting 3-azidomethyl compounds with a dipolarophile. Preferred classes of dipolarophiles include acetylenic, ethylenic and cyano dipolarophiles.

Acetylenic dipolarophiles may be shown as having the structure

where $R^1$ and $R^2$ which may be the same or different are atoms or groups.

In general we prefer that $R^1$ and preferably also $R^2$ should be of an electronegative nature. Examples of such groups include cyano, $CO_2R^3$, $COR^3$ (where $R^3$ is for example, lower alkyl, aryl or lower aralkyl), and trihalomethyl e.g. trifluoromethyl.

However, $R^1$ and preferably also $R^2$ could be electropositive e.g. alkoxy or alkylamino.

$R^1$ and $R^2$ may together form a ring system with the acetylenic group such as, for example, in an aryne.

Where $R^1$ and $R^2$ are discrete atoms or groups which are identical a single compound will result on reaction with the azido cephalosporin; if they are different one will in general obtain a mixture of position isomers.

Ethylenic dipolarophiles may be shown as having the structure

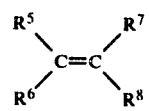

where $R^5$, $R^6$, $R^7$ and $R^8$ which may be the same or different are atoms or groups. Although $R^5$, $R^6$, $R^7$ and $R^8$ may all be hydrogen, ethylene per se, like acetylene, reacts sluggishly with azido groups. $R^5$ and $R^7$ may together form a cyclic structure, e.g. a carbocyclic structure, with the ethenoid group such that the double bond is strained. Examples of ethylenic dipolarophiles containing strained double bonds include norbornenes, transcycloalkenes and acenaphthalene.

Further ethylenic dipolarophiles which may be used include compounds of the formula $R^5.R^6.C=CR^7.R^8$ where at least one of $R^5$, $R^6$, $R^7$ and $R^8$ is an electronegative group. $R^5$ and $R^7$ may thus be identical electronegative groups, $R^6$ and $R^8$ being other groups as desired. $R^6$ and $R^8$ may thus together form a ring system. Examples of such dipolarophiles include benzoquinone and nuclear substituted benzoquinones and maleimide. Again all of $R^5$, $R^6$, $R^7$ and $R^8$ may be identical electronegative groups. Electronegative groups which may be used include those listed under the section on acetylenic dipolarphiles and examples of such compounds thus include dicyanoethylene and lower mono- and di-alkoxycarbonyl ethylenes.

One or more of $R^5$, $R^6$, $R^7$ and $R^8$ may if desired be electropositive.

Cyano compounds, especially those which are activated by electronegative groups, may function as cyano dipolarophiles. Examples of such dipolarophiles include lower alkoxy carbonyl cyanides and cyanogen.

CARBON NUCLEOPHILES

Examples of "carbon nucleophiles" include inorganic cyanides, pyrroles and substituted pyrroles, e.g. indoles, and compounds giving stabilised carbanions, for example, acetylenes and compounds having $\beta$-diketone groups, for example acetoacetic and malonic esters and cyclohexane-1,3-diones or enamines, ynamines or enols.

The carbon nucleophile may thus give rise to cephalosporin compounds characterized by possessing a substituent at the 3-position in which a carbonyl group is linked to the cephalosporin nucleus through two carbon atoms. Such compounds may thus possess as the 3-substituent a group of the formula

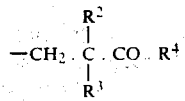

wherein $R^2$ and $R^3$, which may be the same or different, are selected from hydrogen, cyano, lower alkyl e.g. methyl or ethyl, phenyl, substituted phenyl e.g. halo, lower alkyl, lower alkoxy, nitro, amino or lower alkylamino phenyl, lower alkoxycarbonyl, mono- or di-aryl lower alkoxycarbonyl, lower alkylcarbonyl, aryl lower alkyl or $C_5$ or $C_6$ cycloalkyl and $R^4$ is selected from hydrogen, lower alkyl e.g. methyl or ethyl, phenyl, substituted phenyl e.g. halo, lower alkyl, lower alkoxy, nitro, amino or lower alkylamino phenyl, aryl lower alkyl or $C_5$ or $C_6$ cycloalkyl.

SULPHUR NUCLEOPHILES

Examples of "sulphur nucleophiles" include thiourea and aliphatic, aromatic, araliphatic, alicyclic and heterocyclic substituted thioureas; dithiocarbamates; aromatic, aliphatic and cyclic thioamides, for example thioacetamide and thiosemicarbazide; thiosulphates; thiols; thiophenols; thioacids, e.g. thiobenzoic acid or thiopicolinic acid; and dithioacids.

A preferred class of "sulphur nucleophile" includes those compounds of the formula: $R^1.S(O)_nH$ in which $R^1$ is an aliphatic e.g. lower alkyl such as methyl, ethyl, n-propyl etc. group; an alicyclic e.g. cyclohexyl, cyclopentyl etc. group; an aromatic e.g. phenyl, naphthyl etc. group; an araliphatic e.g. benzyl group; or a heterocyclic group, and n is 0, 1 or 2. A particularly preferred class of nucleophiles falling within the above formula is that having the general formula: $R^6$ SH in which $R^6$ is an aliphatic, e.g. lower alkyl e.g. methyl ethyl, n-propyl etc.; araliphatic, e.g. phenyl lower alkyl e.g. benzyl, phenylethyl etc. or substituted phenyl lower alkyl; alicyclic e.g. cycloalkyl e.g. cyclopentyl or cyclohexyl; aromatic e.g. phenyl or substituted phenyl or a 5- or 6-membered heterocyclic group containing at least one of O, N and S e.g. thiadiazolyl particularly 5-methyl-1,3,4-thiadiazol-2-yl, diazolyl, triazolyl, tetrazolyl, thiazolyl, thiatriazolyl, oxazolyl, oxadiazolyl, benzimidazolyl, benzoxazolyl, triazolopyridyl, purinyl pyridyl, pyrimidyl, etc.

OXYGEN NUCLEOPHILES

Examples of oxygen nucleophiles include water, alcohols, for example alkanols such as methanol, ethanol, propanol and butanol and lower alkanoic acids.

The term "oxygen nucleophile" thus includes compounds of the following formula:

R'OH in which the group $R^t$ may be lower alkyl (e.g. methyl, ethyl, n-propyl, isopropyl, n-butyl, isobutyl etc.); lower alkenyl (e.g. alkyl); lower alkynyl (e.g. propynyl, etc); lower cycloalkyl (e.g. cyclopentyl, cyclohexyl, etc); lower cycloalkyl lower alkyl (e.g. cyclopentylmethyl, cyclohexylethyl etc); aryl (e.g. phenyl or naphthyl); aryl lower alkyl (e.g. benzyl); heterocyclic; heterocyclic lower alkyl (e.g. furfuryl) or any of these groups substituted by, for example, one or more of lower alkoxy (methoxy, ethoxy, etc.), lower alkylthio (methylthio, ethylthio, etc), halogen (chlorine, bromine, iodine or fluorine), lower alkyl (methyl, ethyl etc), nitro, hydroxy, acyloxy, carboxy, carbalkoxy, lower alkylcarbonyl, lower alkylsulphonyl, lower alkoxysulphonyl, amino, lower alkylamino or acylamino groups.

In the case in which is the nucleophile there will be obtained 3-hydroxymethyl cephalosporin compounds. Such compounds have the formula

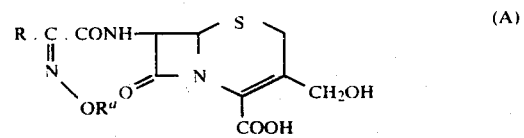

where R and $R^a$ have the above defined meanings. Compounds of formula (A) and non-toxic derivatives thereof possess antibacterial activity and it is of note that they may be metabolites of compounds of general formula (IV) where P is acyloxymethyl. Compounds of formula (A) may be acylated to form derivatives characterised by possessing the group 3—$CH_2.O.CO.R^9$ or 3—$CH_2.O.CO.ZR^9$ where Z is 0 or 5 in which $R^9$ is methyl or an organic group having an atomic weight sum of at least 16.

The group $R^9CO$— or, $R^9Z.CO$— may be chosen from among the wide class of such groups described to the literature and may have up to 20 carbon atoms. The group $R^9$ may thus be a hydrocarbon group or such a group carrying one or more substituent atoms or groups. The group $R^9$ may thus be chosen from the following list which is not intended to be exhaustive:

(i) $C_nH_{2n+1}$ where n is an integer from 1 to 7, e.g. 2 to 4. The group may be straight or branched and, if desired, may be interrupted by an oxygen or sulphur atom or an imino group or substituted by cyano, carboxy, alkoxycarbonyl, hydroxy, carboxycarbonyl (HOOC.CO.), halogen e.g. chlorine, bromine or iodine, or amino. Examples of such groups include ethyl, propyl, isopropyl, n-butyl, t-butyl or sec.butyl (ii) $C_nH_{2n-1}$ where n is an integer from 2 to 7. The group may be straight or branched and, if desired, may be interrupted by an oxygen or sulphur atom or an imino group. An example of such a group is vinyl or propenyl.

(iii) $R^v$, where $R^v$ is aryl (carbocyclic or heterocyclic), cycloalkyl, substituted aryl and substituted cycloalkyl. Examples of this group include phenyl; substituted phenyl e.g. hydroxyphenyl, chlorophenyl, fluorophenyl, tolyl, nitrophenyl, aminophenyl, methoxyphenyl or methylthiophenyl; thien-2- and -3-yl; pyridyl; cyclohexyl; cyclopentyl; sydnone; naphthyl; substituted naphthyl e.g. 2-ethoxynaphthyl.

(iv) $R^v(CH_2)_m$ where $R^v$ has the meaning defined above under (iii) and m is an integer from 1 to 4. Examples of this group include methyl, ethyl or butyl substituted by the various specific $R^v$ groups listed under (iii) e.g. benzyl and the appropriate substituted benzyl groups.

Compounds of formula (A) may also be acylated to form derivatives characterised by possessing the group 3—CH$_2$.O.CO.NH(CH$_2$)$_m$R, where R is hydrogen or halogen (Cl, Br, I or F) and m is an integer from 1–4.

An important class of cephalosporin compounds are those possessing the group 3—CH$_2$Hal wherein Hal is chlorine, bromine or iodine. Such compounds may be primarily of value as intermediates of use in the preparation of active cephalosporin compounds.

Important antibiotic compounds according to the invention by virtue of their broad spectrum antibiotic properties coupled with stability of β-lactamase produced by a variety of organisms are compounds of the general formulae

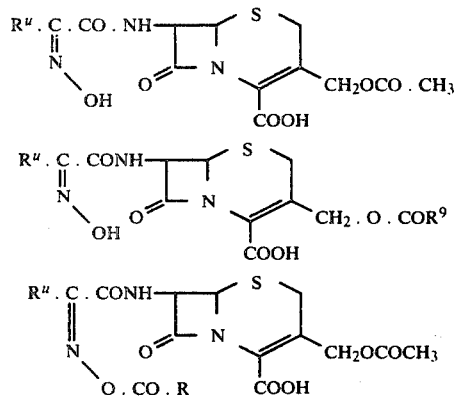

and non-toxic derivatives thereof. In formulae (B) (C) and (D) R$^u$ is phenyl; naphthyl; thienyl; furyl; pyridyl; phenyl, naphthyl, thienyl, furyl or pyridyl substituted by halo, hydroxy, lower alkyl, nitro, amino, loweralkylamino, diloweralkylamino, lower alkanoyl, lower alkanoylamino, lower alkoxy, lower alkythio or carbamoyl; R$^9$ is C$_2$–C$_4$ alkyl or C$_2$–C$_4$ alkenyl; and R is C$_1$–C$_4$ alkyl, C$_1$–C$_4$ chloroalkyl, C$_1$–C$_4$ alkoxy, phenyl, nitrophenyl or C$_1$–C$_4$ chloroalkylamino.

Other important antibiotic compounds according to the invention are those of the general formula

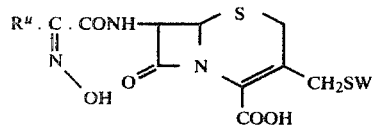

(wherein R$^u$ is as defined under (B), (C) and (D) and W is thiadiazolyl, preferably 5-methyl-1,3,4-thiadiazol-2-yl, diazolyl, triazolyl, tetrazolyl, preferably 1-methyltetrazol-5-yl, thiazolyl, thiatriazolyl, oxazolyl, oxadiazolyl, benzimidazolyl, benzoxazolyl, triazolopyridyl, purinyl, pyridyl or pyrimidyl) and non-toxic derivatives thereof.

Compounds of formula (E) possess a very high degree of activity against a variety of gram positive and gram negative organisms coupled with high stability to β-lactamases produced by a variety of organisms. A further significant property of these compounds is their stability to mammalian esterases.

Other important antibiotic compounds according to the invention are those having the general formula

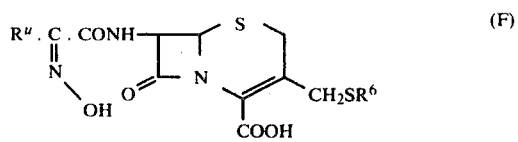

(wherein R$^u$ is as defined above under (B), (C) and (D) and R$^6$ is C$_1$–C$_4$ alkyl) and non-toxic derivatives thereof. These compounds are broad spectrum antibiotics possessing properties of oral absorption. They also have stability to β-lactamases produced by a variety of organisms.

A particularly preferred class of cephalosporin antibiotic compounds according to the invention are those of the formula

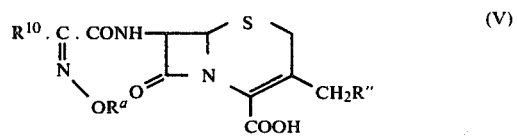

(wherein R$^{10}$ is phenyl, thien-2-yl or fur-2-yl, R$^a$ has the above-defined meaning and is preferably hydrogen and R″ is acetoxy, crotonyloxy, isobutyryloxy, methoxy, 5-methyl-1,3,4-thiadiazol-2-ylthio or 1-methyltetrazol-5-yl thio) and base salts thereof e.g. sodium or potassium salts. Important compounds falling within this class include the following compounds in their syn isomeric form 3-acetoxymethyl-7β-(2-hydroxyimino-2-phenylacetamido)ceph-3-em-4-carboxylic acid;

3-acetoxymethyl-7β-[2-hydroxyimino-2-(thien-2-yl)acetamido]ceph-3-em-4-carboxylic acid;

7β-[2-hydroxyimino-2-(thien-2-yl)acetamido]-3-(5-methyl-1,3,4-thiadiazol-2-ylthiomethyl)ceph-3-em-4-carboxylic acid;

7β-(2-hydroxyimino-2-phenylacetamido)-3-(5-methyl-1,3,4-thiadiazol-2-ylthiomethyl)ceph-3-em-4-carboxylic acid;

7β-[2-hydroxyimino-2-(thien-2-yl)-acetamido]-3-(1-methyltetrazol-5-ylthiomethyl)-ceph-3-em-4-carboxylic acid (syn-isomer);

7β-[2-hydroxyimino-2-(fur-2-yl)acetamido]-3-(1-methyltetrazol-5-ylthiomethyl)-ceph-3-em-4-carboxylic acid;

especially as their sodium or potassium salts.

These six last-mentioned compounds are broad spectrum antibiotics, being active against a wide variety of gram-positive, (penicillin-resistant and penicillin sensitive strains of Staph. aureus) and gram-negative organisms as evidence by in vitro and in vivo tests. Moreover, the compounds are markedly resistant to β-lactamases produced by a variety of gram positive and gram negative organisms.

Preparation

The compounds according to the invention may be prepared by any convenient method. According to one embodiment of the invention we provide a process for the preparation of a compound of the formula

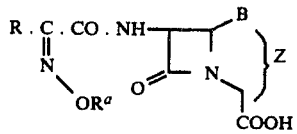

(wherein R is a hydrogen atom or an organic group, $R^a$ is hydrogen or an acyl group, B is >S or >S→O and Z is a group in which 1 or 2 carbon atoms link the nuclear sulphur atom and the carbon atom bearing the carboxyl group) and derivatives thereof, which comprises either (A) condensing a compound of the formula

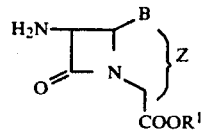

(wherein B and Z have the above defined meanings and $R^1$ is hydrogen or a carboxyl blocking group) with an acylating agent, advantageously the syn isomer, corresponding to the acid

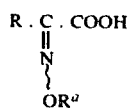

(wherein R and $R^a$ have the above defined meanings) or with an acylating agent corresponding to an acid which is a precursor for the acid (VI) and converting the resulting precursor acyl group into the desired acyl group; or (B) reacting a compound of the formula

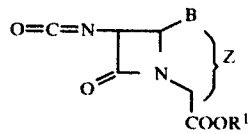

(wherein B, Z and $R^1$ have the above defined meaning except that $R^1$ is not hydrogen) with an acid of formula (VI) wherein $R^a$ is not hydrogen; or (C), where Z is the group

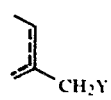

(wherein Y is the residue of a nucleophile or a derivative of the residue of a nucleophile and the dotted line bridging the 2,3 and 4 positions indicates that the compound may be a ceph-2-em or a ceph-3-em compound) reacting a compound of the formula

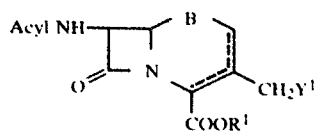

(wherein Acyl is the group

or a precursor therefor; B, $R^a$, $R^1$ and the dotted line have the above meanings and $Y^1$ is a replaceable residue of a nucleophile) with a nucleophile whereafter, if necessary and desired in each instance, any of the following reactions (D) are carried out (i) conversion of a precursor for the desired

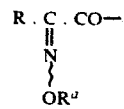

group into that said group (ii) conversion of a $\Delta^2$ isomer into the desired $\Delta^3$ isomer (iii) removal of any carboxyl blocking groups (iv) reduction of a compound in which Z is >S→O to form the desired Z=>S compound (v) reduction of a compound in which Y is azide to form a 3-aminomethyl compound (vi) reaction of a compound in which Y is azide with a depolarophile to form a compound having a polyazole ring linked to the 3-methylene group (vii) deacylation of a compound in which Y is an acyloxy group to form a 3-hydroxymethyl compound and (viii) acylation of a compound in which Y is hydroxy to form a 3-acyloxymethyl compound and, (E) recovering the desired compound of formula (I), if necessary, after separation of isomers.

Salts of the compounds according to the invention may be formed in any convenient way. For example base salts may be formed by reaction of the penicillin or cephalosporin acid with sodium or potassium 2-ethylhexanoate.

In practice it is convenient to condense an acylating agent corresponding to the acid

where R and $R^a$ have the above defined meanings, with an amino compound

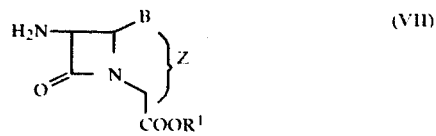

[where Z and B have the above defined meanings and $R^1$ is hydrogen or a carboxyl blocking group e.g. the residue of an ester-forming alcohol (aliphatic or araliphatic), phenol, silano), stannoanol or acid] the condensation, if desired, being effected in the presence of a condensation agent, and being followed, if necessary, by removal of the group $R^1$.

In the case of the preparation of cephalosporin and penicillin compounds the amino compound (VII) may correspond to compounds (II) and (III) above and have the formulae

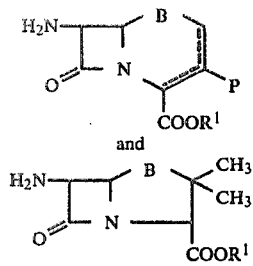

and

respectively, wherein $R^1$, B and P have the above defined meanings. There may also be used a derivative of the amino compounds such as a salt e.g. a tosylate.

Compounds in which $R^a$ is hydrogen may be prepared indirectly and compounds in which $R^a$ is not hydrogen may be prepared directly by employing as the acylating agent an acid halide, particularly an acid chloride or bromide. In the preparation of a compound in which $R^a$ is hydrogen by this technique an additional step will be necessary in which the acyl group $R^a$ is removed to yield the hydroximino compound. The acylation may be effected at temperatures of from $-50°$ to $+50°$ C., preferably from $-20°$ to $+20°$ C. e.g. about $0°$ C. The acylating agent may be prepared by reacting the acid (VI) in which $R^a$ is not hydrogen with a halogenating agent e.g. phosphorus pentachloride, thionyl chloride or oxalyl chloride. The acylation may be effected in aqueous or non-aqueous media and suitable media include an aqueous ketone such as aqueous acetone, an ester e.g. ethyl acetate, or an amide e.g. dimethylacetamide, or a nitrile e.g. acetonitrile, or mixtures thereof.

Acylation with an acid halide may be effected in the presence of an acid binding agent e.g. a tertiary amine (e.g. triethylamine or dimethylaniline), an inorganic base (e.g. calcium carbonate or sodium bicarbonate) or an oxirane, which binds hydrogen halide liberated in the acylation reaction. The oxirane is preferably a lower-1, 2-alkylene oxide e.g. ethylene oxide or propylene oxide.

When using the free acid form of a compound of formula (VI) and, if desired, where $R^a=H$, suitable condensing agents for use in the preparation of the compounds according to the invention include carbodiimides, for example N,N'-diethyl-, dipropyl- or diisopropylcarbodiimide, N,N'-dicyclohexylcarbodiimide, or N-ethyl-N'-γ-dimethylaminopropylcarbodiimide; a suitable carbonyl compound, for example carbonyldiimidazole; or an isoxazolinium salt, for example, N-ethyl-5-phenylisoxazolinium-3'-sulphonate and N-t-butyl-5-methylisoxazolinium perchlorate. The condensation reaction is desirably effected in an anhydrous reaction medium, e.g. methylene chloride, dimethylformamide or acetonitrile, since one may then regulate more precisely reaction parameters such as temperature.

Alternatively, acylation may be effected with other amide-forming derivatives of the free acid such as, for example, a symmetrical anhydride or mixed anhydride, e.g. with pivalic acid or formed with a haloformate, e.g. a lower alkylhaloformate. The mixed or symmetrical anhydrides may be generated in situ. For example, a mixed anhydride may be generated using N-ethoxycarbonyl-2-ethoxy-1, 2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid). Another convenient acylating agent is an activated ester e.g. a compound of the formula $$R.C.CO.W \quad \text{(X)}$$
$$\underset{OR^a}{\overset{\parallel}{N}}$$

where W, is for example, azide, oxysuccinimide, oxybenztriazole, pentachlorophenoxy or p-nitrophenoxy group.

One may prepare compounds according to the invention in which $R^a=H$ by condensing an acylating agent corresponding to the acid (VI) in which $R^a$ is not hydrogen but is a group which can be readily removed to yield the desired group $=N\sim OH$ with the amino compound (VIII). The $R^a$ group is removed subsequently, if desired inconjunction with the removal of the group $R^1$. Illustrative of such readily removable $R^a$ groups are acetyl, if desired having at least one electron-withdrawing group on the α-carbon atom e.g. trichloroacetyl, dichloroacetyl, monochloroacetyl, trifluoroacetyl, difluoroacetyl and monofluoroacetyl; formyl; benzhydryloxycarboxy, benzyloxycarbonyl, t-butoxycarbonyl and 2,2,2-trichloroethoxycarbonyl. The removal of such groups may for example be effected under mildly basic conditions. Thus, for example, an acetyl group may be removed by means of treatment with aqueous alkali. Halogenated acetyl groups may be removed by means of aqueous bicarbonate and, additionally, chloroacetyl can be removed using a nucleophile such as a thiourea. Benzhydryloxycarbonyl and t-butoxycarbonyl groups can be removed using trifluoroacetic acid with or without anisole. 2,2,2-Trichloroethoxycarbonyl may be removed by means of a reducing agent such as zinc/acetic acid or zinc/formic acid. It will be appreciated that although the preparation of compounds having readily removable $R^a$ groups affords a convenient route to hydroxyimino compounds, compounds with such $R^a$ groups are also compounds according to the invention and may possess desirable properties in their own right.

Alternatively the compound of formula (I) may be prepared from a compound of formula

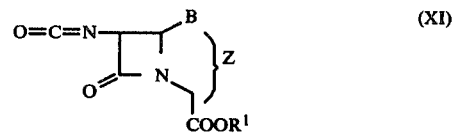

where B, Z and $R^1$ have the above defined meanings (except $R^1=H$) by reaction with an acid of formula (VI) (except where $R^a=H$) and subsequently removing the groups $R^1$ and, if desired, $R^a$ (see for example Dutch Patent Application No. 6808622 and Belgian Patent No. 760494).

The reaction of the compound of formula (VII) or (XI) may be carried out towards the end of the preparative sequence, the only additional reactions being deprotection reactions and purifications.

Compounds of formula I where $R^a$=acyl may be obtained from the corresponding compounds of formula I where $R^a=H$ or from esters thereof (i.e. having at the 4-position a group $COOR^1$, $R^1$ having the above defined meaning) by acylation. Acylation may be effected in any convenient manner e.g. using an acid halide, symmetrical or mixed anhydride, ketene, acyl azide or carbodiimide (when the 4-carboxy group is protected) corresponding to the acid $R^aOH$. Alternatively the acylation may be effected by means of a haloformate for example a chloroformate such as ethylchlorformate whereupon one will obtain carbonates or by means of an isocyanate $R^6NCO$ for example 2-chloroethyl isocyanate whereupon one will obtain carbonates in which $OR^a$ has the formula $R^bNHCO.O-$ where $R^b$ has the above defined meaning. The acylation may be catlysed e.g. by a base such as triethylamine, diethylaniline, pyridine, propylene oxide, magnesium oxide, sodium carbonate or calcium carbonate. The acylation may be effected in an organic solvent. Suitable solvents include halogenated hydrocarbons e.g. methylene chloride; cyclic ethers e.g. dioxan or tetrahydrofuran; nitriles e.g. acetonitrile; nitrohydrocarbons e.g. nitromethane; esters e.g. ethyl acetate; or the acylating agent itself. The acylation may be effected at a temperature of $-10°$ to $+100°$ C., preferably $0°$ to $50°$ C. advantageously $0°$ to $30°$ C. After the acylation has been effected the group $R^1$ is removed, if necessary.

If desired, one can first prepare a compound of formula

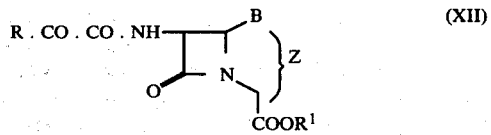
(XII)

(where R, $R^1$, B and Z have the above defined meanings) and then effect reaction of the compound of formula (XII) with $R^aO.NH_2$ ($R^a$ having the above defined meaning), followed, if ncessary by removal of the group $R^1$. The reaction product may be separated into syn and anti isomers before or after removal of $R^1$.

One may prepare compounds of formula (I) wherein R is an activating group such as cyano or pyridyl by a technique involving nitrosation. Thus a compound possessing the acylamido group

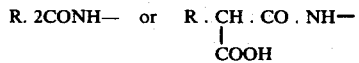

may be nitrosated using, for example, nitrous acid (which may be prepared in situ by reaction of an alkali metal nitrite with a weak acid e.g. acetic acid), nitrosyl chloride, or an organic nitrosating agent e.g. an alkyl, cycloalkyl, aryl or aralkyl nitrite. In the case of rnitrosation of a compound containing the group

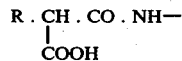

concomitant decarboxylation will occur. Separation of syn and anti-isomers may be necessary after the nitrosation reaction.

If desired the replacement of one P group by another and preferred P group may be carried out after acylation of the 7-amino compound has taken place. In particular when P is the group

where Y has the above defined meaning the Y group may be introduced by methods described in the literature. Thus compounds in which Y is a halogen atom, an ether group, or a thioether group may be prepared as described in Belgian Patents Nos. 719,711; 719,710; 734,532 and 734,533. Compounds wherein Y is the residue of a nucleophile may also be prepared by the reaction of a 3-acetoxymethyl cephalosporin compound with a nucleophile, for example, pyridine or other tertiary amine as described in British Patent No. 912,541; a sulphur-linking, nitrogen-linking or inorganic nucleophile as described in British Patent No. 1,012,943; a sulphur-linking nucleophile as described in British Patents Nos. 1,059,562, 1,101,423 and 1,206,305; or a nitrogen-linking nucleophile as described in British Patents Nos. 1,030,630, 1,082,943 and 1,082,962.

Compounds in which Y is a derivative of a residue of a nucleophile such as an amino or acylamido group derived from an azido group and compounds in which Y is azido and is reacted with a dipoloarophile may be prepared as described in British Patents Nos. 1,057,883 and 1,211,694. Compounds of the invention wherein Y is the residue of a nucleophilic may also be prepared by the reaction of a 3-halomethyl-cephalosporin with any of the nucleophiles disclosed in the above references, such a process being described in Belgian Patent No. 719,711. Where Y is a hydroxy group the compound may be prepared by the methods described in British Patent No. 1,121,308.

Compounds having a vinyl or substituted vinyl group as 3-position substituent may be obtained by the method described in Belgian Patent No. 761,897.

Where Y is a halogen (i.e. chlorine, bromine or iodine) ceph-3-em starting compounds may be prepared by halogenation of a 7β-acylamido-3-methylceph-3-em-4-carboxylic acid ester 1β-oxide followed by reduction of the 1β-oxide group later in the sequence as described in Belgian Patent No. 755,256.

The corresponding ceph-2-em compounds may be prepared by the method of Dutch published Patent Application No. 6902013 by reaction of a ceph-2-em-3-methyl compound with N-bromo-succinimide to yield the ceph-2-em-3-bromomethyl compound.

Where Y is a hydrogen atom the compound may be prepared by the method described in British Patent No. 957,569 or from a penicillin compound by the method described in U.S. Pat. No. 3,275,626 and Belgian Patents Nos. 747,119 and 747,120.

Cephalosporin compounds possessing an acyloxymethyl group as 3-position substituent may be prepared by any convenient method e.g. they may be prepared from a cephalosporin having a $3-CH_2Y$ group where $Y=OH$ or the residue of the acid H Y which has a pKa of not more than 4.0 and preferably not more than 3.5 (as measured in water at $25°$ C.).

The group Y may be a chlorine, bromine or iodine atom, formyloxy or an acetoxy group having at least one electronwithdrawing substituent on the α-carbon atom or a nuclear substituted benzoyloxy group, the nuclear substituent being of the electron withdrawing type as described in British Patent No. 1,241,657 and the nucleophilic displacement reaction to introduce the desired 3-position substituent may be carried out as described in our aforesaid British Patent No. 1,241,657.

Alternatively where Y is hydroxy the desired 3-acyloxymethyl cephalosporin may be obtained by acylation as described in British Patent No. 1,141,293. In British Patent No. 1,141,293 there is described a process for the preparation of a $\Delta^3$-cephalosporin having a 3-acyloxymethyl substituent from a corresponding 3-hydroxymethyl analogue which comprises aralkylating the 4-carboxy group, acylating the 3-hydroxymethyl group of the protected compound and subsequently removing the aralkyl group.

The acylation may be carried out by any convenient method using for example an acid chloride, acid anhydride or a mixed acid anhydride as the acylating agent preferably in the presence of an organic base such as pyridine and carrying out the reaction in solution in an inert anhydrous solvent for example methylene chloride. Alternatively the acylation may be carried out in aqueous acetone/sodium bicarbonate solution. The preferred acylating agent is the acid chloride.

The acylation reaction should be effected as rapidly as possible, since under the conditions of the acylation rearrangement to the $\Delta^2$-derivative can occur, particularly when an aroyloxy group is being introduced at the exocyclic methylene group at the 3-position.

Compounds of the formula (VII) may be employed as esters; those of formula (XI) are esters. One may also use the free amino acid or an acid addition salt of the free amino acid or ester thereof. Salts which may be used include acid addition salts e.g. with hydrochloric, hydrobromic, sulphuric, nitric, phosphoric, toluene-p-sulphonic and methane sulphonic acids.

The ester may be formed with an alcohol, phenol, silanol or stannanol having up to 20 carbon atoms which may readily be split off at a later stage of the overall reaction.

Any esterifying group substituting the 4-carboxyl group of a compound of formula (VII), (XI) or (XII) is preferably formed with an alcohol (aliphatic or aralphatic), phenol, silanol, stannanol or acid which may readily be split off at a later stage of the reaction.

Suitable esters thus include compounds containing as ester group a group selected from the following list which is not intended to be an exhaustive list of possible ester groups.

(i) —$COOCR^aR^bR^c$ wherein at least one of $R^a$, $R^b$ and $R^c$ is an electron-donor e.g. p-methoxyphenyl, 2,4,6-trimethylphenyl, 9-anthryl, methoxy, acetoxy, or fur-2yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxy carbonyl.

(ii) —$COOCR^aR^bR^c$ wherein at least one of $R^a$, $R^b$ and $R^c$ is an electron-attracting group e.g. benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. The remaining $R^a$, $R^b$, and $R^c$ groups may be hydrogen or organic substituting groups. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) —$COOCR^aR^bR^c$ wherein at least two of $R^a$, $R^b$ and $R^c$ are hydrocarbon such as alkyl e.g. methyl or ethyl, or aryl e.g. phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) —$COOR^d$ wherein $R^d$ is adamantyl, 2-benzyloxyphenyl, 4-methylthiophenyl, tetrahydrofur-2-yl or tetrahydropyran-2-yl.

(v) Silyloxycarbonyl groups obtained by reaction of a carboxyl group with a derivative of a silanol. The derivative of a silanol is conveniently a halosilane or a silazane of the formula $R^4{}_3SiX$; $R^4{}_2SiX_2$; $R^4{}_3Si.NR^4{}_2$; $R^4{}_3Si.NH.SiR^4{}_3$; $R^4{}_3Si.NH.COR^4$; $R^4{}_3Si.NH.CO.NH.SiR^4{}_3$; $R^4NH.CO.NR^4.SiR^4{}_3$; or $R^4C(OSiR^4{}_3)$: $NSiR^4{}_3$ where X is a halogen and the various groups $R^4$, which can be the same or different, represent hydrogen atoms or alkyl, e.g. methyl, ethyl, n-propyl, iso-propyl; aryl, e.g. phenyl; or aralkyl e.g. benzyl groups. Preferred derivatives of silanols are silyl chlorides such as for example trimethylchlorosilane and dimethyldichlorosilane.

The carboxyl group may be regenerated from an ester by any of the usual methods, for example, acid- and basecatalysed hydrolysis is generally applicable, as well as enzymically-catalysed hydrolyses; however, aqueous mixtures may be poor solvents for these compounds and they may cause isomerizations, rearrangements, sidereactions, and general destruction, so that special methods may be desirable.

Five suitable methods of deesterification are (1) Reactions with Lewis acids.

Suitable Lewis acids for reaction with the esters include trifluoroacetic acid, formic acid, hydrochloric acid in acetic acid, zinc bromide in benzene and aqueous solutions or suspensions of mercuric compounds. The reaction with the Lewis acid may be facilitated by addition of a nucleophile such as anisole.

(2) Reduction.

Suitable systems for effecting reduction are zinc/acetic acid, zinc/formic acid, zinc/lower alcohol, zinc/pyridine, palladised-charcoal and hydrogen, and sodium and liquid ammonia.

(3) Attack by nucleophiles.

Suitable nucleophiles are those containing a nucleophilic oxygen or sulphur atom for example alcohols, mercaptans and water.

(4) Oxidative methods, for example, those which involve the use of hydrogen peroxide and acetic acid.

(5) Irradiation.

Where at the end of a given preparative sequence compounds are obtained wherein B is $>S\to O$ and a compound is desired in which B is $>S$ conversion to a sulphide may for example, be effected by reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Alternatively, reduction of the 1-sulphinyl group may be effected by phosphorus trichloride or tribromide in solvents such as methylene chloride, dimethylformamide or tetrahydrofuran, preferably at a temperature of $-20°$ C. to $+50°$ C.

Where the resultant compound is a ceph-2-em-4-ester the desired ceph-3-em compound may be obtained by treatment of the former with a base.

The acid (VI) to which the acylating agent corresponds may be obtained by reacting the glyoxylic acid.

R.CO.COOH (where R has the above defined meaning) or an ester thereof with $R^aO.NH_2$ ($R^a$ having the above defined meaning).

The resulting acid or ester may then be separated into its syn and anti isomers e.g. by crystallisation, chromatography or distillation, followed when necessary by hydrolysis of the ester.

Alternatively the acid (VI) where $R^a=H$ may be obtained by reacting an ester of the acid

R.CH$_2$COOH (where R has the above defined meaning) with an inorganic or organic nitrosating agent e.g. an alkyl nitrite such as isopropyl nitrite, or nitrosyl chloride in the presence of an acid or base. We prefer that an excess of the nitrosating agent be used e.g. a molar excess. Thereafter the ester group is removed, if necessary.

Syn and anti isomers may be distinguished by appropriate techniques, e.g. by their ultraviolet spectra, by thin layer or paper chromatography or by their nuclear magnetic resonance spectra. For example, for DMSO-d$_6$ solution compounds of Formula I exhibit the doublet for the amide NH at a lower field for the syn-isomers than for the anti-isomers). These factors may be employed in monitoring reactions.

The antibacterial compounds according to the invention may be formulated for administration in any convenient way, by analogy with other antibiotics and the invention therefore includes within its scope a pharmaceutical composition comprising an antibacterial compound of formula I or a non-toxic derivative e.g. salt thereof (as herein defined) adopted for use in human or veterinary medicine. Such compositions may be presented for use in conventional manner with the aid of any necessary pharmaceutical carriers or excipient.

The antibacterial compounds according to the invention may be formulated for injection and may be presented in unit dose form in ampoules, or in multidose containers with an added preservative. The compositions may take such forms as suspensions, solutions, emulsions in oily or aqueous vehiclels, and may contain formulatory agents such as suspending, stabilising and-/or dispersing agents. Alternatively the active ingredient may be in powder form for reconstitution with a suitable vehicle, e.g. sterile, pyrogen-free water, before use.

The compositions may be presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinyl-pyrollidone; fillers, for example lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium sulphate. The tablets may be coated according to methods well known in the art. Oral liquid preparation may be in the form of aqueous or oily suspensions, solutions, emulsions, syrups, elixirs, etc. or may be presented as a dry product, for reconstitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats, emulsifying agents, for example, lecithin, sorbitan monooleate or acacia; non-aqueous vehicles which may include edible oils, for example, almond oil, fractionated coconut oil, oily esters, propylene glycol, or ethyl alcohol; preservatives, for example, methyl or propyl p-hydroxybenzoates or sorbic acid. Suppositories will contain conventional suppository bases, e.g. cocoa butter or other glyceride.

The composition may also be prepared in suitable forms for absorption through the mucous membranes of the nose and throat or bronchial tissues and may conveniently take the form of powder or liquid sprays or inhalants, lozenges, throat paints etc. For medication of the eyes or ears, the preparations may be presented as individual capsules, in liquid or semi-liquid form, or may be used as drops etc. Topical applications may be formulated in hydrophobic or hydrophilic bases as ointments, creams, lotions, paints, powders etc.

For veterinary medicine the composition, may, for example, be formulated as an intramammary preparation in either long acting or quick-release bases.

The compositions may contain from 0.1% upwards, preferably from 10–60% of the active material, depending on the method of administration. Where the compositions comprise dosage units, each unit will preferably contain 60–500 mg. of the active ingredient. The dosage as employed for adult human treatment will preferably range from 100–3000 mg. for instance 1500 mg per day, depending on the route and frequency of administration.

The compounds according to the invention may be administered in combination with other therapeutic agents such as antibiotics, for example other cephalosporins, the penicillins or tetracyclines.

The following examples illustrate the invention.

2-HYDROXYIMINO-ACETIC ACIDS AND DERIVATIVES

PREPARATION 1

2-Hydroxyimino(thien-2-yl)acetic acid (syn-isomer)

A cooled solution of hydroxylamine hydrochloride (0.884 g) and sodium bicarbonate (1.08 g) in water (20 ml.) was added to a cooled (0°) solution of thien-2-yl-glyoxylic acid (2.0 g) and sodium bicarbonate (1.08 g) in water (20 ml.). After two days at 20° the solution was extracted with ether, cooled and acidified with concentrated hydrochloric acid. The resulting white solid was filtered off (0.564 g) and the filtrate was then thoroughly extracted with ether. The combined extracts were washed with brine, dried and concentrated. The solid residue was triturated with benzene to give the oxime (syn-isomer) (1.05 g; 51%), m.p. 132°, $\lambda_{max.}$ (ethanol) 284 nm ($\epsilon$ 9,500), $\lambda_{max.}$ (Nujol) 2590 and 1706 (CO$_2$H) and 1655 cm$^{-1}$ (C=N), $\tau$ (DMSO-d6), −2.5 to −0.5 (broad multiplet; N—OH and COOH), 2.36 (multiplet; thienyl C-5 H) and 2.82 (multiplet; thienyl C-3 H and C-4 H).

PREPARATION 2

2-Dichloroacetoxyiminophenylacetic acid (syn-isomer).

To a mixture of methylene chloride (45 ml) and dichloroacetyl chloride (10 ml) was added portionwise with stirring 2-hydroxyiminophenylacetic acid (syn-isomer) (5 g) in portions over about fifteen minutes. The reaction mixture became solid, and was stirred for one hour at room temperature after the addition was complete. The reaction was diluted with petroleum (b.p.

40°–60°), filtered, and the solid washed several times with petroleum spirit to remove residual acid chloride. The solid was dried under vacuum, giving 2-dichloroacetoxyiminophenylacetic acid (syn-isomer)(8.0 g; 96%), m.p. 115°, $\nu_{max}$ (CHBr$_3$) 3470 and 1750 (—CO$_2$H), 1765 cm.$^{-1}$ (ester), $\tau$ (CDCl$_3$) values include 2.0–2.7 (multiplet; aromatic protons), 3.85 (singlet; —CHCl$_2$).

PREPARATION 3

2-Dichloroacetoxyimino-(thien-2-yl)acetic acid (syn-isomer)

2-Hydroxyimino-(thien-2-yl)acetic acid (syn-isomer) (38 g.) was added portionwise to a stirred solution of dichloroacetyl chloride (70 ml.) in dry methylene chloride (350 ml.) at 20°. Stirring was continued and after ca. 20 mins. white fibrous crystals formed. The suspension was stirred for 10 mins. longer and then filtered. The solid was washed with methylene chloride and petroleum to give the title acid (38.5 g., 61%) $\lambda_{max}$ (EtOH) 262.5 ($\epsilon$ 9,520), 291 nm ($\epsilon$ 8,580).

PREPARATION 4

2-Dichloroacetoxyimino-(4-chlorophenyl)acetic acid (syn-isomer)

To a solution of dichloroacetyl chloride (1.8 ml.) in methylene chloride (15 ml.) was added 2-hydroxyimino-(4-chlorophenyl)acetic acid (anti-isomer) (1.5 g.) and the suspension stirred for two hours at room temperature. During this time most of the material dissolved. The solid was removed, washed with petroleum (b.p. 40°–60°) and the washings and filtrate were combined, kept at 5° overnight and the resulting solid was collected and dried to give the title acid (2.0 g; 85%), m.p. 80°, $\lambda_{max}$ (EtOH) 258 nm ($\epsilon$ 12,280), $\lambda_{max}$ (Nujol) 1774 (ester), 1750 and 1722 cm.$^{-1}$ (CO$_2$H).

PREPARATION 5

2-Dichloroacetoxyiminonaphth-1'-ylacetyl chloride (syn-isomer)

To a solution of 2-hydroxyiminonaphth-1'-ylacetic acid (syn-isomer) (0.375 g) in ethyl acetate (10 ml.) at 0° was added dichloroacetyl chloride (0.2 ml.) and the solution was stirred for thirty minutes at 0°. After the addition of phosphorus pentachloride (0.36 g.), the mixture was stirred for ninety minutes at 0°. The solvent was evaporated at a low temperature (ca. 5°) and toluene evaporated from the residue, at ca. 5°. The remaining oil was dissolved in ethyl acetate (5 ml.) and used without further purification.

PREPARATION 6

2-Dichloroacetoxyiminophenylacetyl chloride (syn-isomer)

To a suspension of 2-dichloroacetoxyiminophenylacetic acid (syn-isomer) (0.276 g) in methylene chloride (10 ml.) was added phosphorus pentachloride (0.208 g) and the mixture was stirred for one hour at room temperature, during which time solution took place. After removal of solvent under reduced pressure, benzene was evaporated from the residue, and the resulting oil freed from solvent under vacuum, giving 2-dichloroacetoxyiminophenylacetyl chloride (syn-isomer) (0.29 g., 100%), $\nu_{max}$ (liquid film) 1770 cm.$^{-1}$ (COCl and CO$_2$R).

PREPARATION 7

2-Dichloroacetoxyimino-(thien-2-yl)acetyl chloride (syn-isomer)

A 0.3 M solution of phosphorus pentachloride in methylene chloride (179 ml.) was added dropwise during 15 minutes to a stirred and cooled (0°) suspension of syn-2-hydroxyiminothien-2-ylacetic acid (16.7 g.) in dry methylene chloride (340 ml.). After 5 minutes the solution was concentrated under reduced pressure and at low temperature. The red residual oil was azeotroped with benzene, dissolved in ethyl acetate and used without further purification.

PREPARATION 8

2-Hydroxyiminonaphth-1'-ylacetic acid (syn and anti-isomers)

To a solution of hydroxylamine hydrochloride (4.62 g.) in methanol (40 ml.) was added phenolphthalein then methanolic sodium methoxide solution (approx. 5% w/v) until a pink end-point was reached. A crystal of hydroxylamine hydrochloride was added to discharge the pink colour, and the solution was filtered to remove sodium chloride. Naphth-1'-ylglyoxylic acid (10.0 g) was added and the mixture heated at reflux for thirty minutes. It was then evaporated to dryness, water (50 ml.) added, and the pH adjusted to 1 with 2 N-hydrochloric acid. The resulting suspension was extracted with ethyl acetate, the combined extracts washed with water, dried and evaporated to give a pale yellow solid which was recrystallised from benzene-petroleum (b.p. 60°–80°) to give 2-hydroxyiminonaph-1'-ylacetic acid (anti-isomer) (2.7 g; 25%), m.p. 159°, $\lambda_{max}$ (EtOH) 279 nm ($\epsilon$ 5,940) $\nu_{max}$ (Nujol) 3245 (OH), 1701, 1712 cm.$^{-1}$ (CO$_2$H) $\tau$ (DMSO-d6) −3.0 to −2.2 (broad signal; OH) 1.8–2.7 (multiplet; aromatic protons).

The mother liquor from the recrystallisation was evaporated to dryness, the solid (2.2 g.) was treated with a slight excess of ethereal diazomethane and the yellow colouration discharged by addition of the crude 2-hydroxyiminonaph-1'-ylacetic acid. The ethereal solution was washed with saturated sodium bicarbonate solution, dried and evaporated to give a mixture of syn- and anti-methyl 2-hydroxyiminonaphth-1'-yl acetates (2.3 g.) The mixture (2.0 g) was dissolved in ethyl acetate and applied to eight Merck silica gel chromatoplates (20 cm × 20 cm.). The plates were developed with ether:petroleum (b.p. 40°–60°) (1:2) and the major component, which had the higher R$_f$, was eluted with ethyl acetate, giving methyl 2-hydroxyiminonaphth-1'-yl acetate (syn-isomer) (0.75 g; 34%) m.p. 110°–111°, $\lambda_{max}$ (EtOH) 293.5 nm ($\epsilon$ 8150), $\nu_{max}$ (CHBr$_3$) 3550 (OH) and 1737 cm.$^{-1}$ (ester), $\tau$ (CDCl$_3$) values include 1.9–2.85 (multiplet; aromatic protons), 6.16 (singlet; CH$_3$). A solution of the ester (1.10 g.) in N-sodium hydroxide (15 ml.) was allowed to stand for one hour, then washed with ether, acidified (2 N-hydrochloric acid) and extracted with ethyl acetate. The combined extracts were washed with water, dried, and evaporated to give a solid which was triturated with petroleum spirit (b.p. 40°–60°), filtered and dried, giving the title acid (syn-isomer) (0.89 g, 86%), m.p. 111°–112°, $\lambda_{max}$ (EtOH) 292 nm ($\epsilon$ 7,400), $\nu_{max}$ (Nujol) 2630 (OH), 1678 (CO$_2$H).

PREPARATION 9

Ethyl thien-3-yl glyoxylate

To a solution of n-butyl lithium in ether (265 ml.) at −70° was added, with vigorous stirring, a solution of 3-bromothiophene (41 g.) in ether (50 ml) dropwise over 30 minutes, in an atmosphere of nitrogen. The resulting slurry was stirred at −70° for 5 minutes, then added with vigorous stirring to a solution of diethyl oxalate (110 g) in ether (220 ml.), the temperature being maintained below −70° throughout the addition. After the addition, the temperature of the solution was allowed to rise to room temperature and the reaction was stirred for three hours and then poured into 2 N-hydrochloric acid. The organic phase was separated and was combined with two ethereal extracts of the aqueous phase. The combined extracts were dried and evaporated to give an oil which was fractionated under reduced pressure. After distillation of excess diethyl oxalate at 6370.1 mm, the title ester was collected, b.p. 110°/0.1 mm. (12 g; 26%), $\nu_{max}$ 1720 cm$^{-1}$ (ester) $\tau$ (CDCl$_3$) 1.43, 2.28, 2.61, (thienyl protons), 5.56 (quartet J 8 Hz; $\underline{CH_2}$CH$_3$), 8.58 (triplet; J 8 Hz; CH$_2\underline{CH_3}$).

PREPARATION 10

Thien-3-yl-glyoxylic acid

To a mixture of ethyl thien-3-yl-glyoxylate (10 g) and 2 N-sodium hydroxide (50 ml) was added sufficient methanol to produce a homogeneous solution, and the reaction was allowed to stand at room temperature for one hour. The solution was poured into water, extracted with ether, acidified with 2 N-hydrochloric acid and extracted with ether. The combined extracts were dried and evaporated to give an oil which was triturated with benzene-petroleum ether, and the resulting solid filtered and dried (7.5 g; 88%), m.p. 63°, $\nu_{max}$ (Nujol) 3600 and 1702 cm$^{-1}$ (CO$_2$H), $\tau$ (DMSO-d$_6$) values include 1.29, 2.21, 2.38 (thien-3-yl protons).

PREPARATION 11

2-Hydroxyimino-2(thien-3-yl)-acetic acids

To a stirred solution of hydroxylamine hydrochloride (1.15 g) in methanol (15 mls) containing phenolphthalein (2 drops) was added a solution of sodium methoxide in methanol until a pink colour was obtained. After the addition of one crystal of hydroxylamine hydrochloride to discharge the pink colour the mixture was added to a solution of thien-3-yl-glyoxylic acid (2.0 g) in methanol (10 mls) and refluxed for 1 hr. The methanol was evaporated to a small volume and the residue was partitioned between ethyl acetate and water. The aqueous layer was acidified to pH 1 with 2 N-hydrochloric acid and extracted with ethyl acetate. After drying, the ethyl acetate was evaporated to yield a white solid consisting of isomeric 2-hydroxyimino-2-(thien-3-yl) acetic acids, $\lambda_{max}$ (ethanol) 254.5 mm ($\epsilon$ 9,700), $\nu_{max}$ (CHBr$_3$) 3540 (OH unbonded), 3200 (OH bonded) and 1750 cm.$^{-1}$ (COOH) $\tau$ (DMSOd$_6$) values include 1.78 [multiplet; thienyl protons (anti isomer)], 2.2 to 2.7 (complex multiplet; thienyl protons).

PREPARATION 12

2-Dichloroacetoxyimino-2-(thien-3-yl)acetyl chloride (syn isomer)

2-Hydroxyimino-2-(thien-3-yl)acetic (1.03 g) mixture was added portionwise to a stirred solution of dichloroacetyl chloride (1.8 mls) in dry methylene chloride (10 mls). After 30 mins. an excess of petrol (b.p. 40°–60°) was added to the reaction and the precipitated white solid was collected, washed with petrol (b.p. 40°–60°) and dried to yield 2-dichloroacetoxyimino-2-(thien-3-yl)acetic acid (syn isomer) (1.6 gms, 94%) which was suspended in dry methylene chloride and ice-cooled. To the suspension was added dropwise a freshly prepared solution of phosphorus pentachloride (1 equiv.) in dry methylene chloride. When all components were in solution the solvent was removed in vacuo at low temperature and the residual oil was azeotroped with benzene to give 2-dichloroacetoxyimino-2-(thien-3-yl)acetyl chloride (syn) as a pale yellow oil which was used directly.

PREPARATION 13

2-Hydroxyimino-2-(fur-2-yl)acetic acids

To a stirred solution of hydroxylamine hydrochloride (1.94 gms) in methanol (30 mls) containing phenolphthalein (2 drops) was added a solution of sodium methoxide in methanol until a pink colour was obtained. After the addition of one crystal of hydroxylamine hydrochloride to discharge the pink colour the mixture was added to a solution of fur-2-ylglyoxylic acid (3.0 gm) in methanol (10 mls) and refluxed for 1 hr. The methanol was evaporated to a small volume and partitioned between ethyl acetate and water. The aqueous layer was acidified to pH 1 with 2 N-hydrochloric acid and extracted with ethyl acetate. After drying, the solvent was evaporated to yield a yellow solid which was collected, washed with petrol (b.p. 40°–60°) and dried to yield an isomeric mixture of 2-hydroxyimino-2-(fur-2-yl)acetic acids (2.7 gms., 81%) $\lambda_{max}$ (ethanol) 271.5 nm ($\epsilon$, 12,400), $\nu_{max}$ (CHBr$_3$) 3550 (OH), 1740 and 1705 cm.$^{-1}$ (CO$_2$H), $\tau$ (DMSO d$_6$) values include 2.62 [doublet; J 4 Hz, furyl(anti isomer) C 3-H], 2.14 and 3.32 (complex signals, remaining furyl protons).

PREPARATION 14

2-Dichloroacetoxyimino-2-(fur-2-yl)acetyl chloride (syn)

2-Hydroxyimino-2-(fur-2-yl)acetic acid (1.38 g) mixture was added portionwise to an ice cold solution of dichloroacetyl chloride (2.8 mls.) in dry methylene chloride (14 mls.). After 15 mins stirring a white precipitate was formed which was collected, washed successively with cold dry methylene chloride and petrol (b.p. 40°–60°) and dried to yield 2-dichloroacetoxyimino-2-(fur-2-yl)acetic acid (syn isomer) (1.5 g, 63%).

To an ice-cold stirred suspension of 2-dichloroacetoxyimino-2-(fur-2-yl)acetic acid (1.5 g) in dry methylene chloride (70 mls) was added dropwise a freshly prepared solution of phosphorus pentachloride (1.0 equiv.) in methylene chloride. When solution was complete the solvent was evaporated at low temperature and the residual oil azeotroped with benzene to give 2-dichloroacetoxyimino-2(fur-2-yl)acetyl chloride (syn-isomer) as a pale yellow oil which was used directly.

EXAMPLE 1

(a) t-Butyl 3-acetoxymethyl-7β-[2-hydroxyimino-2-phenylacetamido]-ceph-3-cm-4-carboxylate (syn-isomer).

To a solution of t-butyl 3-acetoxymethyl-7β-aminoceph-3-em-4-carboxylate (3.28 g) and dicyclohexylcarbodiimide (2.48 g) in methylene chloride (60 ml.) and dimethylformamide (20 ml.) was added, dropwise with stirring at room temperature, a solution of 2-hydroxyiminophenylacetic acid (syn-isomer)(Ahmad and Spencer, Can J. Chem, 1961, 39, 1340) (1.65 g) in dimethyl formamide (20 ml.) and the mixture was stirred at room temperature for 3 hours. After filtration to remove dicyclohexylurea, the solution was evaporated, the residue taken up in ether (50 ml.), filtered and washed successively with saturated sodium bicarbonate solution, 2 N-hydrochloric acid and water. The extract was dried and evaporated to give the title ester as a foam which was dried under vacuum. Yield 1.6 g; 33.8%, $\nu_{max.}$ (CHBr$_3$) 3570 (OH), 1786 ($\beta$-lactam) 1740 and 1230 cm.$^{-1}$ (OAc), $\tau$ (CDCl$_3$) values include 2.2–2.7 (multiplet; aromatic protons), 7.93 (singlet; CH$_3$CO), 8.46 (singlet; t-butyl ester).

(b) 3-Acetoxymethyl-7$\beta$-[2-hydroxyimino-2-phenylacetamido]ceph-3-em-4-carboxylic acid (syn-isomer).

A solution of t-butyl 3-acetoxymethyl-7$\beta$-[2-hydroxyimino-2-phenylacetamido]-ceph-3-em-4-carboxylate (syn-isomer) (1.45 g.) in trifluoroacetic acid (25 ml.) was allowed to stand at room temperature for 10 minutes. The trifluoroacetic acid was evaporated under reduced pressure, the residue dissolved in ether (50 ml.) and extracted with saturated aqueous sodium bicarbonate. The combined aqueous extracts were acidified (2 N hydrochloric acid) and extracted with ethyl acetate. The combined extracts were washed with water, dried and evaporated. The residue was redissolved in ethyl acetate (5 ml.) and added dropwise with stirring to petroleum (b.p. 40°–60° C.; 500 ml.). The precipitated solid was filtered and dried, giving 3-acetoxymethyl-7$\beta$-[2-hydroxyimino-2-phenylacetamido]-ceph-3-em-4-carboxylic acid (syn-isomer) (0.515 g; 42%), $[\alpha]_D$+56° (c 0.5, DMSO), $\lambda_{max.}$ (EtOH) 253 nm ($\epsilon$ 16,600), $\nu_{max.}$ (Nujol) 3380 (NH and OH), 1778 ($\beta$-lactam), 1720 (CO$_2$H and acetate), 1666 and 1540 cm.$^{-1}$ (CONH) $\tau$ (DMSO-d$_6$) values include 0.32 (doublet, J 9 Hz; NH) 2.15–2.7 (multiplet; aromatic protons), 7.8 (singlet; CH$_3$CO).

(c) Sodium 3-Acetoxymethyl-7$\beta$-(2-hydroxyimino-2-phenylacetamido)-ceph-3-em-4-carboxylate (syn isomer)

To a solution of 3-acetoxymethyl-7$\beta$-(2-hydroxyimino-2-phenylacetamido)ceph-3-em-4-carboxylic acid ethyl acetate solvate (syn-isomer) (0.5 g.) in ethyl acetate (50 ml.) was added sodium 2-ethyl hexanoate (1-M solution in ethyl acetate, 1 ml.). After stirring for fifteen minutes at room temperature the solid was collected by filtration, washed with ethyl acetate and ether and dried to give the title sodium salt (0.35 g; 82%) $[\alpha]_D$+98° (c 1 DMSO), $\lambda_{max.}$ (pH 6.0 phosphate buffer) 253.5 nm ($\epsilon$ 18,400), $\nu_{max.}$ (Nujol) 3280 (NH and OH), 1765 ($\beta$-lactam), 1740 (OCOCH$_3$), 1670 and 1550 cm.$^{-1}$ (CONH), $\tau$ values include (DMSO-d$_6$) 0.24 (singlet, J 9 Hz; NH), 2.28–2.72 (aromatic protons) 7.99 (singlet, OCOCH$_3$).

EXAMPLE 2

(a) t-Butyl 3-acetoxymethyl-7$\beta$-(2-dichloroacetoxyimino-2-phenylacetamido)-ceph-3-em-4-carboxylate (syn-isomer)

To a solution of t-butyl 3-acetoxymethyl-7$\beta$-aminoceph-3-em-4-carboxylate (3.28 g) in ethyl acetate (25 ml.) was added a solution of 2-dichloroacetoxyimino-2-phenylacetyl chloride (syn-isomer) in ethyl acetate (25 ml.) dropwise with stirring. The solution became warm and a precipitate formed. After two hours, the solution was filtered, washed successively with 2 N-hydrochloric acid, water, and saturated sodium bicarbonate solution, dried, and evaporated to give a yellow foam which solidified on standing, and was triturated with petroleum spirit giving t-butyl 3-acetoxymethyl-7$\beta$-(2-dichloroacetoxyimino-2-phenylacetamido)-ceph-3-em-4-carboxylate (4.0 g; 70%), $\nu_{max.}$ (CHBr$_3$) 3420 (NH), 1796 ($\beta$-lactam), 1730 and 1230 (acetate), 1700 and 1512 cm$^{-1}$ (CONH), $\tau$ (DMSO-d$_6$) values include 2.1–2.5 (multiplet; aromatic protons), 2.98 (singlet; CHCl$_2$), 7.6 (singlet; CH$_3$CO), 8.5 (singlet; t-butyl ester).

(b) 3-Acetoxymethyl-7$\beta$-(2-hydroxyimino-2-phenylacetamido)-ceph-3-em-4-carboxylic acid (syn-isomer).

A solution of t-butyl 3-acetoxymethyl-7$\beta$-(2-dichloroacetoxyimino-2-phenylacetamido)-ceph-3-em-4-carboxylate (3.0 g) in trifluoroacetic acid (25 ml.) was allowed to stand at room temperature for ten minutes. The excess acid was removed under reduced pressure, and benzene evaporated from the residue, which was taken up into ethyl acetate and extracted into saturated aqueous sodium bicarbonate. The aqueous phase was washed with ethyl acetate, acidified and extracted with ethyl acetate. The extracts were combined, dried, concentrated to about 5 ml and added dropwise to petroleum (200 ml.). The solid which precipitated was filtered and dried, giving 3-acetoxymethyl-7$\beta$-(2-hydroxyamino-2-phenylacetamido)ceph-3-em-4-carboxylic acid (syn-isomer) as a white solid (1.9 g; 88%) $[\alpha]_D$+68° (c 0.8 DMSO), $\lambda_{max.}$ (EtOH) 254 nm ($\epsilon$ 17,600), $\nu_{max.}$ (Nujol) 3380 (NH and OH) 1778 ($\beta$-lactam), 1720 (CO$_2$H and acetate), 1666 and 1540 cm$^{-1}$ (CONH), $\tau$(DMSO-d$_6$) values include 0.32 (doublet, J 9 Hz; NH of syn-isomer), 1.00 (doublet, J 9 Hz; NH of anti-isomer, comprising ca. 10% of the product), 2.15–2.7 (multiplet; aromatic protons), 7.8 (singlet; CH$_3$CO).

EXAMPLE 3

Sodium 3-acetoxymethyl-7$\beta$-[2-hydroxyimino-2-(thien-2-yl)acetamido]ceph-3-em-4-carboxylate (syn-isomer)

(a) 2-Dichloroacetoxyimino-2-(thien-2-yl)acetyl chloride (syn-isomer)

Phosphorus pentachloride (27.2 g.) was added portionwise during ca. 20 minutes to a stirred and cooled (ice-bath) suspension of 2-dichloroacetoxyimino-2-(thien-2-yl)acetic acid (syn-isomer) (37.0 g.) in methylene chloride (370 ml.). The mixture was stirred at 0° for a further 30 minutes during which time all the solid dissolved. After removal of the solvent under reduced pressure, benzene was evaporated from the residue at 20°, and the process repeated to give 2-dichloroacetoxyimino-2-(thien-2-yl)acetyl chloride (syn-isomer) as an oil that was used directly in the next stage.

(b) t-Butyl 3-acetoxymethyl-7β-[2-dichloroacetoxyimino-2-(thien-2-yl)-acetamido]-ceph-3-em-4-carboxylate (syn-isomer).

A solution of 2-dichloroacetoxyimino-(thien-2-yl)acetyl chloride (syn-isomer) in ethyl acetate (300 ml.) was added to a stirred solution of t-butyl 3-acetoxymethyl-7β-aminoceph-3-em-4-carboxylate (43 g) and propylene oxide (34 ml.) in ethyl acetate (400 ml.) at 20°. Initially a solid precipitated out but it gradually redissolved. The temperature was maintained between 20° and 30° by alternately cooling and warming the solution. After 4 hours the solution was washed with 2 N-hydrochloric acid, saturated sodium bicarbonate solution, water and brine, and was dried and concentrated under reduced pressure to give the title ester as an oil that was used directly in the next stage.

(c) 3-Acetoxymethyl-7β-[2-dichloroacetoxyimino-2-(thien-2-yl)acetamido]-ceph-3-em-4-carboxylic acid (syn-isomer)

A solution of t-butyl 3-acetoxymethyl-7β-[2-dichloroacetoxyimino-(thien-2-yl)acetamido]ceph-3-em-4-carboxylate (syn-isomer) in anisole (20 ml.) was treated with trifluoroacetic acid (100 ml.). After 5 minutes at 20° the solution was concentrated under reduced pressure at 35°. Ethyl acetate was added and the solution was again concentrated, whereupon a solid separated out. Ethyl acetate was evaporated from the residue three more times and the solid was collected and washed with ether to give 3-acetoxymethyl-7β-[2-dichloroacetoxyimino-2-(thien-2-yl)acetamido]ceph-3-em-4-carboxylic acid (syn-isomer) (37 g., 53%) $\lambda_{max.}$ (ethanol) 263 nm ($\epsilon$14,800), $\tau$(DMSO-d6) values include −0.19 (doublet, J 8 Hz; NH), 3.02 (singlet, CHCl$_2$), 7.94 (singlet, OCOCH$_3$).

(d) 3-Acetoxymethyl-7β-[2-hydroxyimino-2-(thien-2-yl)acetamido]ceph-3-em-4-carboxylic acid (syn-isomer)

3-Acetoxymethyl-7β-[2-dichloroacetoxyimino-2-(thien-2-yl)acetamido]ceph-3-em-4-carboxylic acid (syn-isomer) (36.1 g.) was partitioned between ethyl acetate (ca. 250 ml.) and saturated sodium bicarbonate solution (200 ml.). The layers were separated and the ethyl acetate solution was extracted twice more with sodium bicarbonate solution. The combined extracts were washed with ethyl acetate, then covered with ethyl acetate and carefully acidified with concentrated hydrochloric acid. The layers were separated and the aqueous layer was extracted twice more with ethyl acetate. The combined extracts were washed with water and brine, dried and concentrated under reduced pressure to a small volume (ca. 60 ml.), which was added dropwise to stirred petroleum (b.p. 40°-60°, ca. 1500 ml.). The resulting buff-coloured solid was collected to give 3-acetoxymethyl-7β-[2-hydroxyimino-2-(thien-2-yl)acetamido]ceph-3-em-4-carboxylic acid (syn isomer) (27.5 g., 95%).

(e) Sodium 3-acetoxymethyl-7β-[2-hydroxyimino-(thien-2-yl)acetamido]-ceph-3-em-4-carboxylate (syn-isomer).

A solution of sodium 2-ethylhexoate (12.6 g.) in ethyl acetate (120 ml.) was added to a stirred solution of 3-acetoxymethyl-7β-[2-hydroxyimino-2-(thien-2-yl)acetamido]ceph-3-em-4-carboxylic acid (syn-isomer) (27.3 g.) in ethyl acetate (270 ml.) at 20°. The mixture was cooled to 0° for 1 hour and the pale buff solid was filtered off, washed with ethyl acetate and ether and dried in vacuo to give the title sodium salt (25.1 g., 87.5%), $[\alpha]_D$+78.5° (c 1.1 DMSO), $\lambda_{max.}$ (pH 6 buffer) 261 nm ($\epsilon$15,200), $\lambda_{inflexion}$ 285 nm ($\epsilon$10,200), $\tau$ (D$_2$O) 2.41 (d, 5 Hz; thienyl C-3 H or C-5 H) 2.64 (d, J 4 Hz; thienyl C-5 H or C-3 H), 2.84 (dd, J4 and 5 Hz; thienyl C-4H), 4.12 (d, J 5 Hz; C-7H), 4.78 (d, J 5 Hz; C-6H); 5.08 and 5.28 (2ds, branches of quartet, J 12 Hz; C-3 CH$_2$), 6.33 and 6.65 (2ds, branches of quartet, J 18 Hz; C-2 CH$_2$) and 7.91 (s; OCOCH$_3$).

EXAMPLE 4

7β-(2-Hydroxyimino-2-phenylacetamido)-3-(5-methyl-1,3,4-thiadiazol-2-yl)thiomethylceph-3-em-4-carboxylic acid (syn-isomer).

(a) 7β-Formamido-3-(5-methyl-1,3,4-thiadiazol-2-yl)thiomethylceph-3-em-4-carboxylic acid A solution of 7β-formamido-3-acetoxymethylceph-3-em-4-carboxylic acid (24.0 g) and 5-methyl-1,3,4-thiadiazole-2-thiol (10.56 g) in M. pH 6.4 phosphate buffer (600 ml.) was heated at 60° for 4½ hours. The solution was cooled to 20° and the pH was adjusted from 6 to 5 with phosphoric acid. The solution was extracted with ethyl acetate the pH of the aqueous layer was taken to 2 with phosphoric acid and the product was extracted into ethyl acetate. The extract was washed with brine, dried and concentrated to a low volume under reduced pressure and added to stirred petroleum. The resulting solid was collected and dried to give the title compound (9.36 g.) $[\alpha]_D$−98° (c 1 DMSO), $\lambda_{max.}$ (pH 6 buffer) 271 nm ($\epsilon$11,400), $\tau$ values (D$_2$O+NaHCO$_3$) include 1.74 (s; CHO), 4.30 (d, J 4.5 Hz; C-7 H), 4.88 (d, J 4.5 Hz; C-6 H) and 7.25 (s; CH$_3$).

(b) Diphenylmethyl 7β-formamido-3-(5-methyl-1,3,4-thiadiazol-2-yl)thiomethylceph-3-em-4-carboxylate A solution of 7β-formamido-3-(5-methyl-1,3,4-thiadiazol-2-yl)thiomethylceph-3-em-4-carboxylic acid (8.5 g) in tetrahydrofuran (300 ml.) was treated with an excess of a solution of diphenyldiazomethane in petroleum (300 ml.) and the mixture was kept at 20° for 16 hours. A few drops of acetic acid were added and solvents were removed under reduced pressure. The resulting yellow syrup was dissolved in ethyl acetate and washed with sodium bicarbonate solution. A solid (7.5 g) precipitated and was dried in vacuo. A sample (5.77 g) of the wet solid was dissolved in methylene chloride, and the solution was dried and concentrated under reduced pressure. The residue was crystallised from methanol to give the title ester (5.08 g), m.p. 108° (decomp.), $\lambda_{max.}$ (EtOH) 268 nm ($\epsilon$12,400), $\tau$ (CDCl$_3$+a little DMSO-d6) values include 1.50 (d, J 9 Hz; NH), 1.72 (s; HCO), 6.30 (singlet; C-2 CH$_2$) and 7.31 (singlet; CH$_3$).

(c) Diphenylmethyl 7β-amino-3-(5-methyl-1,3,4-thiadiazol-2-yl)thiomethyl-ceph-3-em-4-carboxylate hydrochloride Phosphorus oxychloride (1.8 ml.) was added dropwise during 2 minutes to a stirred and cooled (0°) suspension of diphenylmethyl 7β-formamido-3-(5-methyl-1,3,4-thiadiazol-2-yl)thiomethylceph-3-em-4-carboxylate (4.1 g) in dry methanol. After 30 minutes the yellow solution was concentrated under reduced pressure. Ethyl acetate was added to the residue and the resulting solid was collected and washed with ether to give the title hydrochloride $\lambda_{max}$. (EtOH) 266 nm ($\epsilon$11,300), $\nu_{max}$. (Nujol) include 2590 ($NH_3^+$), 1778 (β-lactam) and 1710 cm.$^{-1}$ (ester), τ values (DMSO-$d_6$) include 0.50 (broad m; $NH_3$), 2.3–2.7 (m; phenyl protons), 3.02 (s; $CHPh_2$), 4.66+4.76 (m; C-7 H and C-6 H), 5.39+5.69 (2ds, branches of quartet, J 13 Hz; C-3 $CH_2S$). 6.15 (singlet; C-2 $CH_2$) and 7.36 (singlet; $CH_3$).

(d) Diphenylmethyl 7β-amino-3-(5-methyl-1,3,4-thiadiazol-2-yl)thiomethyl-ceph-3-em-4-carboxylate Diphenylmethyl 7β-amino-3-(5-methyl-1,3,4-thiadiazol-2-yl)thiomethylceph-3-em-4-carboxylate hydrochloride (5 g) was shaken with saturated sodium bicarbonate solution and ethyl acetate. The layers were separated and the aqueous layer was re-extracted with ethyl acetate. The combined ethyl acetate extracts were washed with sodium bicarbonate solution and brine, dried and concentrated under reduced pressure. The residue was crystallised from ethyl acetate-ether to give the title free base (2.75 g) m.p. 152° (decomp.), $\lambda_{max}$. (EtOH) 268 nm ($\epsilon$9,000), $\lambda_{max}$. ($CHBr_3$) includes 3400 and 3335 ($NH_2$), 1772 (β-lactam), 1720 (ester), τ ($CDCl_3$) values include 2.50–2.75 (m; phenyl protons), 3.00 (s; $CHPh_2$), 7.31 (singlet; $CH_3$) and 8.22 (s; $NH_2$).

(e) 7β-(2-Hydroxyimino-2-phenylacetamido)-3-(5-methyl-1,3,4-thiadiazol-2-yl)thiomethylceph-3-em-4-carboxylic acid (syn-isomer)

A 1-molar solution of 2-dichloroacetoxyimino-2-phenylacetyl chloride (syn-isomer) in ethyl acetate (3.8 ml.) was added during 5 minutes to a stirred suspension of diphenylmethyl 7β-amino-3-(5-methyl-1,3,4-thiadiazol-2-yl)thiomethylceph-3-em-4-carboxylate (1.73 g) in ethyl acetate (20 ml.) containing propylene oxide (0.9 ml) at 20°. After the addition was complete the solution was kept for 1 hour, then diluted with ethyl acetate and washed with 2 N-hydrochloric acid, sodium bicarbonate solution, water and brine. The dried solution was evaporated to give a red foam (2.76 g). The foam (2.6 g) was dissolved in anisole (5 ml.) and treated with trifluoroacetic acid (20 ml.). After 5 minutes the solution was concentrated under reduced pressure and the residue was dissolved in ethyl acetate. The solution was washed with water and then extracted with sodium bicarbonate solution. The combined aqueous extracts were washed with ethyl acetate acidified with 2 N-hydrochloric acid and extracted into ethyl acetate. The combined extracts were washed with brine, dried, concentrated under reduced pressure to a small volume, and added dropwise to stirred petroleum (ca. 500 ml) to give the title acid as a yellow solid (1.38 g) $[\alpha]_D$ −79° (c 1.2 DMSO), $\lambda_{max}$. (pH 6 buffer) 256 nm ($\epsilon$19,250), $\lambda_{max}$. (Nujol) include 3650–2100 (bonded OH), 3250 (NH), 1769 (β-lactam), 1660+1525 cm.$^{-1}$ (CONH), τ (DMSO-$d_6$) 0.33 (d, J 8 Hz; CONH), 2.2–2.7 (m; phenyl protons), 4.12 (dd, J 5 and 8 Hz; C-7H), 4.78 (d, J 5 Hz; C-6H), 5.43+5.77 (2 ds, branches of quartet, J 18 Hz; C-3 $CH_2$), 6.17+6.41 (2 ds, branches of quartet, J 18 Hz; C-2 $CH_2$) and 7.30 (s; $CH_3$).

EXAMPLES 5–16

General Procedures for the Preparation of 7β-(2-Hydroxyimino-2-arylacetamido)-3-(substituted)-methylceph-3-em-4-carboxylic Acids

(i) Preparation of the Intermediate 2-Dichloroacetoxyimino Esters

Method A

To a solution of the t-butyl or diphenylmethyl ester of 7β-amino-3-(substituted)-methylceph-3-em-4-carboxylic acid (1 equiv.) in ethyl acetate was added, dropwise with stirring at room temperature, a solution of the appropriate 2-dichloroacetoxyimino-2-arylacetyl chloride (syn or anti- isomer) (1–1.15 equivs.) in ethyl acetate. The mixture was stirred for a period of 1–2 hr. during which the hydrochloride of the 7β-amino-3-(substituted)methylceph-3-em-4-carboxylic acid ester precipitated and was removed by filtration. The filtrate was washed successively with 2 N-hydrochloric acid, water, briefly with saturated sodium hydrogen carbonate solution and brine. The organic layer was dried and evaporated to give the required 2-dichloroacetoxyimino ester as a foam or oil.

Method B

To a solution of the t-butyl or diphenylmethyl ester of 7β-amino-3-(substituted)-methylceph-3-em-4-carboxylic acid (1 equiv.) and propylene oxide (3–15 equivs.) in ethyl acetate (methylene chloride was used in Example 7) was added, dropwise with stirring at room temperature, a solution of the appropriate 2-dichloroacetoxyimino-2-arylacetyl chloride (syn-isomer) (1.05–1.25 equivs.) in ethyl acetate. Stirring was continued until the reaction was complete (t.l.c, usually 40 min.-2hr.) at room temperature. The reaction solution was then worked up as described in Method A to give the required ester.

Method C

A solution of the 2-dichloroacetoxyimino-2-arylacetyl chloride (syn-isomer) (1–1.1 equiv.) in ethyl acetate was added dropwise to a stirred suspension of the diphenylmethyl 7β-amino-3-acyloxy-methylceph-3-em-4-carboxylate p-toluenesulphonic acid salt (1 equiv.) and propylene oxide (8–20 equiv.) in ethyl acetate at room temperature. After stirring for 20 minutes - 2 hours the resulting solution was worked up as described in Method A to give the required ester.

Method D

As for method C except that the reaction was effected in a mixture of acetonitrile and dimethylacetamide in place of ethyl acetate-propylene oxide; this applies only to Example 12.

(ii) Deprotection of the Intermediate Esters

Method E

The t-butyl or diphenylmethyl 2-dichloroacetoxyimino-ester prepared by Methods A or B was dissolved in trifluoroacetic acid (7–15 ml./g. ester) and left at room temperature for 5–10 min. then evaporated under reduced pressure. The crude product was sometimes azeotroped with benzene to remove traces of trifluoroacetic acid. The crude product was taken up in ethyl acetate and extracted with a saturated solution of sodium hydrogen carbonate. The aqueous extracts were washed with ethyl acetate and then acidified with 2 N-hydrochloric acid and extracted into ethyl acetate. The organic layer was separated, dried and evaporated to a small volume and added dropwise to a large, well-stirred, volume of petroleum (b.p. 40°–60°). The resulting amorphous solid was collected and dried in vacuo to provide the required 7β-(2-hydroxyimino-2-arylacetamido)-3-(substituted)-methylceph-3-em-4-carboxylic acid.

Method F

The ester prepared by Methods A–D was dissolved in anisole (1–15 ml./g. ester) and treated with trifluoroacetic acid (4–10 ml./g. ester) at room temperature. After 5–10 mins. the trifluoroacetic acid was removed by evaporation under reduced pressure and the required acid was isolated as described in Method E.

(iii) Preparation of Diphenylmethyl 7β-amino-3-acyloxymethylceph-3-em-4-carboxylate toluene-p-sulphonate salts used as Starting Materials in Examples 11–14 inclusive.

(a) Diphenylmethyl 3-pivaloyloxymethyl-7β-(thien-2-yl)acetamidoceph-3-em-4-carboxylate A solution of pyridine (2.4 ml.) in dry tetrahydrofuran (5 ml.) was added to a stirred solution of diphenylmethyl 3-hydroxymethyl-7β-(thien-2-yl)acetamidoceph-3-em-4-carboxylate (3.12 g) and pivaloyl chloride (7.2 g) in dry tetrahydrofuran (150 ml) at 20°. The solution was stirred at 20° for 16 hours, filtered and concentrated under reduced pressure. The residue was dissolved in ethyl acetate and washed successively with sodium bicarbonate solution, 2 N-hydrochloric acid, sodium bicarbonate solution, water and brine. The dried solution was concentrated under reduced pressure to give a solid residue that was triturated with ether to give the title ester (2.7 g; 75%), $[\alpha]_D+5.1°$ (c 1.4, CHCl$_3$), $\lambda_{inflex.}$ (ethanol) 235 ($\epsilon$14,100), 257 ($\epsilon$8,300) and 263 nm. ($\epsilon$8,050), $\lambda_{max.}$ (CHBr$_3$) 1787 (β-lactam), 1722 (ester), 1680 and 1510 cm.$^{-1}$ (CONH) $\tau$ (CDCl$_3$) values include 8.81 (singlet; C(CH$_3$)$_3$).

Similarly prepared were:

(b) Diphenylmethyl 3-benzoyloxymethyl-7β-(thien-2-yl)acetamidoceph-3-em-4-carboxylate (88%), $\lambda_{max.}$ (EtOH) 223 nm ($\epsilon$28,600), $\lambda_{inflex.}$ 260 ($\epsilon$9,800) and 278.5 nm ($\epsilon$7,300), $\lambda_{max.}$ (CHBr$_3$) 1795 (β-lactam), 1729 (ester), 1690 and 1516 cm$^{-1}$ (CONH) $\tau$ (CDCl$_3$) values include 2.3−3.1 (aromatic protons) 6.18 (singlet; thienyl-$\underline{CH_2}$) 4.62+5.02 (2 doublets J 14 Hz, C-3 $\underline{CH_2}$OCO).

(c) Diphenylmethyl 3-crotonoyloxymethyl-7β-(thien-2-yl)acetamidoceph-3-em-4-carboxylate (52%), $[\alpha]_D+7.2°$ (c 0.8 CHCl$_3$), $\lambda_{inflex.}$ (ethanol) 237.5 ($\epsilon$ 14,400) and 260 nm ($\epsilon$ 8,000), $\nu_{max.}$ (CHBr$_3$) 1783 (β-lactam), 1719 (ester), 1680 and 1510 cm.$^{-1}$ (CONH), $\tau$ values (CDCl$_3$) include 6.19 (singlet); thienyl-$\underline{CH_2}$) and 8.12 (double doublet, J 2 and 7 Hz; CH-CH$\underline{CH_3}$).

(d) Diphenylmethyl 3-isobutyryloxymethyl-7β-(thien-2-yl)acetamidoceph-3-em-4-carboxylate (75%), $[\alpha]_D+4°$ (c 0.9 CHCl$_3$), $\lambda_{inflex.}$ (EtOH) 235 ($\epsilon$ 13,400), 257 ($\epsilon$ 7,900) and 261.5 nm ($\epsilon$ 7,750), $\nu_{max.}$ (CHBr$_3$) 1767 (β-lactam), 1710 (ester), 1667 and 1500 cm.$^{-1}$ (CONH), $\tau$ values (CDCl$_3$) include 6.19 (singlet; thienyl CH$_2$), 8.89 (doublet, J 6.5 Hz; ($\underline{CH_3}$)$_2$CH).

(e) Diphenylmethyl 7β-amino-3-pivaloyloxymethylceph-3-em-4-carboxylate toluene-p-sulphonate salt.

A solution of phosphorus pentachloride (6.2 g) in methylene chloride (80 ml) was added to a cooled (−10°) and stirred solution of diphenylmethyl 3-pivaloyloxymethyl-7β-(thien-2-yl)acetamidoceph-3-em-4-carboxylate (6.0 g) and pyridine (9.6 ml.) in methylene chloride (80 ml). After 30 minute methanol (100 ml.) was added at such a rate that the temperature remained at −10°. The solution was then allowed to warm to 20° and after 3 hours at 20° was cooled to 0°. 2 N-Hydrochloric acid (140 ml.) was added to the vigorously stirred solution. After the stirring had continued for 1 hour the methylene chloride layer was separated and washed successively with 2 N-hydrochloric acid, sodium bicarbonate solution, water and brine, dried and concentrated under reduced pressure. The residual gum was dissolved in ethyl acetate (10 ml.) and was treated with a solution of toluene-p-sulphonic acid monohydrate (1.89 g) in ethyl acetate (10 ml.). The cooled solution deposited crystals that were collected and washed with ethyl acetate and ether to give the title salt (4.34 g; 66%), $[\alpha]_D+5.9°$ (c 1, DMSO), $\lambda_{max.}$ (ethanol) 261.5 nm ($\epsilon$ 7,700), $\lambda_{inflex.}$ 267.5 ($\epsilon$ 7,400) and 226.5 nm ($\epsilon$ 16,600), $\lambda_{max.}$ (CHBr$_3$) 2600–2800 (NH$_3^+$), 1800 (β-lactam) and 1731 cm.$^{-1}$ (ester), $\tau$ values (CDCl$_3$) include 2.20+2.98 (2 doublets, J 8 Hz; toluene-sulphonate aromatic protons) and 8.89 (singlet; C(CH$_3$)$_3$). Similarly prepared were:

(f) Diphenylmethyl 7β-amino-3-benzoyloxymethylceph-3-em-4-carboxylate toluene-p-sulphonate salt, as needles; (75%), $[\alpha]_D+9.5°$ (c 0.94 DMSO), $\lambda_{max.}$ (ethanol) 221 ($\epsilon$ 32,200) and 262 nm ($\epsilon$ 9,100), $\nu_{max.}$ (Nujol) 2600–2800 (NH$_3^+$), 1804 (β-lactam) and 1730 cm$^{-1}$ (ester), $\tau$ (DMSO-d$_6$) values include 4.79+4.99 [2 doublets, (branches of quartet) J 14 Hz; C-3 $\underline{CH_2}$] and 7.70 (singlet; CH$_3$).

(g) Diphenylmethyl 7β-amino-3-crotonoyloxymethylceph-3-em-4-carboxylate toluene-p-sulphonate salt, (54%), $[\alpha]_D +7.3°$ (c 0.89 DMSO), $\lambda_{max.}$ (ethanol) 261.5 nm ($\epsilon$ 8,000), $\lambda_{inflex.}$ 266 nm ($\epsilon$ 7,700) $\nu_{max.}$ (CHBr$_3$) 2600–2700 (NH$_3^+$), 1790 (β-lactam), 1720 and 1221 cm.$^{-1}$ (ester), $\tau$ values (CDCl$_3$) include 2.20+2.89 [2 doublets, (branches of quartet) J 8 Hz; toluene-p-sulphonate aromatic protons] and 8.11 (double doublet, J 6.5 and 1.5 Hz; CH=CH—CH$_3$).

(h) Diphenylmethyl 7β-amino-3-isobutyryloxymethylceph-3-em-4-carboxylate toluene-p-sulphonate salt, (65%), $[\alpha]_D+5.3°$ (c 1.21, DMSO), $\lambda_{max.}$ (EtOH) 262 nm ($\epsilon$ 8,000), $\nu_{max.}$ (CHBr$_3$) 1780 (β-lactam), 1718 cm.$^{-1}$ (ester), $\tau$ values (CDCl$_3$) include 2.21, 2.99 (2 doublets J 8 Hz; toluene-p-sulphonate) and 8.91 (doublet, J 6 Hz; (C$\underline{H}_3$)$_2$CH).

EXAMPLE 5

(a) t-Butyl 7β-(2-dichloroacetoxyimino-2-phenylacetamido)-3-methylceph-3-em-4-carboxylate (syn-isomer)

as a pale yellow foam (75%), $\nu_{max.}$ (CHBr$_3$) 3400 (NH), 1782 (β-lactam), 1712 (ester), 1782 and 1693 cm.$^{-1}$ (CONH), τ (DMSO-d$_6$) values include 2.15–2.60 (multiplet; aromatic protons), 3.03 (singlet; C$\underline{H}$Cl$_2$), 8.03 (singlet; C-3 methyl), 8.54 (singlet; t-butyl ester) was prepared by Method A.

(b) 7β-(2-Hydroxyimino-2-phenylacetamido)-3-methylceph-3-em-4-carboxylic acid (syn-isomer containing ca. 10% of the anti-isomer)

(88%), $\nu_{max.}$ (Nujol) 3270 (NH), 1760 (β-lactam), 2600 and 1710 (CO$_2$H), 1670 and 1530 cm$^{-1}$ (CONH), τ (DMSO-d$_6$) values include 0.36 (doublet, J 9 Hz; NH of syn-isomer), 1.15 (doublet, J 9 Hz; NH of anti-isomer), 2.25–2.65 (multiplet; aromatic protons), 7.92 (singlet; CH$_3$) was prepared by Method E.

EXAMPLE 6

(a) Diphenylmethyl 7β-(2-dichloroacetoxyimino-2-phenylacetamido)-3-methylthiomethylceph-3-em-4-carboxylate (syn-isomer)

as an oil, $\nu_{max.}$ (CHBr$_3$) 3500 (OH), 1790 (β-lactam), 1726 (ester), 1696 and 1520 cm.$^{-1}$ (CONH), τ (DMSO-d$_6$) 2.1–2.8 (multiplet; aromatic protons), 3.05 (singlet; diphenylmethyl ester), 4.05 (quartet, J 9 Hz; and 4.5 Hz; C-7 H), 4.85 (doublet, J 4.5 Hz; C-6 H), 6.45 (broad singlet; C-2 and C-3 CH$_2$), 8.2 (singlet; SCH$_3$) was prepared by Method A.

(b) 7β-(2-Hydroxyimino-2-phenylacetamido)-3-methylthiomethylceph-3-em-4-carboxylic acid (syn-isomer)

$[\alpha]_D$+47.5° (c 1, DMSO), $\lambda_{max.}$ (pH 6 phosphate buffer) 255 nm (ε 18,400), $\nu_{max.}$ (Nujol) 3270 (NH and OH), 1752 (β-lactam), 1660 and 1518 cm.$^{-1}$ (CONH), τ (DMSO-d$_6$) 0.35 (doublet, J 9 Hz; NH), 2.3–2.7 (multiplet; aromatic protons), 4.15 (quartet, J 9 Hz and 4.5 Hz; C-7 H), 4.7 (doublet, J 4.5 Hz; C-6 H), 6.35 (broad singlet; C-2 and C-3 CH$_2$) 7.98 (singlet; S—CH$_3$) was prepared by Method E.

EXAMPLE 7

(a) Diphenylmethyl 7β-(2-dichloroacetoxyimino-2-phenylacetamido)-3-vinylceph-3-em-4-carboxylate (syn-isomer) as a yellow foam $\nu_{max.}$ (CHBr$_3$) 3500 (OH), 3380 (NH), 1770 (β-lactam), 1720 (ester), 1685 and 1510 cm$^{-1}$ (CONH), τ (CDCl$_3$) values include 2.2–2.85 (multiplet; aromatic protons), 4.0–5.0 (multiplet; C-6 H, C-7H and vinyl —CH$_2$), 6.40 (broad singlet; C-2 CH$_2$) was prepared by Method B.

(b) 7β-82-Hydroxyimino-2-phenylacetamido)-3-vinylceph-3-em-4-carboxylic acid (syn-isomer)

as a white solid (45%), $[\alpha]_D$ −72° (c 0.85, DMSO), $\lambda_{max.}$ (pH 6 buffer) 285 nm (ε 16,400), $\nu_{max.}$ (Nujol) 3270 (NH and OH), 1754 (β-lactam), 1710 (CO$_2$H), 1660 and 1520 cm$^{-1}$ (CONH), τ (DMSO-d$_6$) values include 0.30 (doublet, J 9 Hz; NH), 2.3–2.6 (multiplet; aromatic protons), 3.03 (quartet, J 11 Hz and 18 Hz; C$\underline{H}$=CH$_2$), 4.37 and 4.66 (two doublets, J 11 Hz and 18 Hz; CH=CH$_2$), 6.08 and 6.41 [two doublets (branches of quartet) J 18 Hz; C-2 CH$_2$] was prepared by Method E.

EXAMPLE 8

(a) t-Butyl-3-Acetoxymethyl-7β-[2-dichloroacetoxyimino-2-(thien-2-yl)acetamido]-ceph-3-em-4-carboxylate (syn isomer) was isolated as an oil by Method A and deprotected by Method F to give:

(b) 3-Acetoxymethyl-7β-[2-hydroxyimino-2-(thien-2-yl) acetamido]ceph-3-em-4-carboxylic acid (syn-isomer)

as an amorphous solid (0.36 g.), $[\alpha]_D$+57° (c 0.8, DMSO), $\lambda_{max.}$ (ethanol) 263 nm (ε 13,900), $\nu_{max.}$ (Nujol) 3280 (NH), 1772 (β-lactam), 1720 (acetate), and 1662 and 1530 cm.$^{-1}$ (CONH), τ (DMSO-d$_6$) values include 0.23 (doublet, J 8 Hz; NH), 2.36 (double doublet, J 1 and 5 Hz; thienyl C-5 H), 2.82 (multiplet; thienyl C-3 H and C-4H), and 7.93 (singlet; OCOCH$_3$).

EXAMPLE 9

(a) Diphenylmethyl 3-azidomethyl-7β-(2-dichloroacetoxyimino-2-phenylacetamido)ceph-3-em-4-carboxylate (syn-isomer)

was obtained as a solid (46%), $\lambda_{max.}$ (EtOH) 254 nm (ε 18,000), $\nu_{max.}$ (CHBr$_3$) 3420 (NH), 2128 (N$_3$), 1800 (β-lactam), τ (CDCl$_3$) values include 2.1–2.85 (multiplet; aromatic protons), 3.79 (singlet CHCl$_2$), using Method B. Deprotection by Method F gave (b) 3-Azidomethyl-7β-(2-hydroxyimino-2-phenylacetamido) ceph-3-em-4-carboxylic acid (syn-isomer)

(85%), $[\alpha]_D$+ 70° (c 0.84, DMSO), $\lambda_{max.}$ (pH 6 phosphate buffer) 253.5 nm (ε 18,800), $\nu_{max.}$ (Nujol) 3260 (NH), 2096 (N$_3$) 1762 (β-lactam), 1650 and 1520 cm.$^{-1}$ (CONH), τ (DMSO-d6) values include 0.30 (NH), 2.3–2.65 (aromatic protons), 5.57 and 6.06 [two doublets, J 13 Hz; C-3 CH$_2$].

EXAMPLE 10

(a) Diphenylmethyl 7β-(2-dichloroacetoxyimino-2-phenylacetamido)-3-methoxymethylceph-3-em-4-carboxylate (syn-isomer)

as a pale yellow foam (2.31 g.; 94%), $[\alpha]_D$+24° (c 0.8 DMSO), $\lambda_{max.}$ (EtOH) 256 nm (ε 17,800), $\nu_{max.}$ (Nujol) 1790 (β-lactam), 1725 (CO$_2$R), 1698 and 1520 cm.$^{-1}$ (amide), τ (DMSO-d$_6$) values include 2.40–2.73 (multiplet; aromatic protons), 3.75 (singlet; C$\underline{H}$Cl$_2$), 6.80 (singlet; —OCH$_3$) was prepared by Method B and deprotected by Method F to give:

(b) 7β-(2-Hydroxyimino-2-phenylacetamido)-3-methoxymethylceph-3-em-4-carboxylic Acid (syn-isomer)

as a solid (55%), $[\alpha]_D$+77° (c 1.02, DMSO), $\lambda_{max.}$ (EtOH) 253 nm (ε 16,800), $\nu_{max.}$ (Nujol) 1785 (β-lactam), 1730 (—CO$_2$H), 1678 and 1580 cm.$^{-1}$ (amide), τ (DMSO-d$_6$) values include 0.35 (doublet J 9 Hz; NH), 2.3 to 2.6 (multiplet; aromatic protons), 4.14 (quartet J 9 Hz and 4.5 Hz; C-7 H), 4.79 (doublet J 4.5 Hz; C-6H), 6.80 (singlet; OCH$_3$).

EXAMPLE 11

(a) Diphenylmethyl 7β-(2-dichloroacetoxyimino-2phenyl acetamido)-3-pivaloyloxymethylceph-3-em-4-carboxylate (syn-isomer)

was obtained as an oil by Method C and directly deprotected by Method F to give (b) 7β-(2-Hydroxyimino-2-phenylacetamido)-3-pivaloyloxymethylceph-3-em-4-carboxylic acid (syn isomer)

as a yellow solid (74%), $[\alpha]_D+62°$ (c 1, DMSO), $\lambda_{max.}$ (pH 6 phosphate) 253.5 nm (ε17,200), $\nu_{max.}$ (Nujol) 3700-2200 (bonded OH), 1771 (β-lactam), 1710 (ester and carboxylic acid), 1665 and 1526 cm.$^{-1}$ (CONH), τ (DMSO-d$_6$) values include 0.34 (doublet, J 8 Hz; NH) 2.3-2.65 (multiplet; aromatic protons), and 8.82 (singlet; C(CH$_3$)$_3$).

EXAMPLE 12

(a) Diphenylmethyl 3-benzoyloxymethyl-7β-(2-dichloroacetoxyimino-2-phenylacetamido)ceph-3-em-4-carboxylate was isolated as a mixture of syn and anti-isomers prepared by Method D. Deprotection of the mixture by Method F and separation of the acids by preparative layer chromatography on Merck silica gel 254F plates using chloroform:methanol:acetic acid (90:7:5 by volume) gave, as the slower moving component:

(b) 3-Benzoyloxymethyl-7β-(2-hydroxyimino-2-phenylacetamido)ceph-3-em-4-carboxylic acid (syn-isomer)

$[\alpha]_D+54.4°$ (c 1, DMSO), $\lambda_{max.}$ (pH 6 phosphate) 236.5 nm (ε22,200), $\lambda_{inflex.}$ 250 nm (ε19,600), $\nu_{max.}$ (Nujol) 3680-2200 (bonded OH), 1770 (β-lactam), 1710 (carboxylic acid and ester), 1680 and 1515 cm$^{-1}$ (CONH), τ (DMSO-d$_6$) values include 0.32 (doublet, J 8 Hz; NH) 2.00-2.50 (multiplet; aromatic protons), and 6.16 and 6.38 [2 doublets (branches of quartet) J 18 Hz; C-2 CH$_2$].

EXAMPLE 13

3-Crotonoyloxymethy-7-β-(2-hydroxyimino-2-phenylacetamido)ceph-3-em-4-carboxylic acid (syn-isomer)

as an amorphous solid (60%), $[\alpha]_D+54°$ (c 1.0, DMSO), $\lambda_{max.}$ (pH 6 phosphate) 252 nm (ε16,700), $\nu_{max.}$ (Nujol) 1774 (β-lactam), 1710 (CO$_2$H), 1670 and 1530 cm$^{-1}$ (CONH), τ (DMSO-d$_6$) values include 0.35 (doublet, J 8 Hz; NH) 2.3 to 2.7 (multiplet; aromatic protons), 3.03 (double quartet, J 15 and 7 Hz; CH=CH—CH$_3$), 4.09 (doublet J 15 and 1 Hz; CH=CH—CH$_3$), 8.14 (double doublet, J 7 and 1 Hz; CH=CH—CH$_3$) was prepared by a combination of Methods C and F, the intermediate ester being used without characterisation.

EXAMPLE 14

(a) Diphenylmethyl 7β-(2-dichloroacetoxyimino-2-phenylacetamido)-3-isobutyryloxymethylceph-3-em-4-carboxylate (syn isomer) was isolated as a gum $[\alpha]_D+14°$ (c 1, DMSO), $\lambda_{max.}$ (EtOH) 255 nm (ε12,300), $\nu_{max.}$ (CHBr$_3$) 3380 (NH), 1790 (β-lactam), 1695 and 1518 cm. $^{-1}$(CONH), τ (CDCl$_3$) values include 2.0-2.9 (multiplet; NH and aromatic protons), 3.74 (singlet; CHCl$_2$), 8.88 (doublet J 7 Hz; gem dimethyl) using Method C. Deprotection by Method F gave (b) 7β-(2-Hydroxyimino-2-phenylacetamido)-3-isobutyryloxymethylceph-3-em-4-carboxylic acid (syn-isomer) as a solid (87%), $[\alpha]_D+52°$ (c 1.0, DMSO), $\lambda_{max.\,(EtOH)}$ 253 nm (ε14,100), $\epsilon_{max.}$ (Nujol) 3280 (NH), 1770 (β-lactam), 1660 and 1520 cm.$^{-1}$ (amide), τ (DMSO-d6) values include 0.33 (doublet J 9 Hz; NH), 2.3-2.6 (multiplet; aromatic protons) and 8.86 (doublet J 7Hz; C(CH$_3$)$_2$).

EXAMPLE 15

(a) t-Butyl 3-acetoxymethyl-7β-[2-(4-chlorophenyl)-2-dichloroacetoxyimino-acetamido]-ceph-3em-4-carboxylate (syn-isomer)

was isolated as a yellow foam by Method B and was deprotected by Method F to give:

(b) 3-Acetoxymethyl-7β-[2-(4-chlorophenyl)-2-hydroxyimino-acetamido]-ceph-3-em-4-carboxylic acid (syn isomer)

as a solid (16% overall yield based on 7β-amino-ester), $[\alpha]_D+62°$ (c 1.0 DMSO), $\lambda_{max.}$ (pH 6 buffer) 258 nm (ε20,900), $\nu_{max.}$ (Nujol) 3280 (NH), 1770 (β-lactam), 1660 and 1524 cm.$^{-1}$ (CONH), τ (DMSO-d6) values include 0.33 (doublet J 9 Hz; NH) and 7.98 (singlet; OCOCH$_3$).

EXAMPLE 16

(a) t-Butyl 3-acetoxymethyl-7β-(2-dichloroacetoxyimino-2-naphth-1'-ylacetamido)ceph-3-em-4-carboxylate (syn-isomer)

was isolated as a solid (70%), $[\alpha]_D+32°$ (c 0.75, DMSO), $\lambda_{max.}$ (EtOH) 270 nm (ε 13,050), $\nu_{max.}$ (CHBr$_3$) 3540 (OH), 3380 (NH), 1784 (β-lactam), 1738 cm. (OCOCH$_3$), τ (CHCl$_3$) values include 3.68 (singlet; CHCl$_2$), 7.93 (singlet; OCOCH$_3$), 8.46 (singlet; C(CH$_3$)$_3$) by Method B. Deprotection by Method F gave:

(b)

3-Acetoxymethyl-7β-(2-hydroxyimino-2-naphth-1'-ylacetamido)ceph-3-em-4-carboxylic acid (syn-isomer) (97%), $[\alpha]_D + 44°$ (c 0.72, DMSO), $\lambda_{max.}$ (pH 6 phosphate buffer) 260 nm ($\epsilon$ 11,850), $\nu_{max.}$ (Nujol) 1770 (β-lactam), 1714 cm.$^{-1}$ (OCOCH$_3$), τ (DMSO-d6) values include 0.22 (doublet; J 9 Hz; NH), 1.3-2.5 (multiplet; aromatic protons), 7.94 (singlet; OCOCH$_3$).

EXAMPLE 17

7β-[2-Hydroxyimino-2-(thien-2-yl)acetamido]-3-(5-methyl-1,3,4-thiadiazol-2-yl)thiomethylceph-3-em-4-carboxylic acid (syn-isomer)

A solution of 2-dichloroacetoxyimino-2-(thien-2-yl)acetyl chloride 0.585 g.) in ethyl acetate (5 ml.) was added to a stirred suspension of diphenylmethyl 7β-amino-3-(5-methyl-1,3,4-thiadiazol-2-yl)thiomethylceph-3-em-4-carboxylate (1 g.) in ethyl acetate (10 ml.) and propylene oxide (1 ml.) at 20°. After 30 minutes all the solid had dissolved. The solution was washed with 2 N-hydrochloric acid, saturated sodium bicarbonate solution, water and brine, dried and concentrated to give crude diphenylmethyl 7β-[2-dichloroacetoxyimino-2-(thien-2-yl)acetamido]-3-(5-methyl-1,3,4-thiadiazol-2-yl)thiomethylceph-3-em-4-carboxylate (syn-isomer) as a solvated foam (1.567 g.) $\lambda_{max.}$ (EtOH) 267.5 nm ($E_1^1$ 240), τ values (CDCl$_3$) include 3.00 (singlet, —CHPh$_2$), 3.75 (singlet; CHCl$_2$) and 7.35 (singlet; CH$_3$).

Trifluoroacetic acid (8 ml.) was added to a solution of the above ester (1.387 g.) in anisole (2 ml.) at 20°. After 5 minutes the solution was concentrated under reduced pressure and the residue was dissolved in ethyl acetate. The solvent was evaporated and again the residue was dissolved in ethyl acetate. The solution was washed with water and then extracted with sodium bicarbonate solution. The combined extracts were washed with ethyl acetate, then taken to pH 1.9 with concentrated hydrochloric acid and extracted with ethyl acetate. The extract was washed with water and brine, dried and concentrated under reduced pressure to give a foam. Trituration with ether gave the title compound as a buff solid (0.50 g.), $[\alpha]_D - 84°$ (c 1, DMSO), $\lambda_{max.}$ (pH 6 buffer) 271.5 nm ($\epsilon$ 17,600), $\nu_{max.}$ (Nujol) include 3250 (NH), 1780 (β-lactam), 2600+1710 (CO$_2$H), and 1674+1548 cm.$^{-1}$ (CONH), τ values (DMSO-d$_6$) 0.24 (doublet; NH) 2.37 and 2.82 (thienyl protons) 4.12 (double doublet, J 5 and 8 Hz; C-7H), 4.76 (doublet, J 5 Hz; C-6H), 5.40 and 5.75 (2 doublets, branches of quartet, J 13 Hz; C-3 CH$_2$), 6.13+6.40 (2 doublets, branches of quartet, J 18 Hz; C-2 CH$_2$) and 7.29 (singlet; CH$_3$).

EXAMPLE 18

3-Acetoxymethyl-7β-(2-hydroxyimino-2-phenylacetamio)ceph-3-em-4-carboxylic acid (syn-isomer)

To a stirred solution of 3-acetoxymethyl-7β-aminoceph-3-em-4-carboxylic acid (2.72 g.) and sodium bicarbonate (1.85 g.) in water (50 ml.) and acetone (50 ml.) was added, dropwise with stirring at 5°, a solution of 2-dichloroacetoxyimino-2-phenylacetyl chloride (syn-isomer) in acetone (5 ml.) over a period of five minutes. The reaction was stirred for an hour at room temperature, after which the pH was 4.0. The acetone was removed under reduced pressure and the mixture was extracted with ethyl acetate. The extracts were washed with 2 N-hydrochloric acid and saturated brine, dried and concentrated to ca. 5 ml. The solution was cooled to −30° for fifteen minutes, filtered and the solid washed with cold ethyl acetate then petroleum spirit (b.p. 40°-60°) and dried to give the title acid as an ethyl acetate solvate (1.2 g; 23%), $[\alpha]_D + 64°$, $\lambda_{max.}$ (EtOH) 253 nm ($\epsilon$ 18,400), $\nu_{max.}$ (Nujol) 3260 (NH), 1760 (β-lactam), 1710 (acetate), 1650 and 1550 cm.$^{-1}$ (amide), τ (DMSO-d6) values include 0.33 (doublet J 9 Hz; NH), 2.3-2.65 (multiplet; aromatic protons), 7.96 (singlet; CH$_3$CO).

EXAMPLE 19

3-Acetoxymethyl-7β-(2-hydroxyimino-2-phenylacetamido)ceph-3-em-4-carboxylic acid (syn isomer)

To a suspension of 3-acetoxymethyl-7-aminoceph-3-em-4-carboxylic acid p-toluenesulphonic acid salt (4.8 g) in acetonitrile:dimethylacetamide (6:1, 25 ml.) was added dropwise with stirring at room temperature a 3 M solution of 2-dichloroacetoxyimino-2-phenylacetyl chloride (syn isomer) in acetonitrile (5 ml.). The reaction was stirred at room temperature until the solution was homogeneous, then poured into saturated aqueous sodium bicarbonate solution. The solution was washed with ethyl acetate, acidified to pH 1.0 (2 N-hydrochloric acid) and extracted with ethyl acetate. The combined extracts were washed with water, dried and concentrated to ca. 10 ml. The concentrate was added dropwise to petroleum spirit (b.p. 40°-60°) with vigorous stirring. This produced a gummy solid which was stirred with ethyl acetate (50 ml.) and the solution filtered and added dropwise to petroleum spirit (300 ml.). The precipitated solid was filtered and dried to give the title acid (1.47 g; 29%), $[\alpha]_D + 57°$ (c 0.7 DMSO) $\lambda_{max.}$ (EtOH) 253.5 nm ($\epsilon$ 15,800).

EXAMPLE 20

7β-(2-Hydroxyimino-2-phenylacetamido)-3-methylceph-3-em-4-carboxylic acid (syn-isomer)

A solution of hydroxylamine hydrochloride (34.8 mg.) in dry methanol (5 ml.) was neutralised to phenolphthalein with sodium methoxide in methanol. This solution was added to a solution of t-butyl-7β-phenylglyoxamido-3-methylceph-3-em-4-carboxylate (201 mg.) in dry methanol (10 ml.) and the mixture was stirred for 2 days at room temperature. The residue obtained by evaporation was dissolved in ethyl acetate (20 ml.) and the solution was washed with water, dried and evaporated to give a yellow froth (220 mg.). Preparative chromatography on silica plates developed with 20% v/v ethyl acetate in benzene led to isolation of the starting material (46 mg.), t-butyl-7β-(2-hydroxyimino-2-phenylacetamido)-3-methylceph-3-em-4-carboxylate (syn-isomer) (22 mg.) and a slow-running fraction (94 mg.) which did not contain a β-lactam ring. The required ester (20 mg.) was shaken with trifluoroacetic acid (1 ml.) at room temperature for 10 min. and then evaporated to give the title acid (15 mg.) which was identified with an authentic sample by thin layer chromatography and n.m.r. spectrum [τ (DMSO-d$_6$) includes 0.38 (doublet, J=8 Hz, NH of syn-isomer), 2.25-2.65 (multiplet; phenyl protons) and 7.95 (singlet; CH$_3$)].

The starting ester was prepared as follows: phenylglyoxylyl chloride (0.37 g.) was added to a solution of t-butyl 7β-amino-3-methylceph-3-em-4-carboxylate (0.54 g.) in ethyl acetate (10 ml.) and the solution was stirred at room temperature for 1.5 hr. when no starting material remained (t.l.c.). The reaction mixture was diluted with ethyl acetate and washed successively with saturated sodium hydrogen carbonate solution, water and brine. Evaporation of the dried organic layer gave an oil that slowly crystallised (0.80 g). Recrystallisation from cyclohexane gave t-butyl 7β-phenylglyoxamido-3-methylceph-3-em-4-carboxylate (0.49 g, 62%), m.p. 141°–143°, $[\alpha]_D$+122° (c 1, ethanol), $\nu_{max.}$ (CHBr$_3$) 1781 cm.$^{-1}$ (β-lactam), τ (CDCl$_3$) values include 1.5–1.75 (ortho aromatic protons), 2.0–2.7 (aromatic protons) 7.89 (singlet; CH$_3$), 8.45 (singlet; t-butyl).

EXAMPLE 21

N-[7β-(2-Hydroxyimino-2-phenylacetamido)-ceph-3-em-3-yl-methyl]-(4-carbamoylpyridinium)-4-carboxylate(syn-isomer)

A solution of 3-acetoxymethyl-7β-(2-hydroxyimino-2-phenylacetamido)-ceph-3-em-4-carboxylic acid (syn-isomer) (500 mg) and isonicotinamide (500 mg) in water (10 ml.) was heated at 70° for 1.5 hours. The solution was diluted with water, filtered to remove a small amount of dark insoluble material, and passed down a column of Bio-rad AG-1-X8 ion exchange resin (acetate form). The eluate was examined by electrophoresis at pH 1.9, which revealed that two components were present, both of which migrated towards the cathode. The faster moving component corresponded to isonicotinamide, the slower had a mobility similar to cephaloridine, and gave the expected purple colouration with iodoplatinate reagent. Evaporation of the eluate under reduced pressure at 35° gave a residue which was triturated with acetone and filtered. The solid was washed with acetone and dried, giving 140 mg. (25%) of the title compound. The material was homogeneous on electrophoresis at pH 1.9, and migrated towards the cathode. $[\alpha]_D$−44°(c 0.72, DMSO), $\lambda_{max.}$(EtOH) 251 nm (ε 13,000), $\nu_{max.}$(Nujol) 3330, 3150 (NH and OH), 1771 (β-lactam), 1680 and 1560 (CONH and 1606 cm.$^{-1}$ (CO$_2$—), τ (DMSO-d$_6$) values include 0.37, 1.50 [two doublets (branches of a quartet), J 7 Hz; p-disubstituted pyridine ring], 1.15 and 1.76 (two broad singlets; CONH$_2$), 2.3–2.7 (multiplet; aromatic protons), 4.26 (multiplet; C-7 H and C-3 CH$_2$), 4.8 (multiplet; C-6 H and C-3 CH$_2$), 6.40 and 6.88 [two doublets (branches of a quartet), J 18 Hz; C-2 CH$_2$].

EXAMPLE 22

N-[7β-(2-Hydroxyimino-2-phenylacetamido)-ceph-3-em-3-ylmethyl]-pyridinium-4-carboxylate (syn-isomer)

A solution of 3-acetoxymethyl-7β-(2-hydroxyimino-2-phenylacetamido)ceph-3-em-4-carboxylic acid (syn-isomer) (5.0 g) and pyridine (4 ml.) in water (100 ml.) was heated at 70° for 3 hours under an atmosphere of nitrogen. The reaction mixture was cooled and passed down a column of AG-1-X8 resin (acetate form) eluting with water. Fractions of 100 ml. were collected and those shown by electrophoresis to contain the required product were combined and lyophilised to give N-[7β-(2-hydroxyimino-2-phenylacetamido)ceph-3-em-3ylmethyl]pyridinium-4-carboxylate (syn-isomer) (0.75 g., 14%), $[\alpha]_D$−49.5° (c 0.83, DMSO), $\lambda_{max.}$ (pH 6 phosphate buffer) 255 nm (ε 20,500), $\nu_{max.}$ (Nujol) 1770 (β-lactam), 1660 and 1550 cm.$^{-1}$ (CONH), τ (DMSO-d$_6$) values include 0.46, 1.36 and 1.80 (pyridine ring protons), 2.3–2.7 (multiplet; aromatic protons).

EXAMPLE 23

(a) Diphenylmethyl 7β-(2-dichloroacetoxyimino-2-phenylacetamido)-3-(4,5-dimethoxycarbonyl-1,2,3-triazol-1-yl)-methylceph-3-em-4-carboxylate (syn-isomer)

To a solution of diphenylmethyl 3-azidomethyl-7β-(2-dichloroacetoxyimino-2-phenylacetamido)ceph-3-em-4-carboxylate (1.0 g.) in dioxan (40 ml.) was added dimethyl acetylenedicarboxylate (2.5 g.) and the solution was heated under reflux for four hours. The reaction was cooled, the solvent removed under reduced pressure and the residue triturated with petroleum spirit (b.p. 40°–60°). The resulting solid was collected, washed well with petroleum spirit and dried, to give the title ester. (1.2 g; 98%), $[\alpha]_D$+25° (c 1.1, DMSO), $\lambda_{max.}$ (EtOH) 250.5 nm. (ε 19,900), $\nu_{max.}$ (Nujol) 3380 (NH), 1790 (β-lactam), 1690 and 1515 cm.$^{-1}$ (CONH), τ (CDCl$_3$) values include 2.4–2.75 (multiplet; aromatic protons) 6.09, 6.21 (two singlets; methyl esters).

(b) 3-(4,5-Dimethoxycarbonyl-1,2,3-triazol-1-yl)methyl-7β-(2-hydroxyimino-2-phenylacetamido)ceph-3-em-4-carboxylic acid (syn-isomer)

To a solution of the above ester (1.0 g.) in anisole (8 ml.) was added trifluoroacetic acid (4 ml.). After standing for ten minutes at room temperature, the reaction mixture was evaporated to dryness, and benzene azeotroped from the residue which was then dissolved in ethyl acetate, extracted with sodium bicarbonate solution and the combined extracts were washed with ethyl acetate, acidified and extracted into ethyl acetate. The combined organic extracts were dried and concentrated to ca. 10 ml. The concentrate was added dropwise with stirring to petroleum (b.p. 40°–60°) and the resulting precipitate filtered and dried to give the title acid 0.5 g; 75%), $[\alpha]_D$+68° (c 0.7, DMSO), $\lambda_{max.}$ (pH 6 phosphate buffer) 249 nm. (ε 22,200), $\nu_{max.}$ (Nujol) 1790 (β-lactam), 1680 and 1540 cm.$^{-1}$ (amide), τ DMSO-d$_6$ values include 0.31 (doublet J 8 Hz; NH), 2.3–2.7 (multiplet; aromatic protons), 4.21 and 4.48 (two doublets, J 15 Hz; C-3 CH$_2$), 6.07 and 6.12 (singlets, methyl esters).

EXAMPLE 24

7β-(2-Hydroxyimino-2-phenylacetamido)-3-hydroxymethylceph-3-em-4-carboxylic acid sodium salt (syn-isomer)

To 3-acetoxymethyl-7β-(2-hydroxyimino-2-phenylacetamido)ceph-3-em-4-carboxylic acid (syn-isomer) (5.0 g) was added sufficient saturated sodium bicarbonate solution to bring the pH to 7.0, during which time solution occurred. To this solution was added water (300 ml.) and defatted wheat germ (35 g.), and the suspension stirred vigorously whilst the pH was maintained at between 6.7 and 6.9 by frequent additions of 2 N-sodium hydroxide. After addition of ca. 6 ml, the pH remained constant at 6.9. The mixture was poured into acetone (400 ml.), filtered (kieselguhr), and the filtrate evaporated under reduced pressure to remove acetone, then refiltered (kieselguhr). The filtrate was washed with ethyl acetate, and the pH adjusted to 2.8. The aqueous phase was extracted with ethyl acetate, and the extracts were stirred with water (ca. 300 ml.) and the pH brought up to 7.0 with 2 N sodium hydroxide. Th phases were separated and the aqueous phase washed twice with ethyl acetate, once with ether, evaporated under reduced pressure to remove residual solvents, and freeze-dried. This gave the title acid (1.5 g: 31%), $[\alpha]_D+93°$ (c 1.0, DMSO), $\lambda_{max.}$ (pH 6 phosphate buffer) 252 nm ($\epsilon$ 12,800), $\nu_{max.}$ (Nujol) 1750 ($\beta$-lactam), 1650 and 1530 cm.$^{-1}$ (amide), $\tau$ (DMSO-d$_6$) values include 2.3 to 2.6 (multiplet; aromatic protons), 5.72 and 6.05 [two doublets (branches of a quartet), J 13 Hz; CH$_2$OH], 6.44 and 6.68 [two doublets (branches of a quartet), J 18 Hz; C-2CH$_2$].

EXAMPLE 25

Sodium 7$\beta$-[2-hydroxyimino-2-(thien-2-yl)acetamiod]3-hydroxymethyl-ceph-3-em-4-carboxylate syn-isomer).

A solution of sodium 3-acetoxymethyl-7$\beta$-[2-hydroxyimino-2-(thien-2-yl)acetamido]ceph-3-em-4-carboxylate (syn-isomer) (2.0 g) in water (160 ml.) was warmed to 37° and defatted wheat germ (15 g.) was added. The mixture was stirred at 37° for 4 hours, the pH being kept between 6.5 and 6.9 by the addition of 2 N sodium hydroxide solution (total 2.3 ml.). The mixture was poured into acetone (200 ml.) and then filtered through kieselguhr. Acetone was removed under reduced pressure and the aqueous solution was again filtered through kieselguhr, washed with ethyl acetate, then covered with ethyl acetate and taken to pH 2.7 by the careful addition of concentrated hydrochloric acid. The layers were separated and the aqueous layer was re-extracted with ethyl acetate. The combined extracts were washed with water and the pH was taken to 7.0 by the addition of 2 N-sodium hydroxide. The organic layer was further extracted with water and the combined aqueous solution was washed with ethyl acetate and ether, degassed and lyophilised to give the title oxime as a brown solid (1.43 g; 79%), $[\alpha]_D+76°$ (c 0.46, DMSO), $\lambda_{max.}$ (pH 6 phosphate) 261.5 nm ($\epsilon$ 10,600), $\lambda_{inflex.}$ 284 nm ($\epsilon$ 6,500), $\nu_{max.}$ (Nujol) 1760 ($\beta$-lactam), 1560 (CO$_2^-$), 1650 and 1520 cm$^{-1}$ (CONH), $\tau$ (D$_2$O) values include 2.41, 2.63 and 2.83 (doublet, doublet and triplet respectively, J 4 Hz; thienyl protons)

EXAMPLE 26

(a)

7$\beta$.(2-Acetoxyimino-2-phenylacetamido)-3-acetoxymethylceph-3-em-4-carboxylic acid To a solution of acetyl chloride (8 ml.) in methylene chloride (8 ml.) was added 3-acetoxymethyl-7$\beta$-(2-hydroxyimino-2-phenylacetamido)-ceph-3-em-4-carboxylic acid (syn-isomer) (500 mg.) in portions over ten minutes with vigorous stirring at room temperature. A gum formed, and ethyl acetate (8 ml.) was added to achieve solution. After stirring for two hours at room temperature, the mixture was added slowly to petroleum spirit (300 ml.) with vigorous stirring. The precipitate was filtered off, washed thoroughly with petroleum spirit, dissolved in chloroform (10 ml.) stirred with activated charcoal and filtered. The filtrate was added dropwise to petroleum spirit (250 ml.) with stirring. The precipitate was filtered off and dried giving the title acid, (350 mg; 62%), $\tau$ (DMSO-d$_6$) values include −0.11 (doublet, J 8 Hz; NH), 2.2–2.6 (multiplet; aromatic protons), 7.76 (singlet; CH$_3$.CO$_2$N—), 7.94 (singlet; CH$_3$CO). Signals at $\tau$ 0.05 (doublet; J 9 Hz; NH) and 7.78 (singlet; CH$_3$CO$_2$N—) indicated the presence of about 30% of the anti-isomer.

(b)

7$\beta$-(2-Acetoxyimino-2-phenylacetamido)-3-acetoxymethylceph-3-em-4-carboxylic acid (syn-isomer)

To a solution of pyridine (1.5 ml.) in ethyl acetate (20 ml.) was added 3-acetoxymethyl-7$\beta$-(2-hydroxyimino-2-phenylacetamido)ceph-3-em-4-carboxylic acid (syn-isomer) (0.5 g.) and the stirred mixture was treated dropwise with a solution of acetyl chloride (1.0 ml.) in ethyl acetate (5 ml.) and stirring continued for ten minutes. The mixture was poured into water, the ethyl acetate phase separated and washed with 2 N-hydrochloric acid, water, and extracted with saturated aqueous sodium bicarbonate. The combined aqueous extracts were acidified and extracted with ethyl acetate and the extracts were dried and concentrated to ca. 5 ml. The concentrate was added dropwise with stirring to petroleum (250 ml.). The precipitated solid was collected and dried, giving the title acid (0.32 g; 58%), $[\alpha]_D+83°$ (c C.8, DMSO), $\lambda_{max.}$ (pH 6 buffer) 258 nm ($\epsilon$ 20,800), $\nu_{max.}$ (Nujol) 3270 (NH), 1780 ($\beta$-lactam), 1680 and 1546 cm.$^{-1}$ (CONH), $\tau$ (DMSO-d$_6$) values include −0.10 (doublet J 8 Hz; NH), 2.2 to 2.6 (multiplet; aromatic protons), 7.78 (singlet; —N.O.COCH$_3$), 7.94 (singlet; OCOCH$_3$).

EXAMPLE 27

3-Acetoxymethyl-7$\beta$-(2-chloroacetoxyimino-2-phenylacetamido)-ceph-3-em-4-carboxylic acid (syn-isomer)

To a solution of chloroacetyl chloride (7 ml.) in ethyl acetate (7 ml.) was added portionwise with stirring 3-acetoxymethyl-7$\beta$-(2-hydroxyimino-2-phenylacetamido)-ceph-3-em-4-carboxylic acid (syn-isomer) (0.488 g.) and the resulting solution was allowed to stand at room temperature for two hours. It was then poured into petroleum (b.p. 40°–60°; 300 ml.) with vigorous stirring. The resulting solid was washed several times with petroleum ether, filtered, washed again with petroleum ether and dried to give the title acid as a yellow solid (0.453 g; 79%), $[\alpha]_D+52°$ (c 0.87, DMSO), $\lambda_{max.}$ (pH 6 phosphate buffer) 254 nm ($\epsilon$ 16,700), $\nu_{max.}$ (CHBr$_3$) 3421 (NH), 17°1 ($\beta$-lactam), 1699 and 1521 cm.$^{-1}$ (CONH), $\tau$ (DMSO-d$_6$) values include −0.13 (doublet, J 8 Hz, NH), 5.36 (singlet; CH$_2$Cl), 7.96 (singlet; OCOCH$_3$)

EXAMPLE 28

3-Acetoxymethyl-7$\beta$-(2-ethoxycarbonyloxyimino-2-phenylacetamido)-ceph-3-em-4-carboxylic acid (syn-isomer)

A solution of 3-acetoxymethyl-7$\beta$-(2-hydroxyimino-2-phenylacetomido)ceph-3-em-4-carboxylic acid (syn-isomer) (0.5 g.) in saturated sodium bicarbonate solution (20 ml.) was shaken briefly with a solution of ethyl chloroformate (1 ml.) in ethyl acetate (10 ml.). The aqueous layer was separated and shaken with a second solution of ethyl chloroformate (1 ml.) in ethyl acetate (10 ml), then separated, washed twice with ethyl acetate, acidified and extracted with ethyl acetate. The combined aqueous extracts were dried and concentrated to ca. 5 ml. The concentrate was added dropwise with stirring to petroleum (200 ml.). The precipitate was filtered and dried to give the title acid (0.45 g., 77%), $[\alpha]_D+48°$ (c 0.8, DMSO), $\lambda_{max.}$ (pH 6 phosphate buffer (258 nm ($\epsilon$ 21,800), $\nu_{max.}$ (Nujol) 3270 (NH), 1776 ($\beta$-lactam), 1679 and 1535 cm.$^{-1}$ (CONH), $\tau$ (DMSOd6) values include −0.13 (doublet, J 8 Hz; NH), 2.2 to 2.5 (multiplet; aromatic protons). 5.68 (quartet, J 8 Hz; OCH₂CH₃), 7.96 (singlet; OCOCH₃), 8.70 (triplet; J 8 Hz; OCH₂CH₃).

EXAMPLE 29

(a) Diphenylmethyl 3-acetoxymethyl-7β-(2-benzoyloxyimino-2-phenylacetamido)-ceph-3-em-4-carboxylate (syn-isomer)

To a solution of diphenylmethyl 3-acetoxymethyl-7β-(2-hydroxyimino-2-phenylacetamido)ceph-3-em-4-carboxylate (1.0 g) and pyridine (1.5 ml.) in ethyl acetate (30 ml.) was added benzoyl chloride (1.5 ml.) and the mixture allowed to stand for one hour at room temperature. The solution was then washed with 2 N-hydrochloric acid (50 ml.) and saturated brine, dried (sodium sulphate) and concentrated to ca. 5 ml. The concentrate was added dropwise to petroleum (b.p. 40°–60°; 350 ml.) and the precipitated solid filtered, washed with petroleum and dried, yielding the title ester as a yellow solid (1.0 g; 85%), $[\alpha]_D + 6.4°$ (c 0.94, DMSO), $\lambda_{max.}$ (EtOH) 259 nm ($\epsilon$ 26,700), $\nu_{max.}$ (CHBr₃) 1780 (β-lactam), 1640 and 1522 cm.⁻¹ (CONH), $\tau$ (DMSO-d₆) values include −0.27 (doublet J 8 Hz; NH), 1.8–2.8 (multiplet; aromatic protens), 8.01 (singlet; OCOCH₃).

(b) 3-Acetoxymethyl-7β-(2-benzoyloxyimino-2-phenylacetamido)ceph-3-em-4-carboxylic acid (syn-isomer)

A solution of diphenylmethyl 3-acetoxymethyl-7β-(2-benzoyloxyimino-2-phenylacetamido)ceph-3-em-4-carboxylate (syn-isomer) (0.85 g) in trifluoroacetic acid (10 ml.) and anisole (10 drops) was allowed to stand for ten minutes at room temperature, then evaporated to dryness under reduced pressure. The residue was dissolved in ethyl acetate and extracted with sodium bicarbonate. The combined extracts were acidified (2 N-hydrochloric acid) and extracted with ethyl acetate. The combined organic extracts were washed with brine, dried, concentrated to ca. 10 ml.; and added dropwise with stirring to petroleum. The precipitated solid was filtered and dried to give the title acid (0.39 g; 60%), $[\alpha]_D + 31°$ (c 0.94 DMSO), $\lambda_{max.}$ (EtOH) 260 nm ($\epsilon$ 26,000), $\nu_{max.}$ (Nujol) 3270 (NH), 1784 cm.⁻¹ (β-lactam), $\tau$ (DMSO-d₆) values include −0.27 (doublet J 8 Hz; NH), 1.75–2.6 (multiplet; aromatic protons) 7.96 (singlet; OCOCH₃).

The starting material used in (a) above was prepared as follows:

To a solution of 3-acetoxymethyl-7β-(2-hydroxyimino-2-phenylacetamido)ceph-3-em-4-carboxylic acid (syn-isomer)(2.0 g) in tetrahydrofuran (50 ml.) maintained at 37° was added portionwise a solution of diphenyldiazomethane in petroleum (b.p. 60°–80°) until the purple colour persisted for one hour. After addition of acetic acid to destroy excess diphenyldiazomethane, the solution was evaporated to dryness, taken up in ethyl acetate, then washed with sodium bicarbonate, and brine, dried and evaporated. The residue was triturated with petroleum spirit, and the resulting solid filtered and dried to give diphenylmethyl 3-acetoxymethyl-7β-(2-hydroxyimino-2-phenylacetamido)ceph-3-em-4-carboxylate (syn-isomer) (1.93 g 69%), $[\alpha]_D + 24°$ (c 1, DMSO), $\lambda_{max.}$ (EtOH) 253 nm ($\epsilon$ 16,150), $\nu_{max.}$ (CHBr₃) 3610 (OH), 1796 cm.⁻¹ (β-lactam), $\tau$ (DMSO-d₆) values include 0.27 (doublet, J 9 Hz; NH), 8.03 (singlet; OCOCH₃).

EXAMPLE 30

(a) Diphenylmethyl 3-acetoxymethyl-7β-[2-(4-nitrobenzoyloxyimino]-2-phenylacetamido)ceph-3-em-4-carboxylate (syn-isomer)

To a solution of diphenylmethyl 3-acetoxymethyl-7β-(2-hydroxyimino-2-phenylacetamido)ceph-3-em-4-carboxylate (syn-isomer) (1.5 g.) and pyridine (0.5 ml.) in ethylacetate (100 ml.) was added 4-nitrobenzoyl chloride (0.42 g) and the resulting solution was stirred at room temperature for one hour. Further portions (0.042 g 0.015 g and 0.20 g.) of the acid chloride were added, and the reaction stirred for a total of 4 hours at room temperature. Then the solution was washed with 2 N-hydrochloric acid and brine, dried, concentrated to ca. 5 ml. and added dropwise with stirring to petroleum spirit (b.p. 40°–60°). This gave a solid which was filtered and dried, yielding the title ester (1.1 g; 58%), $\lambda_{max.}$ (EtOH) 263 nm ($\epsilon$ 29,000), $\nu_{max.}$ (CHBr₃) 3400 (NH), 1780 (β-lactam), 1395 and 1525 (NO₂), 1687 and 1515 cm.⁻¹ (CONH), $\tau$ (CDCl₃) values include 1.70 and 2.71 (two doublets, J 8 Hz;

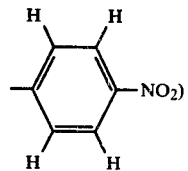

2.1–2.85 (multiplet; aromatic protons), 8.03 (singlet; OCOCH₃)

(b) 3-Acetoxymethyl-7β-[2-(4-nitrobenzoyloxyimino)-2-phenylacetamido]-ceph-3-em-4-carboxylic acid (syn-isomer)

A solution of diphenylmethyl 3-acetoxymethyl-7β-[2-(4-nitrobenzoyloxyimino)-2-phenylacetamido]ceph-3-em-4-carboxylate (syn-isomer) (1.0 g) in trifluoroacetic acid (10 ml.) was allowed to stand at room temperature for ten minutes. After evaporation of trifluoroacetic acid under reduced pressure, the residue was dissolved in ethyl acetate and extracted with saturated aqueous sodium bicarbonate. A solid precipitated during the bicarbonate extraction and was collected, washed with water and ethyl acetate, and partitioned between ethyl acetate and 2 -N-hydrochloric acid. The phases were separated and the upper layer was washed with water, dried, concentrated to ca. 10 ml. and added dropwise with stirring to petroleum (b.p. 40°–60°; 200 ml.). The precipitated solid was filtered and dried to give 3-acetoxymethyl-7β-[2-(4-nitrobenzoyloxyimino)-2-phenylacetamido]ceph-3-em-4-carboxylic acid (syn-isomer) (0.150 g; 20%), $[\alpha]_D + 17°$ (c 0.8, DMSO), $\lambda_{max.}$ (EtOH) 266.5 nm ($\epsilon$ 33,000), $\nu_{max.}$ (Nujol) 3270 (NH), 1780 (β-lactam) 1520 and 1338 (NO₂), 1675 and 1520 cm.⁻¹ (CONH), $\tau$ (DMSO-d₆) values include 1.58 and 1.69 (two doublets J 8 Hz; p-substituted phenyl), 2.1 to 2.5 (multiplet; aromatic protons), 7.79 (singlet; OCOCH₃).

EXAMPLE 31

3-Acetoxymethyl-7β-(2-ethylcarbamoyloxyimino-2-phenylacetamido)ceph-3-em-4-carboxylic acid (syn-isomer).

To ethyl isocyanate (5 ml.) was added 3-acetoxymethyl-7β-(2-hydroxyimino-2-phenylacetamido)ceph-3-em-4-carboxylic acid ethyl acetate solvate (syn-isomer) (0.9 g.) and the mixture stirred for one hour at room temperature. Two further portions of the isocyanate (5 ml.) were added, over a period of two hours. The mixture was then allowed to stand for one hour, and poured into petroleum (b.p. 40°-60°; 250 ml.) and the resulting precipitate collected, washed thoroughly with petroleum and dried. The solid was dissolved in ethyl acetate and extracted into sodium bicarbonate solution; the bicarbonate solution was then washed with ethyl acetate, acidified (2 N-hydrochloric acid) and extracted with ethyl acetate. The combined extracts were dried and concentrated, and the concentrate (ca. 5 ml.) added dropwise to petroleum spirit with vigorous stirring. The precipitate formed was filtered and dried, giving the title acid (0.4 g.; 47%), $[\alpha]_D+50°$ (c 0.85, DMSO), $\lambda_{max.}$ (pH 6 buffer) 257.5 nm ($\epsilon$ 21,200), $\nu_{max.}$ (Nujol) 1782 (β-lactam), 1675 and 1520 cm.$^{-1}$ (CONH), $\tau$ (DMSO-$d_6$) values include 0.04 (doublet J 8 Hz; NH), 2.0–2.6 (multiplet; aromatic protons), 6.7–7.1 (multiplet; $NHCH_2CH_3$) and 8.89 (triplet, J 9 Hz; $CH_2CH_3$).

EXAMPLE 32

3-Acetoxymethyl-7β-[2-(2-chloroethyl)carbamoyloxyimino-2-phenylacetamido]-ceph-3-em-4-carboxylic acid (syn-isomer)

To a solution of 3-acetoxymethyl-7β-(2-hydroxyimino-2-phenylacetamido)ceph-3-em-4-carboxylic acid ethyl acetate solvate (syn-isomer) (1.0 g.) in dimethylformamide (21 ml.) containing triethylamine (0.425 g) was added 2-chloroethylisocyanate (0.274 g.) and the mixture was stirred at room temperature for one hour. The reaction mixture was acidified (2 N hydrochloric acid) and extracted with ethyl acetate. The extracts were combined and extracted with saturated aqueous sodium bicarbonate. The combined aqueous extracts were acidified (2 N-hydrochloric acid) and extracted with ethyl acetate, dried, concentrated and added dropwise to petroleum with vigorous stirring. The precipitated solid was filtered, dissolved in ethyl acetate (10 ml.) and added dropwise to petroleum (300 ml.). The precipitate was filtered and dried giving the title acid (0.76 g; 74%), $[\alpha]_D+28°$ (c 1.0 DMSO), $\lambda_{max.}$ (pH 6 phosphate buffer) 257.5 nm. ($\epsilon$ 20,780), $\nu_{max.}$ (Nujol) 3270 (NH), 1780 (β-lactam), 1660 and 1520 cm.$^{-1}$ (amide), $\tau$ (DMSO-$d_6$) values include $-0.10$ (doublet, J 8 Hz; NH), 6.2–6.7 (multiplet; C-2 $CH_2+$—$CH_2CH_2Cl$), 7.95 (singlet; $OCOCH_3$).

EXAMPLE 33

6β-(2-Hydroxyimino-2-phenylacetamido)-2,2-dimethylpenam-3α-carboxylic acid (syn-isomer)

To a suspension of 6β-amino-2,2-dimethylpenam-3α-carboxylic acid (1.08 g) in chloroform (25 ml.) was added hexamethyldisilazane (2.49 g) and the mixture was heated under reflux for two hours, during which time solution occurred. The solvents were removed under reduced pressure, giving trimethylsilyl 2,2-dimethyl-6β-trimethylsilylaminopenam-3α-carboxylate as a solid. The solid was dissolved in methylene chloride (20 ml.) and propylene oxide (1.5 ml.) added. The solution was cooled to 0° and treated dropwise with 2-dichloroacetoxyimino-2-phenylacetyl chloride (from 1.38 g. 2-dichloroacetoxyimino-2-phenylacetic acid (syn-isomer)) in methylene chloride (20 ml.), over a period of fifteen minutes with stirring. The solution was allowed to stir for two hours at room temperature. The solvents were evaporation under reduced pressure below 35°, and the residue taken up in ethyl acetate. After addition of methanol (2 ml.), the solution was extracted as rapidly as possible with ice-cold sodium bicarbonate solution and the combined extracts washed with ethyl acetate and poured into a stirred mixture of ethyl acetate and 2 N-hydrochloric acid. The organic phase was separated and combined with an ethyl acetate extraction of the aqueous phase, and the solution washed with water, dried and evaporated. The residue was taken up in ethyl acetate (5 ml.) and added dropwise to petroleum (b.p. 40°-60°; 200 ml.). The precipitated solid was filtered and dried, giving 6β-(2-hydroxyimino-2-phenylacetamido)-2,2-dimethylpenam-3α-carboxylic acid (syn-isomer) (0.84 g; 46%), $[\alpha]_D+210°$ (c 0.9, DMSO), $\lambda_{max.}$ (EtOH) 251 nm ($\epsilon$ 9,450), $\nu_{max.}$ (Nujol) 3650- 2300 (OH), 3280 (NH), 1758 (β-lactam), 1735 ($CO_2H$), 1650 and 1510 cm.$^{-1}$ (CONH), $\tau$ (DMSO-$d_6$) 0.51 (doublet, J 7 Hz; NH), 2.2–2.7 (multiplet; aromatic protons), 4.28 (quartet, J 4 Hz and 7 Hz; C-6H), 4.40 (doublet J 4 Hz; C-5H), 5.27 (singlet; C-3H), 8.39 and 8.48 (two singlets; methyl groups).

EXAMPLE 34

Benzyl 2-phenylethylammonium 3-acetoxymethyl-7β-(2-hydroxyimino-2-phenylacetamido)ceph-3-em-4-carboxylate (syn-isomer)

To a solution of sodium bicarbonate (0.084 g.) in water (20 ml.) was added 3-acetoxymethyl-7β-(2-hydroxyimino-2-phenylacetamido)ceph-3-em-4-carboxylic acid ethyl acetate solvate (0.507 g.) and the resulting solution was treated with a solution of benzyl 2-phenylethyl ammonium acetate (0.396 g.) in water (10 ml.). A white solid separated, and after stirring for fifteen minutes it was filtered, washed with water and dried to give the title salt (0.2 g; 32%), $\lambda_{max.}$ (pH 6 phosphate buffer) 254 nm ($\epsilon$ 18,000), $\nu_{max.}$ (Nujol) 1773 (β-lactam) 1650 and 1550 cm.$^{-1}$ (CONH), $\tau$ (DMSO-$d_6$) values include 0.4 (doublet, J 8 Hz; NH), 2.3–2.71 (multiplet; aromatic protons), 7.99 (singlet; $OCOCH_3$).

EXAMPLE 35

2,2-Dimethyl-6β-[2-hydroxyimino-2(thien-2-yl)acetamido]-penam-3α-carboxylic acid (syn-isomer)

A solution of trimethylsilyl 2,2-dimethyl-6β-trimethylsilylaminopenam-3α-carboxylate [prepared from the corresponding amino-acid (0.864 g.)] and propylene oxide (1 ml.) in dichloromethane (20 ml.) was cooled to 0° and treated dropwise with a solution of 2-dichloroacetoxyimino(thien-2-yl)acetyl chloride syn-isomer; [prepared from the corresponding acid (0.753 g.)] in dichloromethane (12 ml.) The resuling solution was maintained at 0° for 1 hour and was then evaporated to a small bulk and partitioned between ethyl acetate and saturated sodium bicarbonate solution. The aqueous phase was washed with ethyl acetate, acidified with 2 N-hydrochloric acid, and extracted with ethyl acetate. The dried organic solution was evaporated to a small bulk and added dropwise to stirred petroleum spirit (b.p. 40°-60°). The resulting precipitate was collected, washed, and dried to afford the title acid (0.337 g., 24% based on amine), $[\alpha]_D+224°$ (c 0.57, DMSO), $\lambda_{max}$. (pH 6 buffer) 288 nm ($\epsilon$ 6,400), $\lambda$ inf. 270 nm ($\epsilon$ 5,800), $\nu_{max}$. (Nujol), 2600 and 1730 ($CO_2H$), 1776 ($\beta$-lactam), 1670 and 1526 cm.$^{-1}$ (CONH), $\tau$ ($d_6$-DMSO) values include 0.44 (d, J 6 Hz; NH), 2.45 and 2.9 (multiplets, aromatic protons), 5.78 (s; C-3H), 8.46 and 8.55 (2 s; $CH_3$ groups).

EXAMPLE 36

2,2-Dimethyl-6β-[2-hydroxyimino-2-(thien-3-yl)acetamido]penam-3α-carboxylic acid (syn-isomer)

To a cold solution of trimethylsilyl 2,2-dimethyl-6β-trimethylsilylamino-penam-3α-carboxylate [made from 6β-amino-2,2-dimethyl-penam-3α-carboxylic acid (0.43 g) and hexamethyldisilazane (2.1 mls.)] and propylene oxide (0.53 mls.) in dry methylene chloride (10 mls.) was added dropwise with stirring a solution of 2-dichloroacetoxyimino-2-thien-3-yl) acetyl chloride (syn-isomer) (2.1 mmoles) in dry methylene chloride. After 1 hr. at 20° C. the reaction was evaporated and the residue dissolved in ethyl acetate. The ethyl acetate solution was extracted with ice-cold saturated sodium bicarbonate solution. The combined aqueous phases were acidified to pH 1 with 2 N-hydrochloric acid and extracted with ethyl acetate. After drying the extracts were evaporated to a small volume which on adding to an excess of petrol (b.p. 40°-60°) gave a white solid which was filtered and dried to yield the title compound (0.32 g, 44%), $[\alpha]_D= +220°$ (c 0.9, dioxan), $\lambda_{max}$. (pH 6 buffer) 256 nm ($\epsilon$ 9,100), $\nu_{max}$. (Nujol) 3300 (NH), 1770 (β-lactam), 1740 and 2600 (COOH) and 1660 and 1526 cm.$^{-1}$ (CONH) $\tau$ (DMSO $d_6$) includes 0.46 (d; J 8 Hz; NH) 2.30, 2.35, 2.59 (m; thienyl protons), 5.66 (s; C-3H), and 8.35 and 8.44 (2s; $CH_3$ groups).

EXAMPLE 37

2,2-Dimethyl-6β-[2-hydroxyimino-2(fur-2-yl)acetamido]-penam-3α-carboxylic acid (syn-isomer)

A solution of trimethylsilyl 2,2-dimethyl-6β-trimethylsilyaminopenam-3α-carboxylate [prepared from the corresponding amino-acid (0.648 g.)] and propylene oxide (0.75 ml.) in dichloromethane (15 ml.) was cooled to 0° and treated dropwise with a solution of 2-dichloroacetoxyimino(fur-2-yl)acetyl chloride [syn-isomer; prepared from the corresponding acid (0.579 g.)] in dichloromethane (12 ml.). The resulting solution was maintained at 0° for 1 hour and was then evaporated to small volume and partitioned between ethylacetate and saturated sodium bicarbonate solution. The aqueous phase was washed with ethyl acetate, acidified with 2 N-hydrochloric acid and extracted with ethyl acetate. The dried organic solution was evaporated to a small bulk and added dropwise to stirred petroleum spirit (b.p. 40°-60°). The resulting precipitate was collected, washed and dried to give the title acid (0.56 g., 55% based on amine), $[\alpha]_D+243°$ (c 0.93, DMSO), $\lambda_{max}$. (pH 6 buffer) 275 nm ($\epsilon$ 9,600), $\nu_{max}$. (Nujol), 1778 (β-lactam), 1740 and 2600 ($CO_2H$), 1670 and 1528 cm.$^{-1}$ (CONH), $\tau$ ($d_6$-DMSO) values include 0.44 (d, J 6 Hz; NH) 2.18 and 3.34 (multiplets; aromatic protons), 5.70 (s; C-3H), 8.36 and 8.46 (2s; $CH_3$ groups).

EXAMPLE 38

3-Acetoxymethyl-7β-[2-hydroxyimino-2-(thien-3-yl)acetamido]ceph-3-em-4-carboxylic acid (syn-isomer)

To an ice cold solution of t-butyl 3-acetoxymethyl-7β-aminoceph-3-em-4-carboxylate (1.59 g) and propylene oxide (3.5 mls) in ethyl acetate (15 mls) was added with stirring a 1-M solution of 2-dichloroacetoxyamino-2-(thien-3-yl) acetyl chloride (syn-isomer) (5.3 ml.) in ethyl acetate. After 1½ hrs. at 20° C. the solution was washed with 2N-HCl, saturated sodium bicarbonate solution and brine. The organic layer was dried and evaporated to give t-butyl 3-acetoxymethyl-7β-[2-dichloroacetoxyimino-2-(thien-3-yl)acetamido]ceph-3-em-4-carboxylate (syn-isomer) as a white foam, (2.8 g, 100%), $[\alpha]_D+47.0°$ (c 0.9, DMSO), $\lambda_{max}$. (ethanol) 253 nm ($\epsilon$ 13,900), $\nu_{max}$. ($CHBr_3$) 3580 (OH), 3410 (NH), 1790 (β-lactam), 1728 ($OCOCH_3$), 1720 ($COO$ $Bu^t$) and 1700 and 1520 cm.$^{-1}$ (CONH); $\tau$ ($CDCl_3$) values include 2.11 to 2.7 (m; thienyl protons), 7.92 (s; $OCOCH_3$), 8.48 (s; $Bu^t$).

A solution of the t-butyl ester (2.7 g.) in trifluoroacetic acid (25 mls.) was allowed to stand for 15 mins. when it was evaporated and the residue azeotroped with benzene. The oil was dissolved in ethyl acetate and extracted with saturated sodium bicarbonate solution. The aqueous solution was acidified to pH 1 with 2 N-HCl and extracted with ethyl acetate. The combined organic phases were dried and evaporated to a small volume which on adding to an excess of petrol (b.p. 40°-60°) gave a white solid which was filtered and dried yielding 3-acetoxymethyl-7β-[2-hydroxyimino-2-(thien-3-yl)acetamido]ceph-3-cm-4-carboxylic acid (syn-isomer) (1.5 g, 60.3%) $[\alpha]_D= +50.5°$ (c 0.88, DMSO), $\lambda_{max}$. (phosphate buffer pH 6) 256.5 nm ($\epsilon$ 18,350), $\nu_{max}$ (Nujol) 3280 (NH and OH), 1770 (β-lactam), 1726 ($OCOCH_3$), 1662 and 1522 (CONH) cm$^{-1}$ $\tau$ (DMSO $d_6$) values include 0.36 (d; J 8 Hz; —NH—), 2.3 to 2.7 (m; thienyl protons), 4.12 (dd; J 8, 5 Hz; 7H), 4.77 (d, J 5 Hz; 6H), 7.96 (s, $OCOCH_3$).

EXAMPLE 39

3-Acetoxymethyl-7β-[2-hydroxyimino-2-(fur-2-yl)acetamido]-ceph-3-em-4-carboxylic acid (syn-isomer)

To an ice cold solution of t-butyl 3-acetoxymethyl-7β-aminoceph-3-em-4-carboxylate (1.76 g.) and propylene oxide (4 mls) in ethyl acetate (15 mls) was added with stirring a 1-M solution of syn-2-dichloroacetoxyimino-2-(fur-2-yl)acetyl chloride in ethyl acetate (5.37 ml). After 1 hr at 20° C. the solution was washed successively with 2 N-HCl, saturated sodium bicarbonate solution and brine. The organic layer was dried and evaporated to give the t-butyl ester (syn-isomer) as a yellow foam, (3.04 g., 100%), $[\alpha]_D= +65.5°$ (c 0.9 DMSO), $\lambda_{max}$ (ethanol) 270 nm (c $\epsilon$ 16,700), $\nu_{max}$. ($CHBr_3$), 3300 (NH), 1780 (β-laciam), 1726 ($OCOCH_3$ and $COO^tBu$), and 1680 and 1530 cm.$^{-1}$ (CONH), $\tau$ ($CDCl_3$) values include 2.31, 2.88 and 3.39 (multiplets, furyl protons), 3.76 (s; $CHCl_2$), 7.92 (s; $OCOCH_3$), 8.48 (s; $Bu^t$).

A solution of the above t-butyl acetoxymethyl-7β-[2-dichloroacetoxyimino-2-(fur-2-yl)-acetamido]-ceph-3-em-4-carboxylate (syn-isomer) (2.94 g.) in trifluoroacetic acid (20 mls) was allowed to stand for 15 mins. when the solvent was evaporated and the residue azeotroped with benzene. The oil was dissolved in ethyl acetate and extracted with saturated sodium bicarbonate solution. The aqueous solution was acidified to pH 1 with 2 N-hydrochloric acid and extracted with ethyl acetate. The combined organic phases were dried and evaporated to a small volume which on adding to an excess of petrol (b.p. 40°–60°) gave a white solid which was filtered and dried to yield 3-acetoxymethyl-7β-[2-hydroxyimino-2-(fur-2-yl)acetamido]ceph-3-em-4-carboxylic acid, (1.68 g, 76%) $[\alpha]_D +69°$ (c 1.2, DMSO), $\lambda_{max}$ (pH 6 buffer) 269 nm ($\epsilon$ 16,300), $\nu_{max.}$ (Nujol) 1782 (β-lactam), 1728 (OCOCH$_3$), 1720 and 2600 (—COOH), and 1680 and 1536 cm$^{-1}$ (CONH), $\tau$ (DMSO-d$_6$) values include 0.33 (d, J 8 Hz; NH), 2.19 and 3.36 (2s; furyl protons), 6.28 and 6.52 (2 doublets, branches of quartet, J 18 Hz; C-2CH$_2$) and 7.95 (s; OCOCH$_3$).

EXAMPLE 40

3-Acetylthiomethyl-7β-[2-hydroxyimino-2-(thien-2-yl)acetamido]ceph-3-em-4-carboxylic acid (syn-isomer)

Diphenylmethyl 3-acetylthiomethyl-7β-aminoceph-3-em-4-carboxylate hydrochloric (1.03 g) was partitioned between ethyl acetate (30 ml) and aqueous sodium bicarbonate solution (30 ml.). The ethyl acetate layer was separated, washed with saturated sodium chloride solution, dried and filtered. The resulting solution was treated with 1-M solution of 2-dichloroacetoxyimino-2-(thien-2-yl)-acetyl chloride (syn-isomer) in ethyl acetate (2.15 ml.) and propylene oxide (0.5 ml.) and stirred at 21° for 40 mins, during which time a white precipitate appeared and re-dissolved. The solution was washed successively with aqueous sodium bicarbonate solution, water, saturated sodium chloride solution and dried. Removal of the solvent in vacuo gave an off-white froth (1.42 g). This was dissolved in anisole (2 ml.) and trifluoroacetic acid (⅞ ml.) added. After 5 min. at 10°, the reagents were removed in vacuo and the resulting gum partitioned between ethyl acetate and aqueous sodium bicarbonate solution. The organic layer was re-extracted with sodium bicarbonate solution and the combined aqueous layers were washed with ethyl acetate. The aqueous layer was adjusted to pH 2.0 with hydrochloric acid (2 N) and extracted with ethyl acetate. The extracts were washed with saturated sodium chloride solution, dried, and the solvent removed in vacuo to give the title compound as a pale brown froth (0.97 g) $[\alpha]_D -52°$ (c 1.04, DMSO), $\lambda_{max}$ (pH 6 buffer) 266 nm ($\epsilon$13,400) $\nu_{max.}$ (Nujol) 2600,1720 (CO$_2$H), 1770 (β-lactam), 1740 (SCOCH$_3$), 1660 and 1520 cm.$^{-1}$ (CONH), $\tau$ (DMSO-d$_6$) values include 0.30 (d, J 9; NH), 2.40, 2.84 (m, thien-2-yl), 7.66 (s; SCOCH$_3$).

The ester used as starting material for the above acylation was prepared as follows:

(a) Diphenylmethyl 3-acetylthiomethyl-7β-formamidoceph-3-em-4-carboxylate, 1β-oxide A solution of diphenylmethyl 3-bromomethyl-7β-formamidoceph-3-em-4-carboxylate, 1β-oxide (5.0 g) in N,N-dimethylformamide (30 ml.) was treated with ethanethiolic acid (4.0 ml) and triethylamine (1.4 ml.) and the reaction stirred for 1.6 hr. at +19°. The yellow solution was poured into water (100 ml.) and ethyl acetate (100 ml.) and the resulting insoluble solid was collected, washed with ethyl acetate and dried in vacuo over phosphorus pentoxide, to give diphenylmethyl 3-acetylthiomethyl-7β-formamidoceph-3-em-4-carboxylate, 1β-oxide (2.422 g, 49%), mp 198°–199° (dec.), $[\alpha]_D -60°$ (c 1.0, DMSO), $\lambda_{max.}$ (EtOH) 273 nm ($\epsilon$ 10,300), $\nu_{max.}$ (CHBr$_3$) 3430 (NH), 1803 (β-lactam) 1725 (CO$_2$R), 1695, 1505 (CONH), 1042 cm.$^{-1}$ (S→O) $\tau$ (DMSO-d$_6$), 1.66 (d, J 9; NH), 1.78 (s; CHO), 2.59 (m, phenyl), 3.01 (s, CHPh$_2$), 7.68 (s; SCH$_3$).

(b) Diphenylmethyl 3-acetylthiomethyl-7β-formamidoceph-3-em-4-carboxylate

A stirred solution of diphenylmethyl 3-acetylthiomethyl-7β-formamidoceph-3-em-4-carboxylate, 1β-oxide (1.00 g) in dry N,N-dimethylformamide (15 ml.) was cooled to −5° and treated with potassium iodide (0.67 g) and acetyl chloride (0.315 g). The brown solution was stirred for 5 min. at 0°, then for 30 min. after removal of the ice-bath. A solution of sodium metabisulphite (0.60 g) in water (12 ml) was added, and the yellow suspension was stirred for 5 mins. at 20°, then poured into water (200 ml.) and extracted with dichloromethane. The combined extracts were washed with water, dried and the solvent removed in vacuo to give diphenylmethyl 3-acetylthiomethyl-7β-formamidoceph-3-em-4-carboxylate as a pale yellow powder (0.92 g, 94%), $[\alpha]_D -136°$ (c 1.0, DMSO), $\lambda_{max.}$ 268 nm (EtOH) ($\epsilon$ 8,950).

(c) Diphenylmethyl 3-acetylthiomethyl-7β-aminoceph-3-em-4-carboxylate hydrochloride A stirred suspension of diphenylmethyl 3-acetylthiomethyl-7β-formamidoceph-3-em-4-carboxylate (0.505 g) in methanol:ether (1:1, 3 ml.) at 0° was treated over 10 min. with phosphorus oxychloride (0.468 g.) The ice bath was removed and stirring continued for a further 20 min, when a clear solution resulted. The reaction was cooled to 0°, and a white crystalline precipitate appeared. Ether (15 ml.) was added and the precipitate filtered off, washed with ether and dried in vacuo to give diphenylmethyl 3-acetylthiomethyl-7β-aminoceph-3-em-4-carboxylate hydrochloride (0.456 g, 89%) as white microcrystals; m.p. 155°–160° (d) $[\alpha]_D -91°$ (c 0.83 in DMSO), $\lambda_{max}$ (EtOH) 268 nm ($\epsilon$ 8,700), $\nu_{max.}$ (Nujol) 1770 (β-lactam), 1720 (CO$_2$R), 1702 cm.$^{-1}$ (SCOCH$_3$), $\tau$ (DMSO-d$_6$) values include 2.60 (m; Ph), 3.02 (s, CHPh$_2$), 7.66 (s, SCOCH$_3$).

EXAMPLE 41

3-Crotonoyloxymethyl-7β-[2-hydroxyimino-2-(thien-2-yl)acetamido]ceph-3-em-4-carboxylic acid (syn-isomer)

A molar solution of 2-dichloroacetoxyimino-2-(thien-2-yl) acetyl chloride (syn-isomer) in ethyl acetate (2.15 ml.) was added to a solution of diphenylmethyl 7β-amino-3-crotonoyloxymethylceph-3-em-4-carboxylate (0.933 g) in ethyl acetate (15 ml.) containing propylene oxide (0.6 ml). After 30 minutes the solution was washed with 2 N-hydrochloric acid, sodium bicarbonate solution, water and brine, dried and concentrated to a foam (1.575 g.).

A solution of this foam (1.464 g) in anisole (2 ml) was treated with trifluoroacetic acid at 20°. After 5 minutes the solution was concentrated. The oily residue was dissolved in ethyl acetate and the solution was washed with water. The ethyl acetate solution was then thrice extracted with dilute sodium bicarbonate solution. The combined extracts were washed with ethyl acetate and then taken to pH 2 with concentrated hydrochloric acid. The solution was extracted with ethyl acetate and the extract was washed with water and brine, dried and concentrated to a foam. Addition of ethyl acetate to this foam produced crystals which were filtered off and washed with ethyl acetate to give the title oxime, $[\alpha]_D^{25}+60°$ (c 1 in DMSO) $\lambda_{max.}$ (pH 6 phosphate buffer) 261 nm ($\epsilon$ 16,270) $\nu_{max.}$ (Nujol) include 1775 ($\beta$-lactam), 1733 (unsaturated ester), 1658 and 1545 (CONH) and 960 cm$^{-1}$ (trans CH=CH) $\tau$ (DMSO-d$_6$) values include 0.26 (doublet 8 Hz, NH) 2.38 and 2.83 (2 multiplets; thienyl protons) 6.29 and 6.49 (doublets, J 18 Hz; C-2H$_2$), 8.13 (doublets J 7 and 1 Hz; —CH=-CH—CH$_3$).

EXAMPLE 42

7$\beta$-[2-Hydroxyimino-2-(thien-2-yl)-acetamido]-3-(1-phenyltetrazol-5-ylthiomethyl)-ceph-3-em-4-carboxylic acid (syn-isomer)

A solution of 2-dichloroacetoxyimino-2-(thien-2-yl)-acetyl chloride (syn-isomer) in methylene dichloride (7 mls of 15% solution, ca. 3.5 mmole) was added, over 5 minutes, to a stirred solution of diphenylmethyl 7$\beta$-amino-3-(1-phenyltetrazol-5-ylthiomethyl)-ceph-3-em-4-carboxylate hydrochloride (1.779 g.) and propylene oxide (1.5 ml.) in dry methylene dichloride (25 ml.). After stirring for a further 20 minutes at 23°, the solution was washed successively with saturated sodium bicarbonate, water, and brine (25 ml. of each), and dried and evaporated to a foam (2.62 g.). A solution of this foam in benzene (10 ml.) was purified by chromatography on kieselgel with benzene:ethyl acetate (10:1), as eluent. Appropriate fractions were combined and evaporated to dryness in vacuo to give diphenylmethyl 7$\beta$-[2-hydroxyimino-2-(thien-2-yl)-acetamido]-3-(1-phenyl-tetrazol-5-yl-thiomethyl)-ceph-3-em-4-carboxylate as a foam (1.27 g). A solution of this foam in trifluoroacetic acid (5 ml.) and anisole (1 ml.) was kept at 23° for 5 minutes, and the solvents were removed in vacuo at 40°. The residue was dissolved in ethyl acetate (50 ml.), the solution extracted with sodium bicarbonate solution, and the alkaline extract covered with ethyl acetate (100 ml.) and acidified (to pH 2) with 2 N-hydrochloric acid. The organic phase was separated, and washed with water, and brine, dried and evaporated to a foam (750 mg.). A solution of this foam in ethyl acetate was added to petroleum to give the title acid as a pale-yellow solid (469 mg., 29%), $[\alpha]_D-51.4°$ (c 0.91, acetone), $\lambda_{max.}$ (pH 6 phosphate buffer) 264 nm ($\epsilon$ 19,500), $\nu_{max.}$ (Nujol) 3320 (NH), 1784 ($\beta$-lactam), 1722 (CO$_2$H), and 1674 and 1530 cm.$^{-1}$ (CONH), $\tau$ (DMSO-d$_6$) 0.26 (NH, doublet, J 8 Hz.), 2.31 (s;Ph), 4.13 (C 7-H, double doublet, J 5 and 8 Hz.), 4.82 (C 6-H, doublet, J 5 Hz.), 5.39 and 5.73 quartet, J 13 Hz; C-3 CH$_2$), and 6.28 (s; C-2 CH$_2$).

The amino ester used as starting material in the above acylation was prepared in a similar manner to the amino-ester described in Example 46 the 5-mercapto-2-phenyl-1,3,4-oxadiazole being replaced by 5-mercapto-1-phenyltetrazole, to give diphenylmethyl 7$\beta$-amino-3-(1-phenyltetrazol-5-ylthiomethyl)-ceph-3-em-4-carboxylate hydrochloride $\lambda_{max}$ (EtOH) 251.5 nm. ($\epsilon$ 10,000), $\nu_{max.}$ (CHBr$_3$) 1782 ($\beta$-lactam), and 1720 cm.$^{-1}$ (CO$_2$R), $\tau$ (DMSO-d$_6$) values include 2.32 (Ph—N<), 4.73 (C-6 H and C-7 1.), 5.32 and 5.68 (C-3 CH$_2$, quartet, J 14 Hz.), and 6.10 (C-2 CH$_2$).

EXAMPLE 43

7$\beta$-[2-Hydroxyimino-2-(thien-2-yl)-acetamido]-3-(1-methyltetrazol-5-ylthiomethyl)-ceph-3-em-4-carboxylic acid (syn-isomer)

A solution of 2-dichloroacetoxyimino-2-(thien-2-yl)a-cetyl chloride (syn-isomer) in dry methylene dichloride (6 ml. of 15% solution, ca. 3 mmole.) was added, over 5 minutes, to a solution of diphenylmethyl 7$\beta$-amino-3-(1-methyltetrazol-5-ylthiomethyl)-ceph-3-em-4-carboxylate (1.24 g.) and propylene oxide (0.8 ml.) in methylene dichloride (20 ml.). After stirring for 30 minutes at 23°, aqueous sodium bicarbonate was added, and the two-phase mixture stirred for a further 30 minutes. The organic phase was separated, and washed with brine, and dried and evaporated to a foam (2.0 g.). A solution of this foam in benzene (20 ml.) was purified by chromatography on kieselgel with benzene; ethyl acetate (5:1) as eluent. Appropriate fractions were combined and evaporated in vacuo to give diphenylmethyl 7$\beta$-[2-hydroxyimino-2-(thien-2-yl)-acetamido]-3-(1-methyltetrazol-5-ylthiomethyl)-ceph-3-em-4-carboxylate as a foam (1.68 g.). A solution of this foam in trifluoroacetic acid (6 ml) and anisole (1.5 ml) was kept at 23° for 5 minutes, and the solvents were removed at 40° (2 mm). The residue was dissolved in ethyl acetate (30 ml.), and the solution extracted with sodium bicarbonate solution. The alkaline extract was covered with ethyl acetate, and acidified to pH 2 with 2 N-hydrochloric acid. The organic phase was separated, and washed with water, and brine, and the solvent evaporated in vacuo. The residue was dissolved in acetone, the solution treated with some charcoal and filtered through a pad of kieselguhr; the filtrate was dried and evaporated to a foam (1.085 g.). A solution of this foam in ethyl acetate was run into petroleum to give the title acid as a colourless, amorphous solid (852 mg, 71%) $[\alpha]_D^{23}-90°$ (c 0.91, acetone), $\lambda_{max.}$ (pH 6 phosphate buffer) 267.5 nm, ($\epsilon$ 18,000), $\nu_{max}$ (Nujol) 3290 (NH), 1780 ($\beta$-lactam), 1720 (CO$_2$H), and 1670 and 1530 cm.$^{-1}$ (CONH), $\tau$ (DMSO-d$_6$) values include 0.25 (NH, doublet, J 8 Hz.), 4.14 (C-7 H, double doublet, J 4.5 and 8 Hz.), 4.79 (C-6 H, doublet, J 4.5 Hz), 6.05 (CH$_3$).

In a similar manner was prepared:

EXAMPLE 44

7$\beta$-[2-Hydroxyimino-2-(fur-2-yl)acetamido]-3-(1-methyltetrazol-5-ylthiomethyl)-ceph-3-em-4-carboxylic acid (syn-isomer)

$[\alpha]_D^{22}-102°$ (c 0.9 acetone), $\lambda_{max.}$ (pH 6 phosphate buffer) 273.5 nm ($\epsilon$ 20,700) $\nu_{max.}$ (Nujol) 3280 (NH), 1780 ($\beta$-lactam), 1720 (CO$_2$H) and 1674 and 1530 cm.$^{-1}$ (CONH), $\tau$ (DMSO-d$_6$) values include 0.33 (NH, doublet J 8 Hz), and 6.07 (CH$_3$).

The starting ester for the acylations in Examples 43 and 44 was prepared by the following route:

(a) Diphenylmethyl 3-(1-methyltetrazol-5-ylthiomethyl)-7$\beta$-(2-thienylacetamido)-ceph-3-em-4-carboxylate A solution of diphenylmethyl 3-bromomethyl-7$\beta$-(2-thienylacetamido)-ceph-3-em-4-carboxylate (17.505 g.) and 5-mercapto-1-methyltetrazole (3.486 g.) in dry tetrahydrofuran (250 ml.) was stirred at 10° and treated, over 5 minutes, with a solution of triethylamine (4.16 ml.) in dry tetrahydrofuran (50 ml.). The resulting suspension was stirred for a further 45 minutes (during which time the temperature was allowed to rise to ca. 20°) and then added, over 5 minutes, to a stirred mixture of 2 N-hydrochloric acid (50 ml.), water (700 ml.), brine (700 ml.), and ethyl acetate (1.5 l.). The organic phase was separated, washed with 2 N-hydrochloric acid, water and brine, treated with some charcoal and filtered through a pad of kieselguhr. The filtrate was dried and evaporated to a foam (20.6 g.). This foam was dissolved in hot methanol (200 ml.), and the solution cooled to give the ester as colourless plates (14.391 g., 77.5%), $\lambda_{max}$. (EtOH) 264 nm, ($\epsilon$8,700), $\nu_{max}$. (CHBr$_3$) 3420 (NH), 1780 ($\beta$-lactam), 1710 (CO$_2$R), and 1680 and 1502 cm.$^{-1}$ (CONH), $\tau$ (CDCl$_3$) values include 3.40 (NH, doublet, J 9 Hz.), (C.7 H, double doublet, J 5 and 9 Hz.), 5.02 (C-6 H, doublet, J 5 Hz.), 6.19 (CH$_3$).

(b) Diphenylmethyl 7$\beta$-amino-3-(1-methyltetrazol-5-yl-thiomethyl)-ceph-3-em-4-carboxylate A suspension of phosphorus pentachloride (416 mg) in dry methylene dichloride (10 ml.) was stirred at 23° and a solution of pyridine (0.16 ml) added. The warm suspension was stirred for 10 minutes, and cooled to 0°, and treated, over 10 minutes, with a solution of diphenylmethyl 3-(1-methyltetrazol-5-ylthiomethyl)-7$\beta$-(2-thienylacetamido)-ceph-3-em-4-carboxylate (619 mg) in methylene dichloride (15 ml.). After stirring for a further 45 minutes, during which time the temperature was allowed to rise to 23°, the solution was added, over 5 minutes, to a stirred and cooled (0°) mixture of methanol (5 ml.) and methylene dichloride (15 ml.). The resulting solution was stirred for a further 10 minutes, and washed with N-hydrochloric acid (20 ml.), and stirred for 30 minutes with saturated sodium bicarbonate sodium (50 ml.). The organic phase was separated, and washed with saturated aqueous sodium bicarbonate (25 ml.), and treated with some charcoal. The mixture was filtered through a pad of kieselguhr, and the filtrate evaporated to a gum (640 mg.), which was triturated with ether (20 ml) to give the amine as an off-white solid (403 mg, 81.5%), $\lambda_{max}$. (CHCl$_3$) 268.5 nm ($\epsilon$ 7,700), $\nu_{max}$. (CHBr$_3$) 3416 and 3350 (NH$_2$), 1780 ($\beta$-lactam), and 1720 cm.$^{-1}$ (CO$_2$R), $\tau$ (CDCl$_3$) values include 5.00 and 5.15 (C-6H and C-7 H, two doublets, J 5 Hz.), 6.14 (CH$_3$—), and 7.59 (NH$_2$).

EXAMPLE 45

In a similar manner to Example 43, acylation of diphenylmethyl 7$\beta$-amino-3-(5-methyl-1,3,4-thiadiazolyl-2-)-thiomethylceph-3-em-4-carboxylate with syn-2-dichloroacetoxyimino-2-(fur-2-yl)acetyl chloride and subsequent deprotection gave 7$\beta$-[2-hydroxyimino-2-(fur-2-yl) acetamido]-3-(5-methyl-1,3,4-thiadiazol-2-yl)thiomethylceph-3-em-4-carboxylic acid (syn-isomer), $\tau$ (DMSO-d$_6$) values inside 0.36 (d, J 9 Hz, NH); 2.23; 3.39 (2S, furyl protons); 4.19 (dd, J 5 and 9 Hz, C.7 H), 4.83 (d, J 5Hz, C-6 H), 5.45, 5.90 (q, J 14 Hz, C-3 CH$_2$), 6.21, 6.44 (q, J 18 Hz, C-2 H$_2$) 7.33 (S, CH$_3$).

EXAMPLE 46

7$\beta$-[2-Hydroxyimino-2-(thien-2-yl)-acetamido]-3-(5-phenyl-1,3,4-oxadiazol-2-ylthiomethyl)-ceph-3-em-4-carboxylic acid (syn-isomer)

A solution of 2-dichloroacetoxyimino-2-(thien-2-yl)-acetyl chloride (syn-isomer) in methylene dichloride (7 ml. of 15% solution; was added, over 5 minutes, to a stirred solution of diphenylmethyl 7$\beta$-amino-3-(5-phenyl-1,3,4-oxadiazol-2-ylthiomethyl)-ceph-3-em-4-carboxylate hydrochloride (1.779 g.) and propylene oxide (1.5 ml.) in dry methylene dichloride (25 ml.). After stirring for a further 30 minutes, the solution was washed with saturated aqueous sodium bicarbonate, water and brine (25 ml. of each), and dried and evaporated to a foam (2.34 g.). A solution of this foam in benzene (10 ml.) was purified by chromatography on kieselgel with benzene:ethyl acetate (10:1) as eluent. Appropriate fractions were combined and evaporated to dryness in vacuo, and the residue was triturated with ether (25 ml.) to give diphenylmethyl 7$\beta$-[2-hydroxyimino-2-(thien-2-yl)-acetamido]-3-(5-phenyl-1,3,4-oxadiazol-2-ylthiomethyl)-ceph-3-em-4-carboxylate as colourless prisms (870 mg., 41%). A suspension of this ester (810 mg) in a mixture of trifluoroacetic acid (3 ml.) and anisole (0.8 ml.) was shaken at 23° until all the solid had dissolved (ca. 10 minutes.). The reagents were evaporated at 40° (2 mm), and the residue was dissolved in ethyl acetate. The solution was extracted with aqueous sodium bicarbonate, the alkaline extract covered with ethyl acetate and acidified to pH 2 with 2N-hydrochloric acid. The organic phase was separated, and washed with water, and brine and the solvent evaporated in vacuo. The residue was dissolved in acetone, the solution treated with some charcoal and filtered through a pad of kieselguhr; the filtrate was dried and evaported to a foam (470 mg.). A solution of this foam in ethyl acetate was run into petroleum to give the title acid as a colourless, amorphous solid (410 mg., 66%), $[\alpha]_D^{23}$ —118° (c 1.08, acetone), $\lambda_{max}$. (pH 6 phosphate buffer) 274 nm ($\epsilon$ 28,800), $\nu_{max}$. (Nujol) 3280 (NH), 1786 ($\beta$-lactam), 1720 (CO$_2$H), and 1672 and 1530 cm.$^{-1}$ (CONH), $\tau$ (DMSO-d$_6$) values include 0.24 (NH, doublet, J 8 Hz.), 4.15 (C-7 H, double doublet, J 4.5 and 8 Hz.), 4.78 (C-6 H, doublet, J 4.5 Hz.).

The amino-ester used for the above acylation was prepared in the following manner:

Diphenylmethyl 7 β-amino-3-(5-phenyl-1,3,4-oxadiazol-2-ylthiomethyl)-ceph-3-em-4-carboxylate hydrochloride p A solution of diphenylmethyl 3-bromomethyl-7β-formamidoceph-3-em-4-carboxylate-1β-oxide (10.07 g.) and 5-mercapto-2-phenyl-1,3,4-oxadiazole (3.564 g.) in dry N,N-dimethylformamide (250 ml.) was stirred at 0° and treated, over 10 minutes, with a solution of triethylamine (3.2 ml.) in N-dimethylformamide (20 ml.). The resulting solution was stirred for a further 2½ hours, during which time the temperature was allowed to rise to ca. 20°, and then the solvent was evaporated at 40° in vacuo. The residue was partitioned between methylene dichloride (250 ml.), and water (150 ml), and the organic phase separated, washed with 2N-hydrochloric acid, water, and brine, and dried and the solvent evaporated to give diphenylmethyl 7β-formamido-3-(5-phenyl-1,3,4-oxadiazol-2-ylthiomethyl)-ceph-3-em-4-carboxylate-1β-oxide as an orange solid (12.076 g.). A suspension of this material in dry methylene dichloride (250 ml.) was stirred at −20° and treated, over 10 minutes, with a solution of phosphorus tribromide (5.7 ml.) in methylene dichloride (25 ml.). The resulting solution was stirred for a further 1 hour at −10° to −15° and then added, over 10 minutes, to a stirred and cooled (0°) mixture of methylene dichloride and saturated sodium bicarbonate solution). The two-phase system was stirred for a further 1 hour at ca. 23°; the organic phase was separated, and washed with saturated sodium bicarbonate solution, and brine, and treated with some charcoal. The suspension was filtered, and the filtrate dried and evaporated in vacuo to give diphenylmethyl 7β-formamido-3-(5-phenyl-1,3,4-oxadiazol-2-ylthiomethyl)-ceph-3-em-4-carboxylate as a foam (11.231 g.). A suspension of this foam in a mixture of methanol (100 ml.) and ether (100 ml.) was stirred at 0° and treated, over 20 minutes, with phosphrous oxychloride (3.4 ml). After stirring for a further 3 hours, the suspension was poured into ether (200 ml.) to give the title hydrochloride as a light-brown solid (8.707 g., 77%), $\lambda_{max.}$(EtOH) 272 nm. ($\epsilon$ 21,200), $\upsilon_{max}$ .(Nujol) 1790 (β-lactam), and 1720 cm.$^{-1}$ (CO$_2$R), $\tau$ (DMSO-d$_6$) values include 4.70 (C-6 H and C-7 H), 5.42 and 5.65 (C-3 CH$_2$ quartet J 13 Hz.).

EXAMPLE 47

3-Acetoxymethyl-7β-[2-ethoxycarbonyloxyimino-2-(thien-2-yl)-acetamido]ceph-3-em-4-carboxylic acid (syn-isomer)

To a solution of sodium 3-acetoxymethyl-7β-[hydroxyimino-2-(thien-2-yl)acetamido]ceph-3-em-4-carboxylate (syn-isomer; 0.6 g) in saturated aqueous sodium bicarbonate solution (25 ml.) was added a solution of ethyl chloroformate (1.5 ml.) in ethyl acetate (20 ml.) and the whole shaken vigorously for one minute. The bicarbonate phase was separated and shaken with a second portion of ethyl chloroformate (1.0 ml) in ethyl acetate (20 ml.). The bicarbonate phase was separated, washed with ethyl acetate, acidified and extracted with ethyl acetate. The combined extracts were dried and concentrated to ca 5 ml. The concentrate was added dropwise with stirring to petroleum (b.p. 40°–60°; 200 ml.). The precipitated solid was filtered and dried to give the title acid (0.47 g) [α]$_D$+42° (c 0.9 DMSO), $\lambda_{max.}$ (pH 6 phosphate buffer) 265 nm. ($\epsilon$ 16,900), $\nu_{max.}$ (Nujol) 3290 (NH), 1784 (β-lactam), 1740 (acetate), 1690 and 1550 cm.$^{-1}$ (CONH), $\tau$ (DMSO-d$_6$) values include −0.16 (d; J 9 Hz; NH), 2.08, 2.53, 2.74 (three quartets; thienyl protons), 5.70 (q; J 8 Hz; —CH$_2$CH$_3$), 7.96 (s; OAc), 8.72 (t; J 8 Hz; —CH$_2$CH$_3$).

EXAMPLE 48

7β-[2-Acetoxyimino-2-(thien-2-yl)acetamido]-3-acetoxymethylceph-3-em-4-carboxylic acid (syn-isomer)

A solution of sodium 3-acetoxymethyl-7β-[2-hydroxyimino-2-(thien-2-yl)actamido]ceph-3-em-4-carboxylate (syn-isomer; 0.7 g) in water (20 ml.) was stirred with ethyl acetate (50 ml.) and the pH of the aqueous layer adjusted to 1 with 2N hydrochloric acid. The ethyl acetate phase was separated, combined with an ethyl acetate extraction of the aqueous phase, dried and evaporated to give an oil. The oil was dissolved in ethyl acetate (28 ml.) containing pyridine (2.1 g.) and treated dropwise with stirring at room temperature, with a solution of acetyl chloride (1.4 g) in ethyl acetate (14 ml.). After stirring for twelve minutes, the mixture was poured into 2N-hydrochloric acid, the ethyl acetate layer separated, washed with water, and extracted with saturated aqueous sodium bicarbonate solution. The combined extracts were washed with ethyl acetate, acidified (2N hydrochloric acid) and extracted three times with ethyl acetate. The combined organic extracts were dried, concentrated to 5 ml. and added dropwise to petroleum (b.p. 40°–60°; 250 ml.). The precipitated solid was filtered and dried to give the title acid (0.5 g.; 68%), $\lambda_{max.}$ (pH 6 phosphate buffer) 265 nm. ($\epsilon$ 15,500), $\nu_{max.}$ (Nujol) 3270 (NH), 1780 (β-lactam), 1736 (acetate), 1680 and 1540 cm.$^{-1}$ (CONH), $\tau$ (DMSO-d$_6$) values include −0.15 (d; J 9 Hz; NH), 2.08, 2.54, 2.73 (thien-2-yl protons), 7.79 (s; =NOCOCH$_3$), 7.94 (singlet, OCOCH$_3$)

EXAMPLE 49

3-Acetoxymethyl-7β-(2-chloroethylcarbamoyloxyimino)-2-(thien-2-yl)acetamido]ceph-3-em-4-carboxylic acid (syn-isomer)

A solution of sodium 3-acetoxymethyl-7β-[2-hydroxyimino-2-(thien-2-yl)acetamido]ceph-3-em-4-carboxylate (syn-isomer; 0.89 g) in dimethylformamide (11 ml.) containing triethylamine (0.22 g) was treated with 2-chloroethylisocyanate (0.25 g). The solution was allowed to stand at room temperature for thirty minutes, then at 5° for a further hour. It was poured into cold (5°) 2N hydrochloric acid, extracted three times with ethyl acetate, and the combined extracts washed with 2N-hydrochloric acid then water then extracted three times with a cold (5°) saturated aqueous sodium bicarbonate solution. The combined aqueous extracts were washed with ethyl acetate, acidified (2N-hydrochloric acid) and rapidly extracted with ethyl acetate. The combined extracts were dried, concentrated to ca. 5 ml., and the concentrate added dropwise to petroleum (b.p. 40°–60° 250 ml.) The precipitated solid was filtered and dried to give the title acid (0.8 g; 76%), [α]$_D$+33° (c 0.7 DMSO) $\lambda_{max.}$ (pH 6 phosphate buffer) 264 nm. ($\epsilon$ 17,200), $\nu_{max.}$ (Nujol), 1786 (β-lactam), 1734 (acetate), 1682 and 1508 cm.$^{-1}$ (CONH), $\tau$ (DMSO-d$_6$) values include −0.12 (doublet J 9 Hz; NH), 2.12, 2.56, 2.74 (three quartets; thienyl protons), 7.97 (s; OCOCH$_3$).

EXAMPLE 50

N-[7β-(2-Hydroxyimino-2-(fur-2-yl)acetamido)ceph-3-em-3-ylmethyl]-4'-carbamoylpyridinium 4-carboxylate (syn-isomer)

A solution of 3-acetoxymethyl-7β-[2-hydroxyimino(fur-2-yl)acetamido]ceph-3-em-4-carboxylic acid (2.5 g.) and isonicotinamide (2.5 g.) in water was heated at 65°–70° under nitrogen for 3½ hours. The cooled mixture was passed down a column of AG1X8 resin (acetate form) and eluted with water. Fractions were combined on the basis of electrophoretograms and freeze-dried to a white powder which was washed well with acetone and dried to afford the title compound (0.834 g., 29%), $[\alpha]_D -61°$ (c 0.84, DMSO), $\lambda_{max}$. (pH 6 buffer) 267.5 nm (ε 19,500), $\nu_{max}$ (Nujol) 3340 (NH), 1772 (β-lactam), 1680 and 1560 (CONH), 1608 cm.$^{-1}$ (CO$_2^-$), τ (d$_6$-DMSO) values include 0.40, 1.26, 1.50 and 1.75 (multiplets, aromatic protons), 1.26 and 1.75 (broad singlets; CONH$_2$), 4.26 (multiplet; C-7H), 4.28 and 4.77 (C-3 CH$_2$), 4.88 (d, J 5 Hz; C-6 H).

EXAMPLE 51

3-Acetoxymethyl-7β-[2-hydroxyimine-2-(pyrid-4-yl)acetamido]ceph-3-em-4-carboxylic acid trifluoroacetic acid salt (syn-isomer).

(a) t-Butyl 3-acetoxymethyl-7β-(pyrid-4-ylacetamido)ceph-3-em-4-carboxylate

A suspension of pyrid-4-ylacetyl chloride hydrochloride (6.0 g.) in ethyl acetate (50 ml.) containing propylene oxide (12 ml.) was stirred, cooled in ice and treated dropwise with a solution of t-butyl 3-acetoxymethyl-7β-aminoceph-3-em-4-carboxylate (5.0 g.) in ethyl acetate (50 ml.). The mixture was stirred at 20° for 20 hours and then washed with saturated sodium bicarbonate solution and extracted with 2N hydrochloric acid. The aqueous extract was washed with ethyl acetate, neutralised with saturated sodium bicarbonate solution and extracted with ethyl acetate. The extract was washed with water, dried over magnesium sulphate and evaporated to small bulk whereupon crystallization began. The crystalline solid was washed well with petroleum spirit (bp. 40°–60°) and dried to give the title ester as a buff coloured powder (5.4 g., 80% based on amine). A portion (250 mg.) was recrystallised from ethyl acetate as white needles (170 mg.), $[\alpha]_D +94°$ (c 0.9, DMSO) $\epsilon_{max}$. (EtOH) 256.5 nm (ε 9,900), $\nu_{max}$. (CHBr$_3$) 3412 (NH)$^-$, 1784 (β-lactam), 1736 (OAc), 1722 (CO$_2$R), 1690 and 1512 cm.$^{-1}$ (CONH), τ (d$_6$-DMSO) 0.81 (d, J 8 Hz; NH), 1.47 and 2.68 (2d, J 5 Hz; aromatic protons), 4.27 (q, J 8 and 5 Hz; C-7H), 4.85 (d, J 5 Hz; C-6 H), 5.01 and 5.36 (2d, J 13 Hz; C-3CH$_2$), 6.38 (s; CH$_2$CONH), 6.39 (s; C-2CH$_2$), 7.96 (s; OCOCH$_3$), and 8.50 (s; C(CH$_3$)$_3$).

(b) t-Butyl 3-acetoxymethyl-7β-[2-hydroxyimino(pyrid-4-yl)acetamido]-ceph-3-em-4-carboxylate A solution of t-butyl 3-acetoxymethyl-7β-(pyrid-4-ylacetamido)ceph-3-em-4-carboxylate (3.0 g.) in acetic acid (30 ml.) was stirred, cooled briefly in ice and treated dropwise over 3–4 minutes with a solution of sodium nitrite (1.38 g.), in water (10 ml.). The mixture was stirred at 20° for 30 minutes and was then diluted with water and extracted with ethyl acetate. The organic extract was washed with saturated sodium bicarbonate solution and water and then dried over magnesium sulphate. Evaporation almost to dryness gave a residue which was dissolved in the minimum volume of acetone and added dropwise to stirred petroleum spirit (bp. 40°–60°). The resulting solid was collected, washed with petroleum spirit and dried to yield the title oxime as a white powder (2.9 g., 91%) which was shown (NMR) to be a syn/anti-mixture (30:/0).

The oxime mixture (2.5 g) was chromatographed on silica gel and eluted with methanol-chloroform (1:49) to give the title compound (anti-isomer, 1.09 g., 44% from mixture).

Further elution with methanol-chloroform (1:49) gave material which was dissolved in acetone and added to stirred petroleum (bp. 40°–60°) to afford t-butyl 3-acetoxymethyl-7β-[2-hydroxyimino(pyrid-4-yl)acetamido]ceph-3-em-4-carboxylate (syn-isomer, 0.81 g., 32% from mixture), $[\alpha]_D +57°$ (c 1.11, DMSO), $\lambda_{max}$. (EtOH) 253.5 nm (ε17,600), $\lambda_{max}$. (Nujol) 3220 (NH), 1784 (β-lactam), 1744 (OAc), 1710 (CO$_2$R) 1640 and 1526 cm.$^{-1}$ (CONH), τ (d$_6$-DMSO) −2.26 (s; NOH), 0.27 (d, J 8 Hz; NH), 1.33 and 2.47 (2d, aromatic protons), 4.04 (q, J 5 and 8 Hz; C-7H), 4.71 (d, J 5 Hz; C-6H), 4.98 and 5.33 (2d, J 13 Hz; C-3 CH$_2$), 6.20 and 6.53 (2d, J 18 Hz; C-2 CH$_2$) 7.94 (s, OCOCH$_3$), 8.49 (s, C(CH$_3$)$_3$).

(c) The syn-t-butyl ester (0.6 g.) in trifluoroacetic acid (15 ml.) was stood at 20° for 15 min. and then evaporated to dryness. The residue was treated with acetone and the solvent removed in vacuo, this process was then repeated. The residue in acetone was slowly added to petroleum (bp. 40°–60°).

The precipitate was collected and dried affording 3-acetoxymethyl-7β-[2-hydroxyimino-2-(pyrid-4-yl)acetamido]ceph-3-em-4-carboxylic acid trifluoroacetic acid salt (syn-isomer) (0.66 g., 99%), $[\alpha]_D +47.5°$ (c 0.84, DMSO), $\lambda_{max}$. (pH 6 buffer) 248.5 nm (ε17,000), $\lambda_{max}$. (Nujol) 3250 (NH), 1772 (β-lactam), 1720 (OAc), 1660 (CF$_3$CO$_2^-$), 1660 and 1530 cm.$^{-1}$ (CONH), τ (d$_6$-DMSO) 0.16 (d, J 8 Hz; NH), 1.14 and 2.20 (multiplets, aromatic protons), 4.06 (q, J 5 and 8 Hz; C-7H), 4.71 (d, J 5 Hz; C-6H), 4.92 and 5.24 (2d, J 13 Hz; C-CH$_2$), 6.25 and 6.61 (2d, J 18 Hz; C-2 CH$_2$), 7.93 (s; OCOCH$_3$).

EXAMPLE A

Dry Powder for Injection

The sterile sodium 3-acetoxymethyl-7β-[2-hydroxyimino(thien-2-yl)acetamido]ceph-3-em-4-carboxylate (syn-isomer) powder was filled into glass vials, the claimed fill weights being 500 mg. and 1.0 g antibiotic. Filling was carried out aseptically under a blanket of nitrogen. The vials were closed using rubber discs held in position by aluminium sealing rings, thereby preventing gaseous exchange or ingress of micro-organisms. The product was intended for reconstitution with water for injections or other suitable sterile vehicle shortly before administration.

EXAMPLE B

Intramammary Infusion for Cattle

| Percentage composition (w/w) | |
|---|---|
| Sodium 3-acetoxymethyl-7β-[2-hydroxyimino-(thien-2-yl)acetamido]-ceph-3-em-4-carboxylate (syn-isomer) | 10.00 |
| Vehicle to: | 100.00 |
| Vehicle Tween 60 | 3.00 |

| Percentage composition (w/w) | |
|---|---|
| White Beeswax | 6.00 |
| Arachis Oil | 91.00 |

The last three ingredients were heated together at 150° C. for one hour and then cooled to room temperature with stirring. The sterile antibiotic powder was added aseptically to this vehicle and the product refined with a high speed stirrer. The preparation was filled aseptically into sterile collapsible aluminium tubes with a fill weight of 3.0 g., each tube containing 300 mg. cephalosporin derivative.

We claim:

1. A cephalosporin antibiotic of the formula

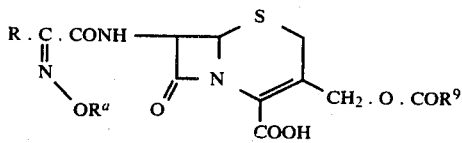

wherein R is phenyl, naphthyl, thienyl, furyl, pyridyl, or phenyl substituted by chloro;
$R^a$ is H or

wherein $R^c$ is $C_{1-4}$ alkyl, $C_{1-4}$ chloroalkyl, $C_{1-4}$ alkoxy, phenyl, nitrophenyl, $C_{1-4}$ alkylamino or $C_{1-4}$ chloroalkylamino; and
$R^9$ is (a) $C_nH_{2n+1}$ where n is an integer from 1–7;
(b) $C_nH_{2n-1}$ where n is an integer from 2–7;
(c) $R^v$ where $R^v$ is selected from the group consisting of phenyl, hydroxyphenyl, chlorophenyl, fluorophenyl, tolyl, nitrophenyl, aminophenyl, methoxyphenyl, methylthiophenyl, thien-2-yl, thien-3-yl, pyridyl, cyclohexyl, cyclopentyl, sydnone, naphthyl or 2-ethoxynaphthyl; or
(d) $R^v(CH_2)_m$ where $R^v$ has the meaning defined above under (c) and m is an integer from 1–4; or a physiologically acceptable salt thereof, said cephalosporin antibiotic being in the form of a syn-isomer free of the corresponding anti-isomer to the extent of at least 75% based on the total weight of said antibiotic.

2. The compound of claim 1 which is 3-acetoxymethyl-7β-[2-hydroxyimino-2-phenylacetamido]ceph-3-em-4-carboxylic acid (syn-isomer).

3. The compound of claim 1 which is sodium 3-acetoxymethyl-7β-[2-hydroxyimino-2-phenylacetamido]ceph-3-em-4-carboxylate (syn-isomer).

4. The compound of claim 1 which is 3-acetoxymethyl-7β-[2-hydroxyimino-2-(thien-2-yl)acetamido]ceph-3-em-4-carboxylic acid (syn-isomer).

5. The compound of claim 1 which is sodium 3-acetoxymethyl-7β-[2-hydroxyimino-2-(thien-2-yl)acetamido]ceph-3-em-4-carboxylate (syn-isomer).

6. The compound of claim 1 which is 7β-(2-hydroxyimino-2-phenylacetamido)-3-pivaloyloxymethylceph-3-em-4-carboxylic acid (syn-isomer).

7. The compound of claim 1 which is 3-benzoyloxymethyl-7β-(2-hydroxyimino-2-phenylacetamido)ceph-3-em-4-carboxylic acid (syn-isomer).

8. The compound of claim 1 which is 3-crotonoyloxymethyl-7β-(2-hydroxyimino-2-phenylacetamido)ceph-3-em-4-carboxylic acid (syn-isomer).

9. The compound of claim 1 which is 7β-(2-hydroxyimino-2-phenylacetamido)-3-isobutyryloxymethylceph-3-em-4-carboxylic acid (syn-isomer).

10. The compound of claim 1 which is 3-acetoxymethyl-7β-[2-(4-chlorophenyl)-2-hydroxyiminoacetamido]ceph-3-em-4-carboxylic acid (syn-isomer).

11. The compound of claim 1 which is 3-acetoxymethyl-7β-(2-hydroxyimino-2-naphth-1′-ylacetamido)ceph-3-em-4-carboxylic acid (syn-isomer).

12. The compound of claim 1 which is 7β-(2-acetoxyimino-2-phenylacetamido)-3-acetoxymethylceph-3-em-4-carboxylic acid (syn-isomer).

13. The compound of claim 1 which is 3-acetoxymethyl-7β-(2-chloroacetoxyimino-2-phenylacetamido)ceph-3-em-4-carboxylic acid (syn-isomer).

14. The compound of claim 1 which is 3-acetoxymethyl-7β-(2-ethoxycarbonyloxyimino-2-phenylacetamido)ceph-3-em-4-carboxylic acid (syn-isomer).

15. The compound of claim 1 which is 3-acetoxymethyl-7β-(2-benzoyloxyimino-2-phenyl-acetamido)-ceph-3-em-4-carboxylic acid (syn-isomer).

16. The compound of claim 1 which is 3-acetoxymethyl-7β-[2-(4-nitrobenzoyloxyimino)-2-phenylacetamido]ceph-3-em-4-carboxylic acid (syn-isomer).

17. The compound of claim 1 which is 3-acetoxymethyl-7β-(2-ethylcarbamoyloxyimino-2-phenylacetamido)ceph-3-em-4-carboxylic acid (syn-isomer).

18. The compound of claim 1 which is 3-acetoxymethyl-7β-[2-(2-chloroethyl)carbamoyloxyimino-2-phenylacetamido]ceph-3-em-4-carboxylic acid (syn-isomer).

19. The compound of claim 1 which is 3-acetoxymethyl-7β-[2-hydroxyimino-2-(thien-3-yl)acetamido]-ceph-3-em-4-carboxylic acid (syn-isomer).

20. The compound of claim 1 which is 3-acetoxymethyl-7β-[2-hydroxyimino-2-(fur-2-yl)acetamido]-ceph-3-em-4-carboxylic acid (syn-isomer).

21. The compound of claim 1 which is 3-acetoxymethyl-7β-[2-ethoxycarbonyloxyimino-2-(thien-2-yl)-acetamido]ceph-3-em-4-carboxylic acid (syn-isomer).

22. The compound of claim 1 which is 7β-[2-acetoxyimino-2-(thien-2-yl)acetamido]-3-acetoxymethylceph-3-em-4-carboxylic acid (syn-isomer).

23. The compound of claim 1 which is 3-acetoxymethyl-7β-[2-chloroethylcarbamoyloxyimino)-2-(thien-2-yl)acetamido]ceph-3-em-4-carboxylic acid (syn-isomer).

24. The compound of claim 1 which is 3-acetoxymethyl-7β-[2-hydroxyimino-2-(pyrid-4-yl)acetamido]-ceph-3-em-4-carboxylic acid (syn-isomer).

25. The compound of claim 1 which is 3-crotonoyloxymethyl-7β-[2-hydroxyimino-2-(thien-2-yl)acetamido]-ceph-3-em-4-carboxylic acid (syn-isomer).

* * * * *